(12) United States Patent
Hill et al.

(10) Patent No.: US 10,525,280 B2
(45) Date of Patent: Jan. 7, 2020

(54) DEVICES AND METHODS FOR TREATING SUBJECTS

(71) Applicant: ROGERS SCIENCES, INC., Boston, MA (US)

(72) Inventors: Samuel L. Hill, Boston, MA (US); Gary S. Rogers, Wenham, MA (US); Patrick J. McMullan, Canton, CT (US)

(73) Assignee: ROGERS SCIENCES, INC., Boston, MA (US)

( * ) Notice: Subject to any disclaimer, the term of this patent is extended or adjusted under 35 U.S.C. 154(b) by 0 days.

(21) Appl. No.: 16/181,899

(22) Filed: Nov. 6, 2018

(65) Prior Publication Data

US 2019/0070432 A1    Mar. 7, 2019

Related U.S. Application Data

(63) Continuation of application No. 16/008,899, filed on Jun. 14, 2018.

(Continued)

(51) Int. Cl.
*A61N 5/06* (2006.01)
*A61M 1/00* (2006.01)
(Continued)

(52) U.S. Cl.
CPC ........ *A61N 5/0624* (2013.01); *A61F 13/0206* (2013.01); *A61M 1/0088* (2013.01); *A61N 5/062* (2013.01); *A61N 5/0616* (2013.01); *A61N 2005/063* (2013.01); *A61N 2005/067* (2013.01); *A61N 2005/0645* (2013.01); *A61N 2005/0652* (2013.01); *A61N 2005/0653* (2013.01); *A61N 2005/0659* (2013.01); *A61N 2005/0661* (2013.01); *A61N 2005/0663* (2013.01); *A61N 2005/0665* (2013.01)

(58) Field of Classification Search
CPC .... A61N 2005/0632; A61N 2005/0644; A61N 2005/0645; A61N 2005/0647; A61N 2005/0648; A61N 2005/0649; A61N 2005/065; A61N 2005/0651; A61N 2005/0652; A61N 2005/0653
See application file for complete search history.

(56) References Cited

U.S. PATENT DOCUMENTS 5,344,434 A   9/1994  Talmore
7,422,598 B2  9/2008  Altshuler et al.
(Continued)

OTHER PUBLICATIONS

International Search Report and Written Opinion in application No. PCT/US2018/037611 dated Aug. 28, 2018.

*Primary Examiner* — Brian T Gedeon
(74) *Attorney, Agent, or Firm* — Lando & Anastasi, LLP

(57) ABSTRACT

One aspect of the present disclosure is directed to a device for providing light to the surface of a subject, comprising an array of a plurality of light emitting modules, wherein the plurality comprises four light emitting modules, each module of the plurality is flexibly connected to another module of the plurality, and two of the modules of the plurality comprise a polygonal perimeter having 4, 5, or 6 major sides, a light source, and a longest apex-to-apex dimension for a module of 5-50 millimeters, and, optionally, a non-adherent member configured to be adjacent to the subject.

20 Claims, 42 Drawing Sheets

Related U.S. Application Data

(60) Provisional application No. 62/555,128, filed on Sep. 7, 2017, provisional application No. 62/520,856, filed on Jun. 16, 2017.

(51) Int. Cl.
*A61F 13/02* (2006.01)
*A61N 5/067* (2006.01)

(56) References Cited

U.S. PATENT DOCUMENTS

| | | |
|---|---|---|
| 9,662,508 B2 | 5/2017 | Delp et al. |
| 2004/0260365 A1 | 12/2004 | Groseth et al. |
| 2007/0208395 A1* | 9/2007 | Leclerc ................ A61N 5/0616 607/86 |
| 2007/0239232 A1 | 10/2007 | Kurtz et al. |

* cited by examiner

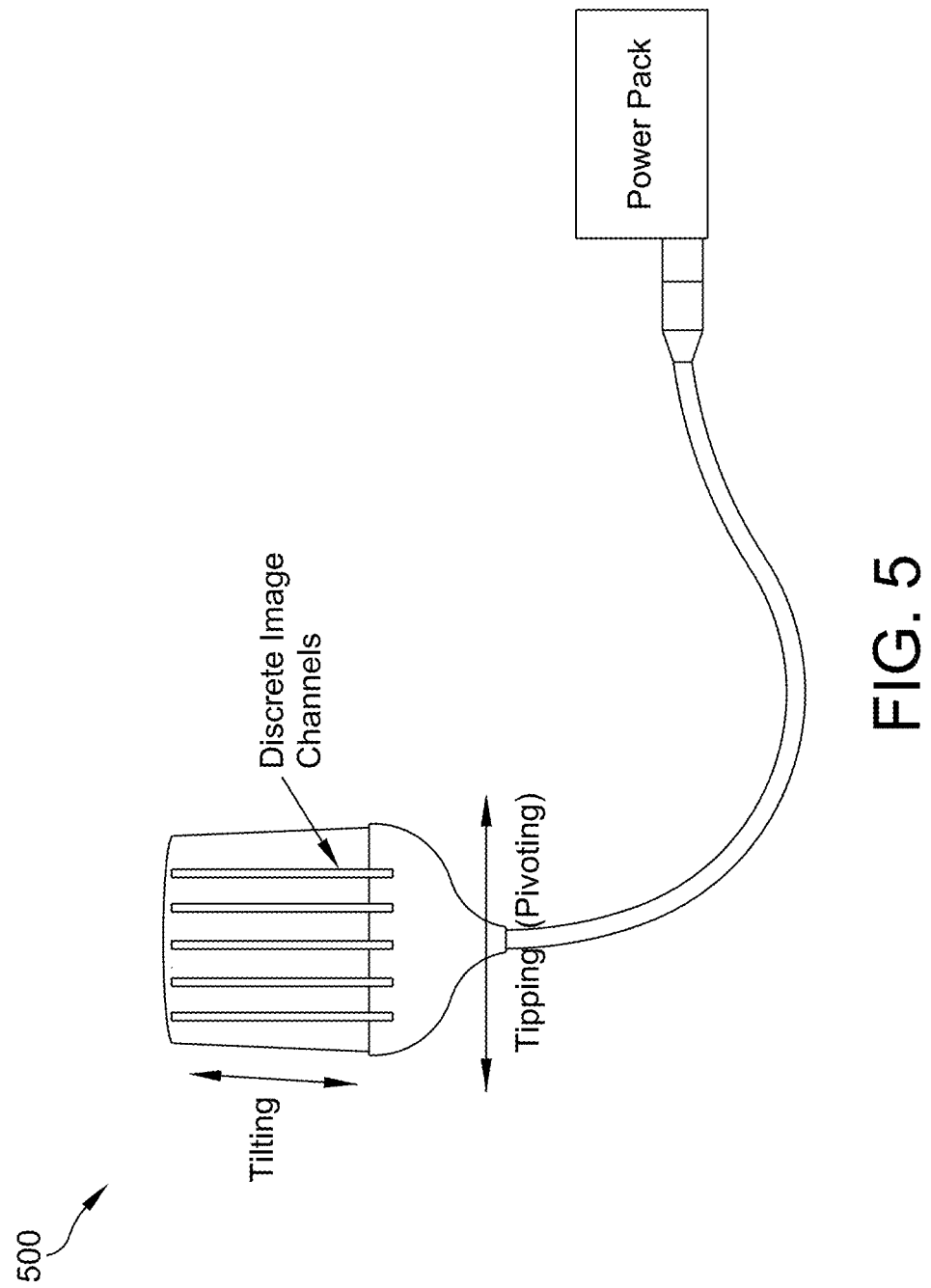

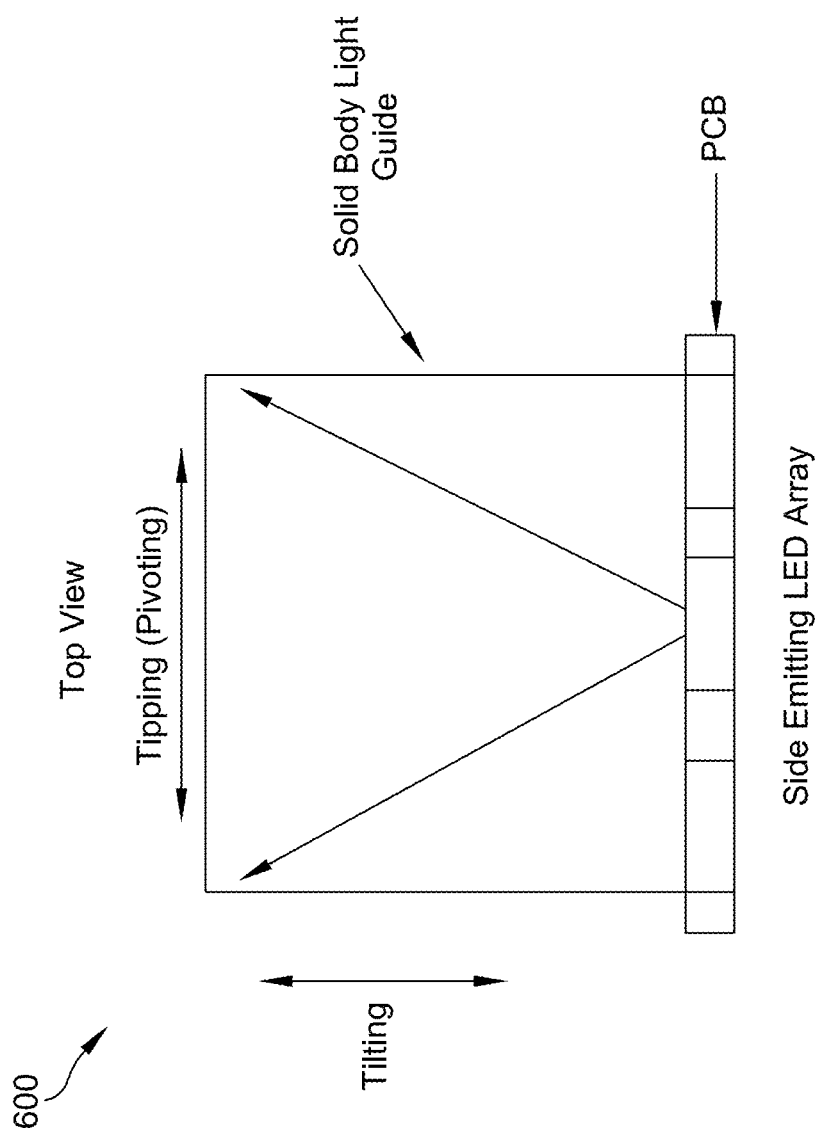

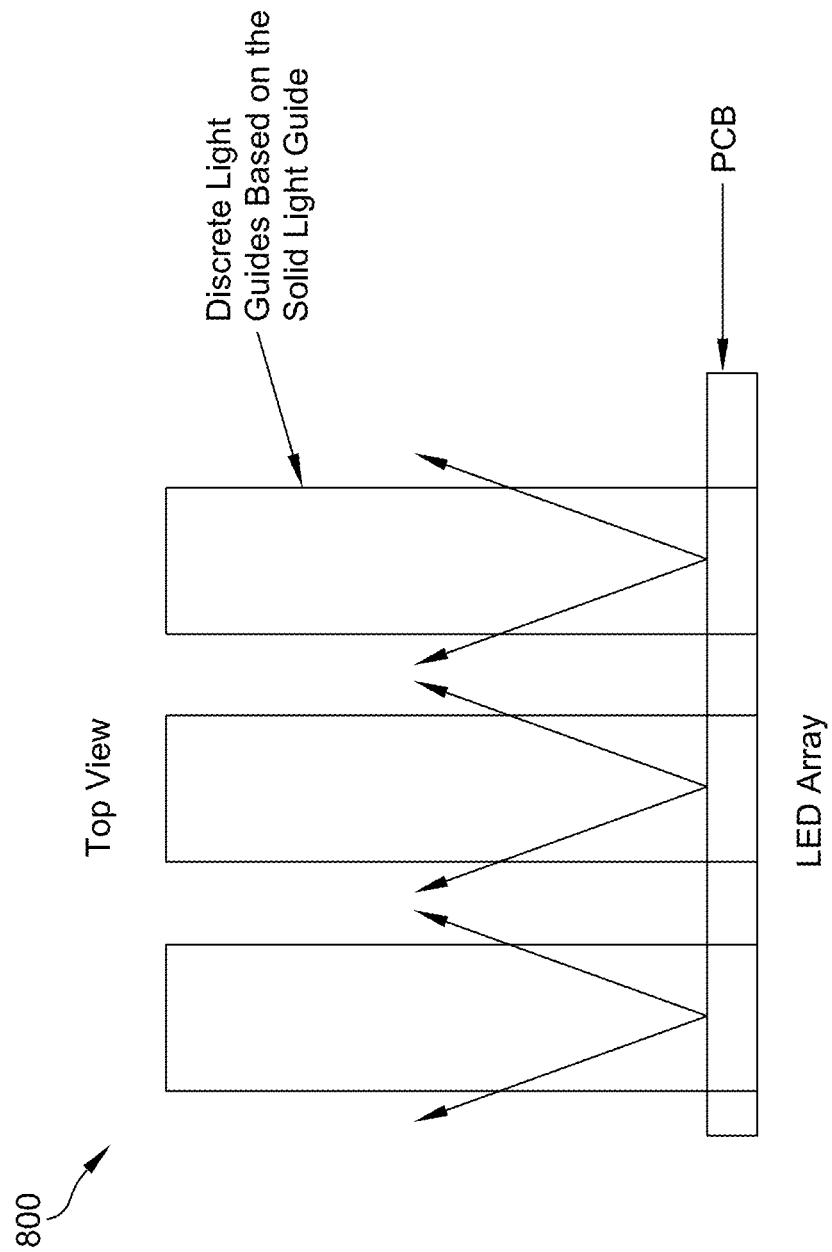

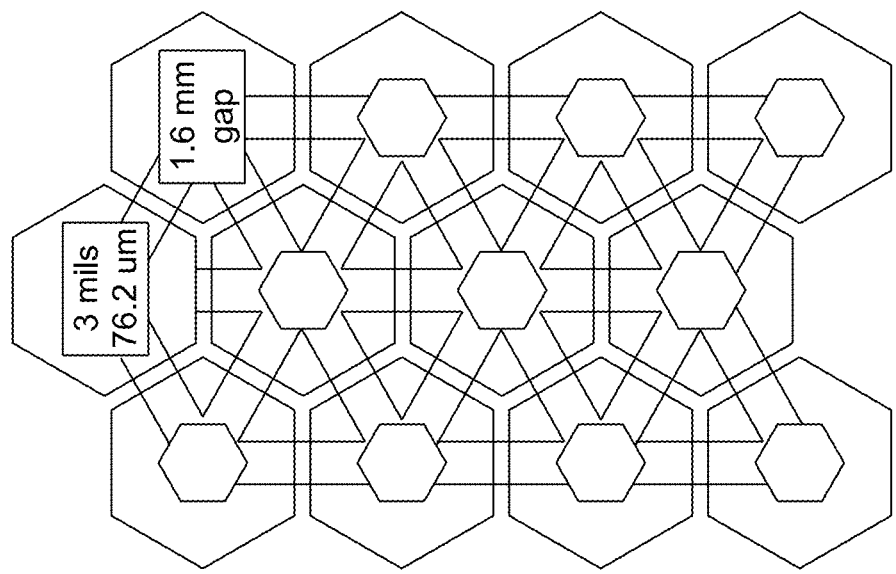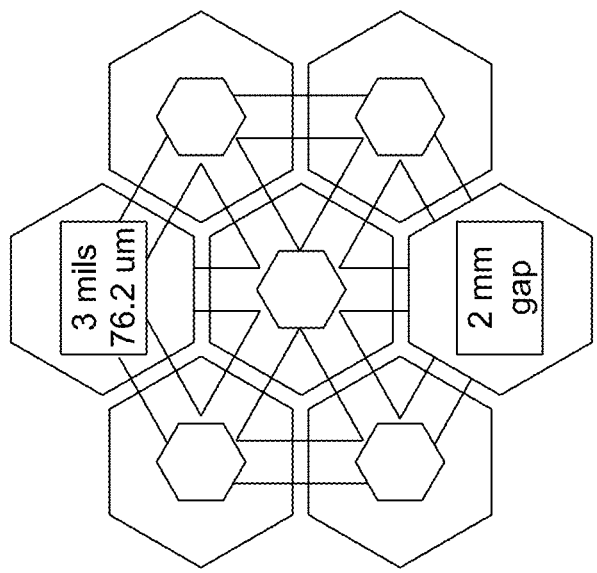
FIG. 11

3400

DEVICES AND METHODS FOR TREATING SUBJECTS

CROSS-REFERENCE TO RELATED APPLICATIONS

This application claims priority under 35 U.S.C. § 120 as a continuation of U.S. patent application Ser. No. 16/008,899, titled "DEVICES AND METHODS FOR TREATING SUBJECTS," filed Jun. 14, 2018, which claims priority under 35 U.S.C. § 119(e) to U.S. Provisional Application Ser. No. 62/520,856, titled "DEVICES AND METHODS FOR TREATING SUBJECTS," filed on Jun. 16, 2017, and to U.S. Provisional Application Ser. No. 62/555,128, titled "DEVICES AND METHODS FOR TREATING SUBJECTS," filed on Sep. 7, 2017. Each of these applications is herein incorporated by reference in its entirety for all purposes.

BACKGROUND OF THE INVENTION

1. Field of the Invention

The invention relates to devices and methods for providing irradiation to a subject.

2. Background

The delivery of light can be used to modulate the level of pathogens in a subject, for example, in a burn, and to modulate healing.

SUMMARY

Devices and methods described herein can be configured as a flexible (body conforming) bandage and therefore can be placed directly on the skin surface and under the wound dressing or other bandage material or wound healing technology.

Devices and methods described herein provide advantages including: 1) mono- or multispectral based low-level irradiance wound care that can treat skin/wound infections, reduce the bacterial and fungal bio-burden of wounds, including biofilms, and stimulate the healing of acute and chronic skin ulcers and, 2) deployment of a novel wound care illumination system that can provide irradiance via a conformable, wearable bandage or dressing with portable power supply.

Accordingly, in one aspect the invention features a method of treating a subject, the method comprising:
irradiating the subject with light having a wavelength between 380 nm and 500 nm, for example, at 405 nm, at 0.25 to 25 milliWatts/cm$^2$,
wherein the irradiation is for a time sufficient to treat a subject, and wherein treating comprises:
  a) treating a subject at risk for a pathogen infection;
  b) treating a subject having a pathogen infection;
  c) preventing the infection by a pathogen;
  d) reducing the level of a pathogen;
  e) reducing the virulence of a pathogen in the subject, for example, reducing its ability to damage the subject, slowing the growth of the pathogen, or reducing the release of a toxin by the pathogen;
  f) reducing or otherwise ameliorating an unwanted manifestation of infection by a pathogen;
  g) reducing the level or transmission of a transmissible nucleic acid, for example, a plasmid or an RNA, by a pathogen, for example, to a second pathogen; or
  h) modulating, for example, inhibiting, reducing, or degrading the structure or integrity an extracellular matrix;
  i) modulating the microbiome of the subject, for example, at the site of irradiation or at site outside the site of irradiation, for example, reducing one or more members of a polymicrobial community; or
  j) irradiating a site at which a device, for example, a catheter or conductor, enters the subject's body.

In an embodiment, the method further comprises treating a subject at risk for a pathogen infection.

In an embodiment, the method further comprises increasing the porosity of a biofilm, for example, increasing the porosity to a drug, for example, an antibiotic. In an embodiment porosity refers to the ability of an antibiotic drug molecule to pass into or through a biofilm. In embodiments increased porosity increases the ability of an applied antibiotic to come into contact or kill a bacterium.

In an embodiment, the subject has a burn, for example, a burn that is greater than a Grade 1 burn, for example, a superficial first-degree burn of the epidermis, or outer layer of skin.

In an embodiment, the site irradiated comprises entry point of a medical device, for example, the point of entry of a conduit, catheter, PIC line, Hickman catheter.

In an embodiment the light has a wavelength 405 nm+/− 10 nm.

In an embodiment, the light is provided at between 0.25 and 25 milliWatts/cm$^2$.

In an embodiment, the irradiation is administered at a place other than a health care facility, for example, a hospital, clinic, or physician's office, for example, the irradiation is administered after discharge or exit from a health care facility, for example, a hospital, clinic, or physician's office.

In an embodiment, the irradiation is provided by a device comprising a power source, for example, a wearable power source.

In an embodiment, irradiation is provided as a plurality of periods or pulses wherein the pulses are separated by intervening periods when irradiation is not provided, for example, darkness.

In another embodiment, the invention features a method of treating a subject having a burn, the method comprising:
irradiating the subject with light having a wavelength between 380 nm and 500 nm at 0.25 to 25 milliWatts/cm$^2$,
wherein the irradiation is for a time sufficient to prevent infection of the subject by a pathogen reducing the level of a pathogen (for example, in the burn or systemically), or reducing or otherwise ameliorating an unwanted manifestation of infection by a pathogen (for example, in the burn or systemically) in a subject.

In another aspect, the invention features, a device for providing light to the surface of a subject, the device comprising:
  a) an array of a plurality of light emitting modules,
    each module of the plurality being flexibly connected to another module of the plurality, and
    each module of the plurality being capable of emitting light,
  wherein the array is configured to conform to the surface of the subject.

In an embodiment the device comprises b) light or energy source.

In an embodiment the device comprises c) a connector for transmitting current or light from b to a.

In an embodiment two or more modules of the plurality are configured so as to be able to emit light simultaneously. In an embodiment two or more modules of the plurality are configured so as to be able to emit light at different wavelengths, intensities, or at different times.

In an embodiment, the array of modules is flexible, stretchable, or can be molded to a surface.

In an embodiment, the array of modules can be bent to conform to surface or body part of the subject and when bent to a conforming shape retains the conforming shape.

In an embodiment, each module of the plurality is configured to provide light at 0.25 to 25 milliWatts/cm$^2$, for example, at the surface of the subject.

In an embodiment, the device comprises 2 to 400; 3 to 200; 4 to 100; 5 to 50; 10 to 40; or 20 to 30, modules.

In an embodiment, a module, for example, a module with a hexagonal perimeter, has a longest apex to apex distance, or a longest dimension of 22.5 millimeters.

In an embodiment, modules are present in the array having an X axis and a Y axis and the array is at least 1, 3, 10, or 100 modules in length along the X axis and at least 1, 3, 10, or 100 modules in length along the Y axis.

In an embodiment, the device further comprises a sensor.

In an embodiment, the sensor is connected, for example, wirelessly connected, with a processor or computer.

In an embodiment, responsive to a signal from the sensor, the device, or a processor or computer connected thereto, provides a signal, for example, an alert, to another device or a person, for example, the subject or a caregiver.

In an embodiment, the irradiation is provided by a device comprising a battery.

In another aspect, the invention features, a device for providing light to the surface of a subject, comprising:
 (a) an array of a plurality of light emitting modules,
  wherein each module of the plurality is flexibly connected to another module of the plurality; and each module of the plurality comprises
  (i) a light emitting device,
  (ii) an internally reflective layer configured to receive light from the light emitting device,
  (iii) a port for emission of light from the internally reflective layer,
  (iv) a diffusing member, and
  (v) a polygonal perimeter,
  wherein the array,
   (i) is configured to conform to the surface of the subject, and
   (ii) comprises at least 4 modules;
 (b) a light or energy source; and
 (c) a connector for transmitting current or light from (b) to (a).

In an embodiment, each module of the plurality comprises a hexagonal perimeter.

In an embodiment, each module of the plurality is configured to provide light at 0.25 to 25 milliWatts/cm$^2$, for example, at the surface of the subject.

In an embodiment, each module of the plurality is configured to provide light having a wavelength between: 380 nm and 500 nm; 390 nm and 430 nm; and 395 nm and 415 nm.

In another aspect, the method features, a device for treating a subject, the device comprising:
 a wound surface contact layer;
 a rigid-flex circuit layer configured in a gapped-geometric pattern for even distribution of light and flexibility to conform to body surfaces of a wound; and
 a backing layer which, with the wound surface contact layer, is configured to enclose or substantially enclose the rigid-flex circuit layer therein.

In an embodiment, the rigid-flex circuit layer is a gapped-hexagon pattern.

In another aspect, the invention features a device for providing light to the surface of a subject, comprising: (a) an array of a plurality of light emitting modules, wherein (i) the plurality comprises four light emitting modules; (ii) each module of the plurality is flexibly connected to another module of the plurality; (iii) two of the modules of the plurality comprise: (A) a polygonal perimeter having 4, 5, or 6 major sides; (B) a light source; (C) a longest apex-to-apex dimension for a module of 5-50 millimeters; and (optionally) (b) a non-adherent member configured to be adjacent to the subject.

In another aspect, the invention features a device for providing light to the surface of a subject, comprising: (a) an array of a plurality of light emitting modules, wherein (i) the plurality comprises four light emitting modules; (ii) each module of the plurality is flexibly connected to another module of the plurality; (iii) the modules of the plurality each comprise: (A) a polygonal perimeter having 6 major sides; (B) a light emitting diode; (C) an internally reflective member configured to receive light from the light emitting diode, (D) a port for emission of light from the internally reflective member, and (E) a diffusing member. (F) a longest apex-to-apex dimension for a module of 20+/−5 millimeters; and (b) a non-adherent member configured to be adjacent to the subject.

In another aspect, the invention features a method for providing light to a subject comprising: providing light to the surface of a subject with a device, comprising: (a) an array of a plurality of light emitting modules, wherein (i) the plurality comprises four light emitting modules; (ii) each module of the plurality is flexibly connected to another module of the plurality; (iii) two of the modules of the plurality comprise: (A) a polygonal perimeter having 4, 5, or 6 major sides; (B) a light source; (C) a longest apex-to-apex dimension for a module of 5-50 millimeters; and (optionally) (b) a non-adherent member configured to be adjacent to the subject, thereby providing light to the subject.

Devices and methods described here include those directed to a Low-Irradiance Metronomic Biostimulation (LIMB) System. They provide a novel, wearable technology-essentially a "bandage"-. The device can include integrated electronics that can easily be deployed in environments ranging from the battlefield to community wound-healing clinics. In embodiments, the core technology and light delivery method described herein provide two functionalities. First, antimicrobial activity—the device's visible blue irradiation (non-ultraviolet) reduces bioburden and has the potential to manage infections without the need for additional pharmacological interventions. Second, using the same energy delivery portal, visible red and near infrared wavelengths, can be delivered at low-irradiance continuously over extended periods (because the device is wearable), is used to also aid in infection control, while also potentially accelerating the healing of soft-tissue and bone traumatic injuries.

The devices and methods disclosed herein provide a flexible array that can conform closely to the subject's body and provide illumination. The devices and methods disclosed herein minimize the need for removal of bandages and dressings to provide the therapy, which makes the wound site less susceptible to infection since the wound site is not exposed as frequently to open environments that may contain a bacteria, fungus, spore that can cause infection. In embodiments, devices disclosed herein are configured as a flexible bandage or element that can be applied for days/weeks. As a result, the LIMB system can be applied to injured personnel in both ambulatory and inpatient settings throughout Level I-IV trauma centers and significantly reduce the risk of community-acquired and nosocomial infections typically associated with patient handling and transport.

A significant advantage of devices and methods described herein is the avoidance of high-powered light sources that are relatively expensive, and require a specialized medical facility and staff to operate and maintain, requiring patients to make frequent trips to their clinic.

BRIEF DESCRIPTION OF THE DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

FIG. 5 illustrates a fiber optic light guide, used for photodynamic therapy applications.

FIG. 6(a) illustrates a solid body light guide approach for even-illumination phototherapy applications.

FIG. 8 illustrates discrete light guides.

FIG. 11 illustrates flat connections between light guides of an LED and light guide array.

DETAILED DESCRIPTION OF THE INVENTION

Figure 1A:
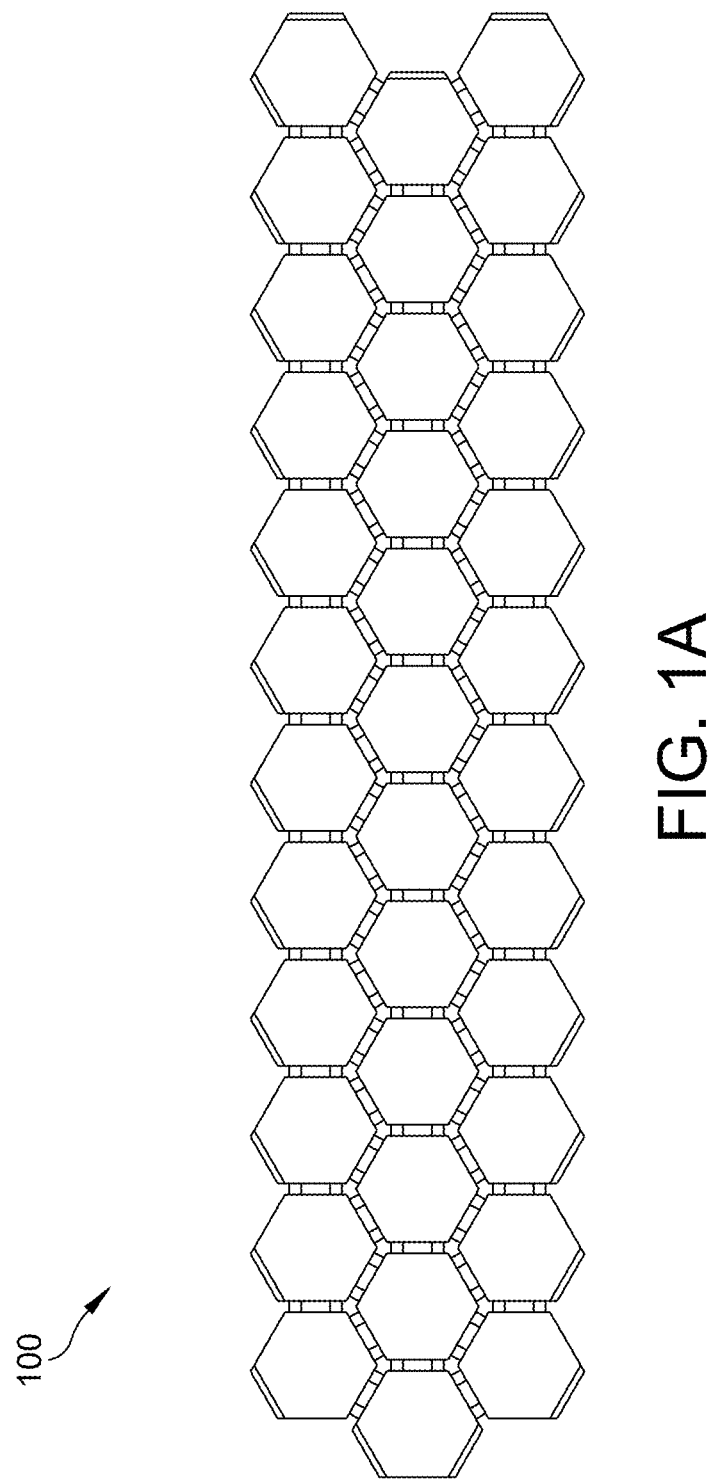
FIG. 1(a) illustrates a top view of a device having a single segment without foam.

Examples of the methods and systems discussed herein are not limited in application to the details of construction and the arrangement of components set forth in the following description or illustrated in the accompanying drawings. The methods and systems are capable of implementation in other embodiments and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are no intended to limit the presently disclosed systems or methods, their components, acts, or elements. The use herein of "including," "comprising," "having," "containing," "involving," and variations thereof is meant to encompass the items listed thereafter and equivalents thereof as well as additional items.

References to "or" may be construed as inclusive so that any terms described using "or" may indicate any of a single, more than one, and all of the described terms. In addition, in the event of inconsistent usages of terms between this document and documents incorporated herein by reference, the term usage in the incorporated features is supplementary to that of this document; for irreconcilable differences, the term usage in this document controls.

Definitions

A polygonal perimeter, as that term is used herein, refers to a shape having a perimeter with at least three sides, for example, at least three major sides. In an embodiment, each of the major perimeter sides is longer than any minor perimeter side present. In an embodiment, a major side is straight or linear but in embodiments it can include irregularities, or features formed by connection to another element, for example, a light emitter. In an embodiment, each major perimeter side differs in length from the other minor perimeter sides by no more than 50, 40, 30, 20, 10, or 5%. In the case of a regular polygonal major perimeter sides are of equal length and the apices of equal angle. A polygonal perimeter be made up of a single unit or more than one segment, for example, a regular hexagonal perimeter can be formed by two half regular hexagonal perimeters.

A hexagonal perimeter, as that term is used herein, refers to a shape having a perimeter with six major sides. Each of the major perimeter sides is longer than any minor perimeter side present. In an embodiment, a major side is straight or linear but in embodiments it can have irregularities, or features formed by connection to another element, for example, a light emitter. In an embodiment, each major perimeter side differs in length from the other minor perimeter sides by no more than 50, 40, 30, 20, 10, or 5%. In an embodiment, a hexagonal perimeter has six perimeter sides and six apices. In the case of a regular hexagonal perimeter there are six major perimeter sides of equal length, six apices, and no minor perimeter sides. In an embodiment, a hexagonal perimeter has six major perimeter sides and one or more minor perimeter sides. For example, one apex of a hexagonal perimeter is replaced with a minor perimeter side, which can be visualized, for example, as a regular hexagon with one apex clipped off (and replaced by a minor perimeter side and two apices. A hexagonal perimeter be made up of a single element or more than one elements, for example, a regular hexagonal perimeter can be formed by two half regular hexagonal perimeters.

A triangular perimeter, as that term is used herein, has three major perimeter sides but is otherwise analogous to a hexagonal perimeter. Generally, a polygonal perimeter can have X major sides, for example, with X equal to 3, 4, 5, 7, 8, 9, 10, 11 or 12, with other parameters analogous to those of a hexagonal perimeter.

Fluence, or total fluence, as those terms are used herein, refer to a stream of particles or photons crossing a unit area, usually represented in particles per second.

Irradiance, as that term is used herein, refers to the radiant flux (power) received by a surface per unit area. The SI unit of irradiance is the watt per square meter ($W/m^2$), or Jules/$cm^2$sec.

Burn categories, as used herein, are defined as follows:

First-degree or Grade 1 (superficial) burn, as that term is referred to herein, is a burn that affects only the epidermis, or outer layer of skin. The burn site is red, painful, dry, and with no blisters. Mild sunburn is an example. Long-term tissue damage is rare and usually consists of an increase or decrease in the skin color;

Second-degree or Grade 2 (partial thickness) burns, as that term is referred to herein, is a burn that involves the epidermis and part of the dermis layer of skin. The burn site appears red, blistered, and may be swollen and painful;

Third-degree or Grade 3 (full thickness) burn, as that term is referred to herein, is a burn that destroys the epidermis and dermis and may go into the subcutaneous tissue. The burn site may appear white or charred; and Fourth-degree or Grade 4 burns, as that term is referred to herein, is a burn that damages the underlying bones, muscles, and tendons. There is no sensation in the area since the nerve endings are destroyed.

Subject, as that term is used herein, refers to a human or a non-human animal. Exemplary non-human animals include dogs, cats, monkeys, rodents, and domestic animals, for example, horses, cows, pigs, goats, and oxen.

Symmetry value, as used herein, relates to the relative duration of periods of irradiation and intervening periods.

Symmetry value can be determined over a single cycle of one period of irradiation and one intervening period or over a plurality of cycles. Symmetry value is expressed as x:y, wherein x is the duration of period(s) of illumination and y is the duration of intervening period(s). A symmetry value of 50:50 means that the duration of the period(s) irradiation is equal to the duration of the intervening period(s). A symmetry value of 10:100 means that the duration of the period(s) irradiation is equal to one tenth the duration of the intervening period(s). The symmetry value can remain constant over a treatment or can change. An increase in symmetry value means a relative increase in the duration of the irradiation period(s) and a decrease in symmetry value means a relative decrease in the duration of irradiation period(s). A pulse or period of illumination can have any of a variety of wave forms, for example, a square wave or a sinusoidal wave.

Overview

Devices and methods described herein can be configured as a flexible (body conforming) bandage and therefore can be placed directly on the skin surface and under the wound dressing or other bandage material or wound healing technology, for example, vacuum-dressing for continuous 24-hr/7-day-a-week treatment.

Devices and methods described herein provide advantages to current wound care phototherapy illumination technologies including: 1) multispectral-based continuous low-level irradiance wound care that can treat skin/wound infections, reduce the bacterial and fungal bio-burden of wounds, including biofilms, and stimulate the healing of acute and chronic skin ulcers and, 2) deployment of a novel wound care illumination system that can provide the continuous low-level irradiance via a conformable, wearable bandage or dressing with portable power supply.

Devices and methods described herein comprise a flexible light-emitting bandage or element that is highly-conformable to body contours and provides extended periods of illumination in an inpatient or ambulatory setting. In embodiments, the core technology is engineered for wound care healing and provides one or both of two functionalities that are principle to continuous low-level irradiance wound care. First, the device can emit low-level short wavelength illumination such as blue light (405 nm) or short-duration pulses of UV-B (280-315 nm) or UV-C (315-400 nm) to reduce bio-burden to manage/avoid infection. Second, the device, using the same light delivery portal as the short wavelength source can deliver a combination of visible and near infrared wavelengths shown to accelerate wound healing. Other embodiments include two separate bandages or devices; one focused on antimicrobial therapy (reducing bio-burden) and another focused on wound healing.

In an embodiment wound care light delivery devices (or illumination sources) have integrated into a bandage that can be placed beneath a compression dressing and enabled for inpatient or ambulatory (including home-based) continuous low-irradiance therapy. This device can aid acute wounds but can also provide significant clinical benefit to chronic wounds by allowing a chronic wound to reduce bacterial bio-burden without the use of antibiotics. Additional benefits of this system are that it allows illumination therapy to be administered continuously for extended periods of time in the comfort of the patient's home, and among seniors, who are often poly-pharmacy, this would 1) reduce the untoward effects of oral antibiotics, 2) avoid drug-drug interactions, 3) provide a means to stimulate healing of chronic wounds and 4) avoid the need for frequent travel to facilities to receive care.

An array of light emitting modules can be configured for coupling to another array. Thus, an end user can select from a plurality of arrays for combination for a particular indication or subject. For example, 2, 3, 4, 5 or more arrays can be coupled. The array is configured to have a bend radiance that allows close adherence to the curvature of the surface being treated. In some embodiments, in has a bend radius of 5 mm.

Methods and devices described herein can treat subjects having a biofilm, for example, to kill pathogens that might otherwise be protected from a therapy by a biofilm. Patients with skin-related infections (acute skin wounds, chronic skin ulcers and patients at high risk for developing skin ulcer, for example, diabetics) can be treated. Because the technology prevents biofilm formation, beneficial results may be achieved in connection with subjects of lost barrier, such as burn patients, to prevent the formation of biofilm. In the prevention of biofilm formation, the technology can be used instead of antibiotics. In the setting of a burn patient with a dirty wound, this technology can be used with a systemic antibiotic.

Methods and devices described herein can be used to treat immunocompromised subjects. In an embodiment a method or device described herein can be used to treat a subject having hepatic impairment or renal impairment, for example, hepatic or renal impairment associated with or due to the use of a 3rd or 4th generation antibiotic.

Wavelengths of Light

Biostimulation: An Overview

Photobiomodulation, also referred to as, "biostimulation," as that term is used herein, refers to the process of illuminating tissues with a specific wavelength of light at a low intensity and with low power over extended periods of time. When using the appropriate dosages, wavelengths, and intensities, the applications of biostimulation provide patients with an effective and safe method of managing infection rates while promoting skin, soft tissue, and bone regeneration. Specific wavelengths within the visible blue (400-470 nm), visible red (620-700) and infrared (700-1000 nm) spectra are microbiocidal, accelerate wound healing, and can be used intermittently or continuously for extended periods of time without engendering drug resistance.

Short Wavelength Biostimulation:

There is a significant body of evidence that has evaluated the use of biostimulation within the ultraviolet (UV) and visible blue wavelengths for their microbiocidal effects on a variety of multiple drug resistant organisms (MDROs). UV biostimulation (100-400 nm) is a commonly-used sterilization technique in clinical laboratories and healthcare settings, and has been validated in multiple studies for its capabilities to sterilize wound surfaces. Prophylactic UV-C (200-280 nm) light treatment can be used for infections developing in highly-contaminated superficial cutaneous mouse wounds contaminated with *Pseudomonas aeruginosa* and methicillin-resistant *Staphylococcus aureus* (MRSA). For both bacterial infections, UV-C light significantly reduced the bacterial burden in comparison to untreated wounds, while also increasing the survival rate of *P. aeruginosa*-infected mice (58%) and the wound-healing rate of MRSA-infected mice (31%). Despite its bactericidal properties, there is a degree of collateral damage associated with extended exposure to short-wavelength UV biostimulation, such as carcinogenicity and impaired wound healing.

Due to UV light's carcinogenic nature and ability to cause direct damage to host cells that inhibits wound healing, administration of biostimulation using wavelengths within the visible blue light (400-470 nm) spectrum has been proven to be efficacious in both its bactericidal effects in addition to its wound healing capabilities. Furthermore, based upon its mechanism of action, blue light biostimulation obviates the collateral damage commonly associated with UV light exposure and is much less detrimental to human cells. The antimicrobial mechanism of visible blue biostimulation involves the photoexcitation of endogenous porphyrins within pathogens, and, subsequently, the generation of reactive oxygen species (ROS), which are in effect toxic to bacterial cells and biofilms. Exposure to a 405 nm LED array has a phototoxic effect on a variety of bacteria that are highly prevalent in community-acquired and nosocomial infections, including Gram-positive bacteria: MRSA, *Staphylococcus epidermidis, Streptococcus pyogenes, Clostridium perfringens*, and Gram-negative bacteria: *Acinetobacter baumannii, Pseudomonas aeruginosa, Escherichia coli, Proteus vulgaris* and *Klebsiella pneumonia*. Visible blue light (415 nm+/−10 nm) therapy can be used for eliminating community-acquired MRSA infection in skin abrasions of mice, and has been shown to produce a $2.0\text{-log}_{10}$ (99.0%) bacterial inactivation in abrasions after one dose of light administered over 30 minutes. On top of its bactericidal effects, further evidence indicates that visible blue biostimulation enables a significant reduction of biofilm formation both prophylactically and in response to trauma. 415 nm blue light has antimicrobial properties on biofilms of *Acinetobacter baummanii*.

Proliferative Effects of Long-Wavelength Biostimulation:

Biostimulation using longer wavelengths in both the visible red (620-700 nm) and near-infrared (NIR; 700-1000 nm) range significantly accelerates tissue repair in bone, skin, muscle and nerves, as well as stimulating both angiogenesis and collagen deposition. Furthermore, it has been documented to regulate gene expression that directly promotes cell proliferation by suppression of apoptosis, in addition to regulating the expression of genes related to cell migration and remodeling, DNA synthesis and repair, and extracellular matrix deposition. Among published studies, the most prevalently cited indication for biostimulation is directed towards its capabilities of accelerating granulation and re-epithelialization of acute and chronic skin wounds. In patients with diabetic foot ulcers, biostimulation accelerated the healing process of chronic diabetic foot ulcers, and biostimulation using visible red wavelengths shortened the time period needed to achieve complete healing by as much as 21 days, compared to control trials receiving traditional standards of care. The combination of visible red and IR wavelength biostimulation on diabetic leg ulcer patients results in rapid granulation and healing of diabetic ulcers that failed to respond to other forms of treatment.

In addition to rapid skin regeneration, biostimulation accelerates bone healing, as well as restoring the functional recovery of nerve and muscle tissue following traumatic injury. Infrared (830 nm) biostimulation can be used to treat closed bone fractures in the human wrist and hand. NIR (808 nm) biostimulation promotes the recovery and nerve regeneration of post-traumatic nerve injuries on a sciatic nerve crush rat injury model. NIR (808 nm) biostimulation promotes muscle regeneration and vascular perfusion in Wistar rats that underwent cryolesion of the tibialis anterior muscle. Biostimulation significantly reduces the lesion percentage area in the injured muscle, and increases mRNA levels of the transcription factors MyoD and myogenin and the pro-angiogenic vascular endothelial growth factor. Moreover, biostimulation decreases the expression of the profibrotic transforming growth factor TGF-β mRNA and reduced type I collagen deposition.

Multispectral Biostimulation:

The bactericidal properties of the lower wavelengths with the soft tissue and bone regeneration properties of the longer wavelengths can be combined to provide more favorable therapeutic outcomes than monochromatic biostimulation.

In embodiments, devices and methods described herein provide these wavelengths at an optimal dosage and: 1) ensure a conducive wound environment, 2) provide biostimulation to stimulate healing bone and soft tissue regeneration of devascularized tissues of as a result of trauma-induced and combat-related injuries, and 3) reduce the untoward effects of oral and intravenous antibiotics.

Low-Irradiance Metronomic Biostimulation (LIMB) System:

There is a wide variety of illumination devices that provide biostimulation in use currently in both clinical trials and commercially; primarily these are classified as medical lasers or LED medical lasers. The medical lasers in current use range significantly from large desktop-computer sized lasers to handheld LED devices. Nonetheless, clinical trials are typically similar in that the subjects receiving biostimulation are exposed to monochromatic (one wavelength) light at high irradiances (>100 mW/cm$^2$) over a short duration of 10-20 minutes, ultimately requiring subjects to frequently travel to treatment clinics to receive therapy.

Embodiments of the present disclosure are directed to a Low-Irradiance Metronomic Biostimulation (LIMB) System: a novel, wearable technology—essentially a "bandage"—with integrated electronics that can easily be deployed in environments ranging from the battlefield to community wound-healing clinics. In embodiments, the core technology and light delivery method described herein provide two functionalities. First, antimicrobial activity—the device's visible blue irradiation (non-ultraviolet) reduces bio-burden and has the potential to manage infections without the need for additional pharmacological interventions. Second, using the same energy delivery portal, visible-red and near-infrared wavelengths can be delivered at low-irradiance continuously over extended periods (because the device is wearable), and is used to also aid in infection control, while also potentially accelerating the healing of soft-tissue and bone traumatic injuries.

An additional factor of the LIMB system is that it also addresses the limitations of prior irradiance-based technologies that have been used in infection control and wound management. While current technologies require removal of bandages and dressings to provide the therapy, which makes the wound site more susceptible to infection, embodiments of the LIMB system are configured as a flexible bandage that can be applied for days/weeks. As a result, the LIMB system can be applied to injured personnel in both ambulatory and inpatient settings throughout Level I-IV trauma centers and could significantly eliminate the risk of community-acquired and nosocomial infections typically associated with patient handling and transport.

Pathogens and Irradiation

In addition to enabling biostimulation application into acute care settings, devices and methods described herein also address the limitations of prior irradiance-based technologies that have been used in wound management and bone healing. For example, prior irradiance based technologies are typically high-irradiance systems that are relatively expensive, require a specialized medical facility and staff to operate and maintain, and require patients to make frequent trips to their clinic to receive a light-based treatment. Current standard methods of high-irradiance systems provide treatment light doses over short durations ranging from 60 seconds to 30 minutes using high-powered lasers or lamps, which emit high-irradiance light from 50 mW/cm$^2$ to 1000 mW/cm$^2$. One significant advantage of certain devices and methods described herein is the avoidance of high-irradiance light sources and the ability to deliver energy at a low irradiance (within the range of microwatts to milliwatts per square centimeter [μW/cm$^2$, mW/cm$^2$], with precision dosimetry (uniform light across a treatment surface area). In order to deliver the same total fluence as high-irradiance systems, the low-irradiance delivery device can remain in contact with the wound bed continuously for extended periods of time. Devices and methods described herein include a flexible light-emitting bandage or element that is highly-conformable to body contours and provides extended periods of illumination as a wearable, battery-powered device. The device can be fabricated as a bandage, cast, or brace, or be embedded within a prosthesis to decontaminate wounds, treat localized infected ulcers, and stimulate wound healing.

In an embodiment a wearable medical device is provided that can deliver therapy to skin wounds continuously and/or intermittently for days at a time using low irradiance. In embodiments the device has the ability to kill bacteria including multidrug resistant organisms (MDROs) without the use of antibiotics.

The first series of procedures conducted to validate the antimicrobial capabilities of the LIMB system were designed to determine if prior literature on visible blue biostimulation dosing for sterilization administered over acute periods (seconds to minutes at 40-100 mW/cm$^2$) would effectively translate to a low-irradiance (up to 24 hours at 0.2-10 mW/cm$^2$) delivery method that could still achieve a minimum 2.0 log (99.0%) bacterial load reduction. Validation was conducted in two separate phases. Within Phase 1, the antimicrobial properties of the LIMB system were first evaluated on clinical isolates of methicillin-resistant *Staphylococcus aureus* (MRSA) by subjecting each culture to identical fluences of light (75 J/cm$^2$), but the total irradiance (mW/cm$^2$) and time of delivery were altered. Following this period, the LIMB system was evaluated at varying irradiances delivered continuously over 24 hours to determine if there was a minimum irradiance at which a >99.0% bacterial load reduction could still be achieved.

Devices and methods described herein inhibit the colonization of MDROs to form biofilms in acute and chronic wounds.

The inhibition of colonization of MDROs and the effect on the formation of microbial biofilms is evaluated in Example 2.

Devices and methods described herein have the ability to reduce and eliminate biofilms that have already formed in wounds.

Effects on *P. aeruginosa* biofilms are evaluated in Example 3.

In an embodiment a device disclosed herein can physically disrupt the integrity of MDRO biofilms, and subsequently allow for antimicrobials and disinfectants to penetrate through the biofilm. In doing so, the device can provide an additive and/or synergistic antimicrobial effect when used in conjunction with other pharmacological agents.

Due to evidence which documents the role of biofilms and their enhanced virulence factors, particularly due to their nearly-1,000-fold increase in tolerance of antibiotics, disinfectants, and antiseptics when compared to their planktonic counterparts, the potential of using adjuvant pharmacological agents in conjunction to the LIMB system as an antimicrobial combination therapy was evaluated. Further evaluation of the effect on biofilms is provided in Example 4.

By affecting the bacterial cellular machinery the energy admitted from the device can inactivate plasmids and small molecules that confer bacterial resistance to specific forms of antibiotics. For example, by using the device on a chronic wound that is infected with MRSA, the device renders the bacteria sensitive to penicillin-type antibiotics, thus enabling methicillin and other early generation penicillin drugs to effectively kill the bacteria.

Light Sources

Current illumination systems for phototherapy (photorejuvenation, actinic keratosis, psoriasis, photodynamic therapy, etc.) typically require removal of bandages and dressings to provide the therapy under fixed illumination systems. The typical light output of these systems (once contacting the skin surface) is >10 mW/cm$^2$ and are usually delivered at high irradiances (mW/cm$^2$) over 5-30 minutes.

As they pertain to phototherapy, and specifically wound care, prior art devices and methods disclosed herein DO place undue temporal and spatial limits on the duration of therapy. In embodiments of devices and methods described herein, subjects do not need to travel to, and have the therapy conducted in, a hospital or other facility.

Devices and methods described herein avoid, from a biological perspective, shortcomings of fixed phototherapy illumination units which can have negative side effects on wound treatment. Exposing the patient wounds on a frequent basis opens the wound to potential pathogen involvement, inducing greater risk of infection. Additionally, although initial light exposure may cause the cell death of some bacteria, the biggest issue is that once treatment is complete, the bacteria and pathogen are back to growing, replicating every 20 minutes. Hence, although an infection or wound may have a beneficial impact from phototherapy for the duration of therapy (during light delivery), the infection or wound healing process can be impaired immediately after initial treatment, thereby effectively making the treatment inconsequential.

The following is a list of prior art in the field of light delivery products and technologies for medical products, specifically for phototherapy and for wound care.

Direct and Focused Illumination Systems

In the medical device field there are numerous methods to deliver light to perform a medical procedure, but the two most common methods are direct and focused illumination. Direct illumination occurs with a bare or diffused light source placed a distance of several centimeters to meters from the patient. Direct illumination devices are rarely attached to the patient. In general, the patient is required to position themselves to the illumination source. Examples of light delivery devices that fall within this category include conventional phototherapy units, such as the standard light box (and hand/foot unit) that emit UV-A, UV-B or narrow-band UV-B light. Phototherapy units are used primarily for the treatment of inflammatory skin diseases such as psoriasis. The units are also used in conjunction with orally or topically administered psoralens that photoactivate with UV-A light in the treatment of severe psoriasis and extensive vitilligo. This treatment is known as PUVA (psoralen UV-A) therapy. For systemic diseases such as cutaneous lymphoma, graft versus host disease, and systemic sclerosis, extracorporeal photophoresis is performed where the patient ingests the psoralen and the blood is exposed to the UV-A light outside the body and then re-infused into the patient. The DUSA (blue visible light) and Galderma-Metvix (red visible light) systems are used for the treatment of actinic keratoses (pre-malignant skin growths) and superficial basal cell carcinomas. They work via topical aminolevulinic acid (DUSA) and methyl-aminolevulinic acid PDT.

Focused illumination, both internal and external to the patient treatment site, requires illumination that has an optical system to direct light from the illumination device to specific areas onto the patient, typically in a controlled beam shape and beam intensity. In many cases the optical system is composed of one or more optical fibers that use total internal reflection to collect light at one end of the fiber, transmit the light, and exit with a specific numeric aperture at the other end. Typically, this approach requires larger fibers or an array of large fibers to illuminate large areas (>5 mm). Illuminating more than a single fiber requires sophisticated coupling of the light into the fibers. This coupling is usually inefficient and can have very low coupling efficiency (<10% efficiency). Similar to direct illumination, the focused illumination approaches are rarely done in which a patient wears a device.

For FDA-approved Photodynamic Therapy (PDT) indications, there are numerous light illumination devices meeting the direct and focused illumination schemes. For example, for Barrett's esophageal cancer treated with PDT, a focused illumination system is implemented using a fiber optic cable attached to an FDA-approved laser system such as the Angio Dynamics PDT 630 nm laser. Alternatively, a direct illumination approach to PDT for actinic keratosis is done using similar devices such as DUSA's Blue-Light Phototherapy Lamp or Galderma's Aktilite which is also used for basal cell carcinoma skin cancer.

There are also a few direct and focused illumination devices specifically used in wound care healing using light. For example, there is the Biolight BCD 650. The device is hand-held and is only suggested for light delivery over several minutes.

Portable and Wearable Illumination Systems

As can be seen from the examples and from existing illumination devices, many are not portable (for example, because they are difficult to physically move), and in general this means the illumination device cannot be worn or used by the patient during Activities of Daily Living (ADLs). In some embodiments, devices disclosed herein are portable and wearable.

Devices

Embodiments of the device include a light-emitting bandage or element for the delivery of 405 nm (+/−10 nm) light at low irradiance (<10 mW/cm$^2$) over a 24-72 hr period. In one embodiment, the system is configured to include a wound dressing and a power pack.

Wound Dressing

In one embodiment, the wound dressing includes:
1. a wound surface contact layer (in embodiments it is hydrophobic and can, for example: protect the patient from the internal circuitry of the dressing; in embodiments it is hydrophilic and can, for example, collect exudate from the wound),
2. a rigid-flex circuit layer which is constructed in a gapped-hexagon pattern for even distribution of light and flexibility to conform to body surfaces of a wound, and
3. a backing layer which, with the wound surface contact layer, (in embodiments it is hydrophobic, and can for example, form a seal protecting and enclosing the circuitry within) encloses the circuitry within.

Figure 1B:
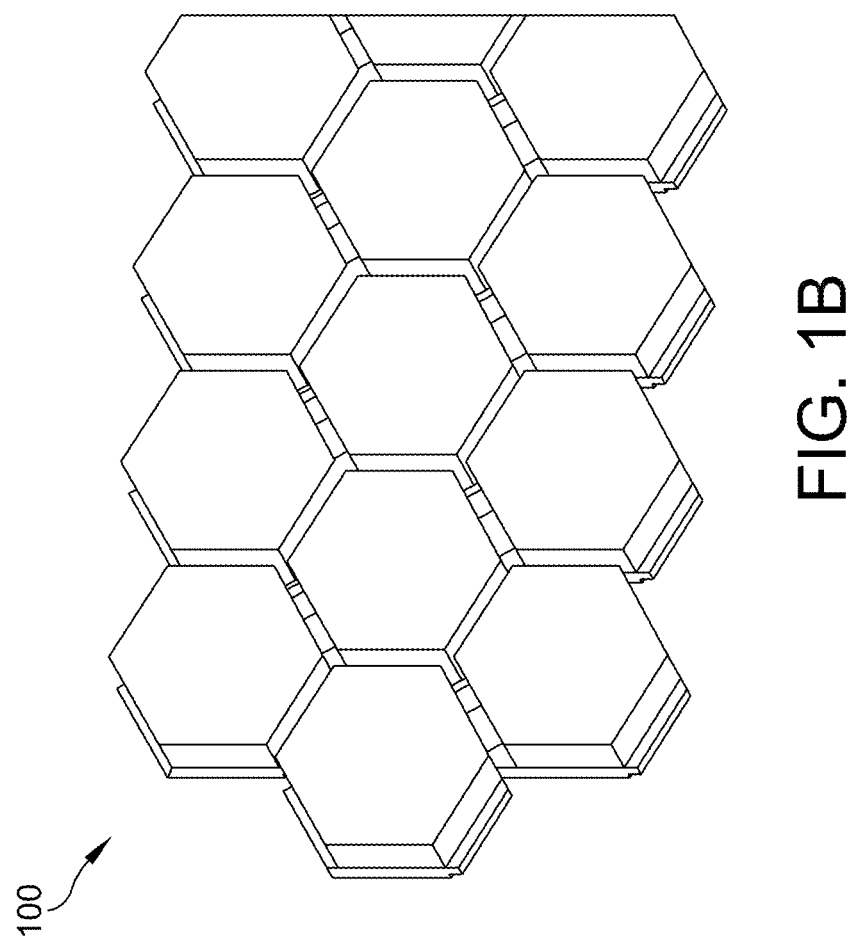
FIG. 1(b) illustrates a perspective view of the device having a single segment without foam.

In and embodiment the wound dressing is 5 cm×30 cm and includes a layout illustrated in FIGS. 1A and 1B. FIG. 1A illustrates a normal to top view of a device 100 having a single segment without foam. FIG. 1B illustrates an angled top view of the device 100 having a single segment without foam. Over each hexagon area on the PCB (composed of a white reflective PET or polyimide) illustrated in FIGS. 1A and 1B, resides a hexagon light guide (22.5 mm in the largest diagonal, 11.25 mm along an edge).

Figure 2:
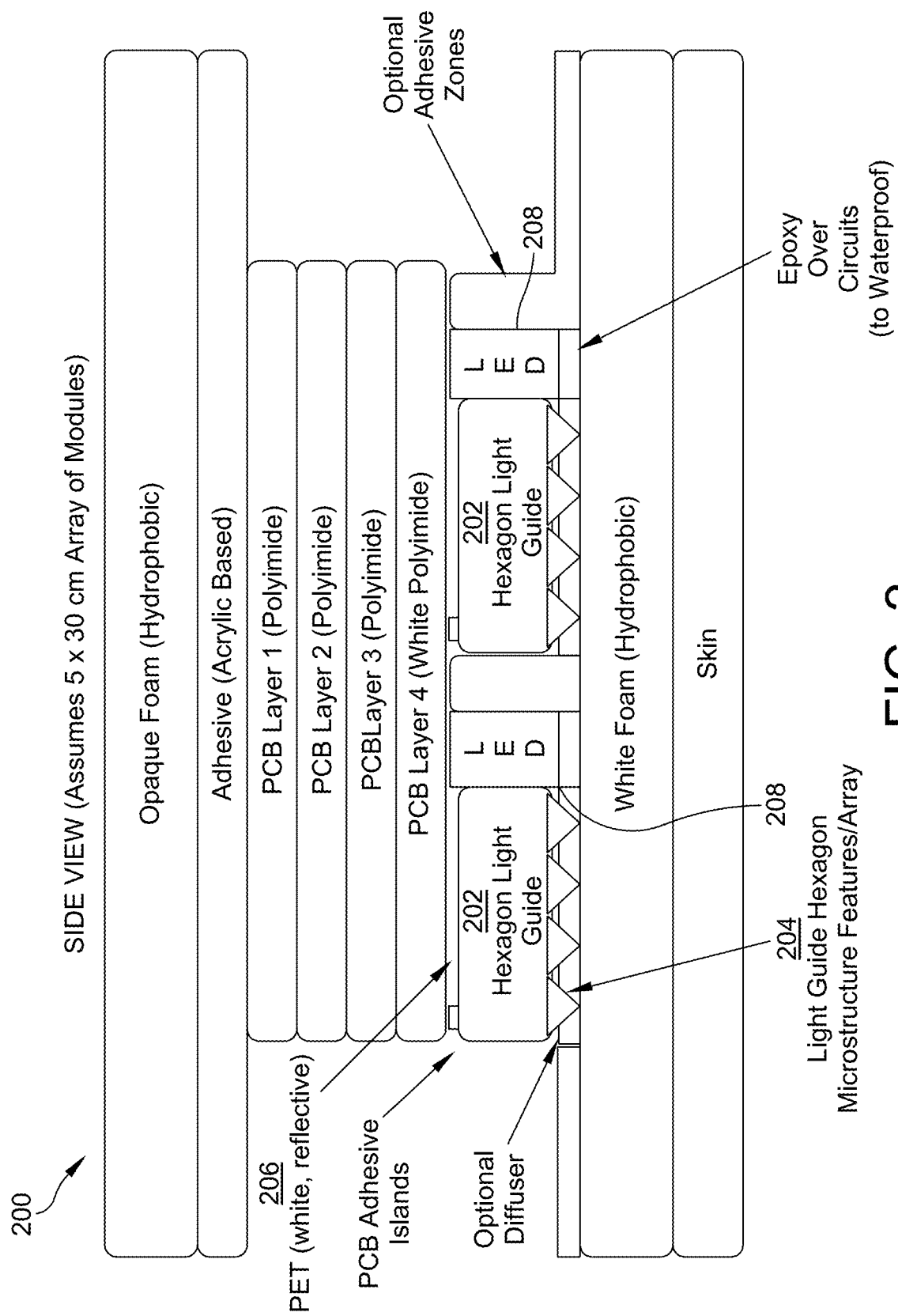
FIG. 2 illustrates a side view of a hexagon light guide and electronics layout.
Figure 3:
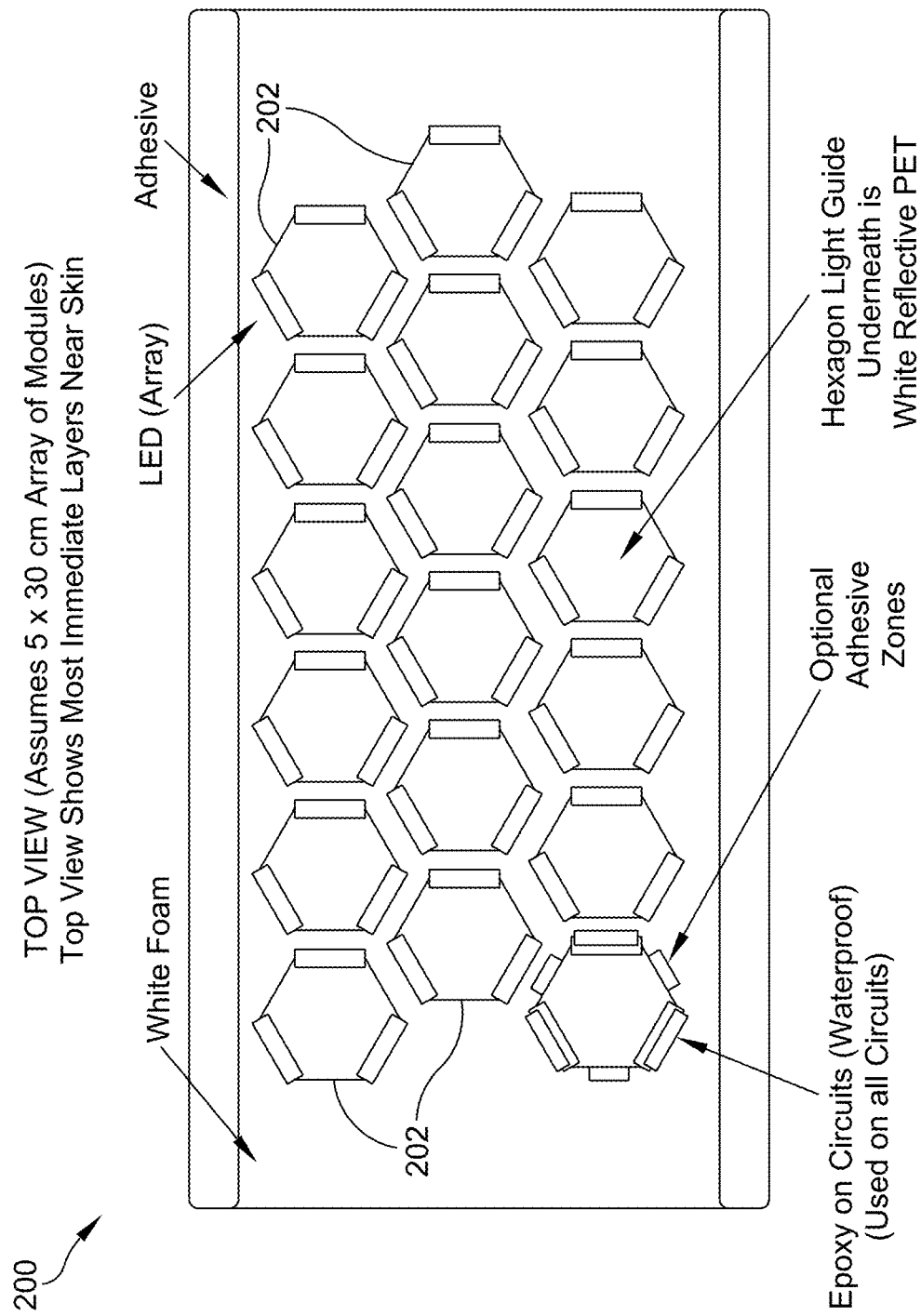
FIG. 3 illustrates a top view of the hexagon light guide and electronics layout.

For example, FIG. 2 illustrates a side view of a hexagon light guide and electronics layout 200. FIG. 3 illustrates a top view of the hexagon light guide and electronics layout 200. The hexagon light guide and electronics layout 200 includes hexagon light guides 202.

The hexagon light guides 202 illustrated in FIGS. 2 and 3 are composed of a 0.5 mm medical grade PMMA (Evonik PMMA LJ19673/21/1 0.5 mm thick material). On the bottom surface of the hexagon light guides 202, the surface is flat. On the top, a pattern of micro-dots 204 is layered to evenly (uniformly) illuminate the entire light guide surface. The pattern accounts not only for side-emitting LEDs which illuminate the hexagon but accounts for other light diffusion surfaces that provide uniformity including a diffuser (if needed) and the hydrophobic/hydrophilic foams described above. FIG. 2 has an internal reflective surface feature label which represents the pattern of micro-dots and other diffusion surfaces.

A reflective PET layer 206 (which could be combined with other diffuser, prismatic, or polarizing materials) is used as a means to create an effect of total internal reflection (TIR), which allows the light emitted by side-emitting LEDs 208 respectively attached to a side of each of the hexagon light guides 202 to internally reflect light from one side of the respective hexagon light guide 202 to the other side.

The reflective PET layer 206 has a higher index of refraction than the material of each hexagon light guide 202 and the side-emitting light entrance of a given hexagon edge allows "most" of the light to go from a low index of refraction environment (for example, air) into the hexagon material above the critical angle needed for TIR. The spacing of the micro-dots 204 on the top (the light emission surface facing the treatment site) or bottom of the light guide creates a mechanism for the light that is undergoing TIR to bounce out of the hexagon light emission side because the light angle changes enough to meet the boundary condition for refraction (out of the hexagon light guide surface) rather than reflection and continuing via TIR down the remainder of each of the hexagon light guides 202. The spacing of the micro-dots 204 is generated to make sure that light leaks (breaks the boundary condition) uniformity across the hexagon light emission surface.

In certain embodiments, a micro-array pattern of micro-dots can be placed on the bottom of the hexagon (facing the reflective white PET, residing below the non-light emission surface side of the hexagon), to generate uniform light emission from the top of the hexagon towards the treatment site. However, when one presses down on the hexagon light guides 202, a hot spot is created, because the design assumes there is a small air-gap between the light guide micro-dots 204 and the PET 206. When the unit is pressed upon the air gap disappears and more light exits the hexagon light guides 202 where there is no air gap. To avoid this problem, the micro-dot was placed on the top of the hexagon light guides 202—facing the PET 206/diffuser. This approach or micro-dot pattern assumes the air gap is completely removed.

In certain embodiments, foams with adhesive coatings on top of the light-emitting surface of the light guide can cause light to bounce out of the light guide closest to the LED input in the light guide. A suitable micro-dot pattern to avoid the light existence from the adhesive has not been successfully developed. The adhesive generates an optical environment that reduces TIR a short distance from the LED input. The current solution is to apply foams, diffusers, polarizers, etc. without any adhesive that may make contact with the light guide light-emitting surface. However, adhesive on the foam, diffuser, and polarizer on the side opposite of the light guide contact side is permissible and can work with a given micro-dot pattern. The adhesive could consist of an acrylic adhesive, silicon adhesive, or a skin-friendly or trauma-friendly adhesive.

Figure 4:
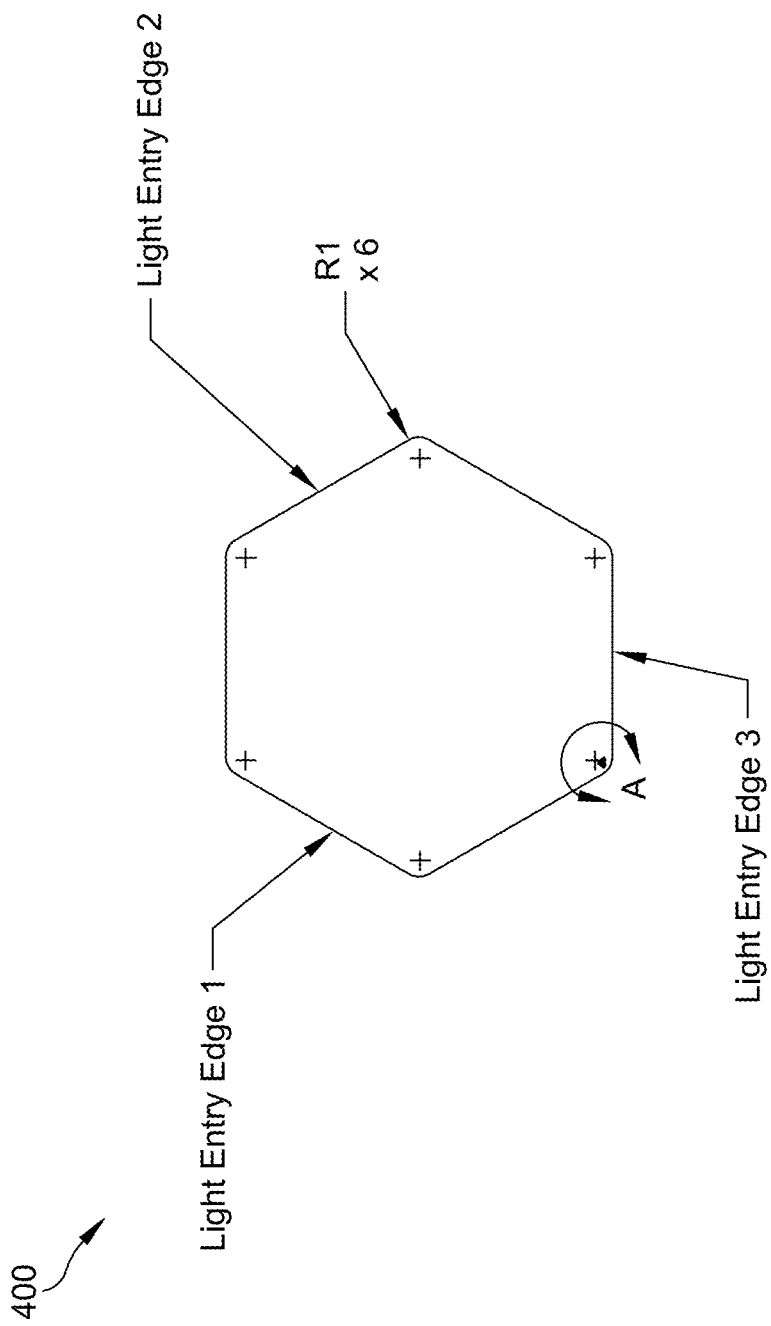
FIG. 4 illustrates a view of side-emitting LED in relation to a polygonal light guide.

To get light into the hexagon light guides, the primary mechanism is to use side-emitting LEDs from TechLED (Marubeni). The side-emitting LEDs commonly used for wound care applications emit 405 nm light. In certain embodiments, three edges illuminate the hexagon, as illustrated in FIG. 4. FIG. 4 illustrates a view of side-emitting LED 400 placement. Given the size of the current hexagon, three side-emitting LEDs can reside on each of the three edges (total of nine side-emitting LEDs per hexagon). In future versions, for a given edge, each LED in the array could emit different wavelengths for different wound healing therapeutic purposes.

The backing layer composed of a foam can have adhesive on either side, as discussed below with respect to FIG. 2. This adhesive layer would allow the PCB components (but not the light emission surfaces of any light guide) to stick to the foam backing. It would also allow foam (without any adhesive) which is on top of the light-emitting surface of the light guide to seal to the backing layer. The backing layer could contain other foam, diffusers, polarizers, or optical materials (transparent, semi-transparent, or opaque).

The PCB components, such as the LED drivers, LEDs, and other parts can be domed with epoxy to make the parts/circuits water proof. The following PCB can include thermistors to monitor temperature within the wound dressing. Data from the thermistors can be sent back to the power pack by a connector cable.

In an embodiment, a plurality, for example, three, of these wound dressings can be connected to one another and receive power from the power pack by the connector cable. Hence the units are stackable and modular. Multiple dressings (or zones) can be powered through a single connector which goes to the power pack. Multiple data lines from a given dressing can traverse through multiple dressings so as to only require one location to acquire the data rather than multiple ports per dressing.

Table 7 provides a description of an embodiment of a hexagon light guide and electronics layout according to one implementation. For example, the properties described in Table 7 may illustrate properties of an embodiment of the hexagon light guide and electronics layout 200.

TABLE 7

Example hexagon light guide and electronics layout description.

| | |
|---|---|
| LIGHT GUIDE | |
| Type | Side-emitting illumination source, e.g., a Light Emitting Diode (LED) |
| Shape | Polygonal, e.g., hexagon |
| Size | 5 mm to 50 mm in the longest dimension; e.g., 20 mm |
| Thickness | 0.100 mm to 1 mm; e.g., 0.500 mm |
| Bottom Surface (facing PCB) | In contact with PET white reflective material |
| Top Surface (facing treatment site/skin) | Composed of microstructures, microlenses, microdots to direct light out of the light guide based on total internal reflection |
| Microstructure Features | Typically under several hundred microns, <100 um |
| Microstructure Array | Typically non-uniform to allow light to exit equally across the entire surface. Lower density (fewer microstructures) near the side-emitting illumination source. Higher density (more microstructures) near the center of the polygonal shape. Pattern can be linear, or two-dimensional, where two-dimensional patterns typically assume side-emission from multiple input faces and the microstructure pattern emits from each side of illumination to the center of the polygon. |
| PCB | |
| Shape | Polygonal, e.g., hexagon with extra width where LEDs are placed |
| Size | 5 mm to 50 mm in the longest dimension; e.g., 20 mm |
| Thickness | 0.125 mm to 1.6 mm; e.g., 0.8 mm |
| Material of PCB | FR-4 |
| LED | |
| Location | Attached to PCB (defined above) |
| Type | Side-Emitting |
| Size (Footprint) | 2.10 mm width, 0.6 mm height, 1.0 mm length (from lens to back) |
| Size (Lens) | 1.70 mm width, 0.6 mm height, 0.5 mm length |
| Lens/Optic FOV X-Dim (Horizontal) | +/−82 Degrees |
| Lens/Optic FOV Y-Dim (Vertical) | +/−67 Degrees |
| Radiated Power | 20 mW |
| LED ARRAYS | |
| LEDs in an Array | LED Array could be composed of a single LED or multiple LEDs. Number of LEDs on any given side of a hexagon that is 20 mm will be up to 3 LEDs. Spacing between LEDs can be linear or non-linear (linear preferred). Location of array along one side of a hexagon can be symmetric or non-symmetric from center (symmetrically located preferred). |

TABLE 7-continued

Example hexagon light guide and electronics layout description.

| | |
|---|---|
| Array Location | If one side, assume a linear micro structure light guide. In most cases, assume two-dimensional microstructure and LEDs on more than one side of hexagon. Assume an array on three-opposite sides with one wavelength. All six sides of the hexagon could have an LED array. Each side could have the same wavelength LED. 3-opposite sides of the hexagon could have one wavelength while the other 3-opposite sides of the hexagon could have another wavelength. For example, 3-opposite sides of the hexagon could have an LED array that emits 405 nm light and the other 3-opposite sides of the hexagon could have an LED array that emits 680 nm light. |
| LED Array Wavelengths | A single array on any given side of a hexagon could include more than one wavelength. For example, within one array, assume 3 LEDs in the array, could include two 680 nm emitting LEDs and a single 850 nm LED. |
| LED Control | Each LED could be individually controlled. Each LED array could be individually controlled (preferred for multiple wavelength variations), or all LEDs on a single PCB could be controlled (preferred for single wavelength, this is the current process) |

OTHER MATERIALS

| | |
|---|---|
| PET | Reflective, white material laid down on PCB between the LEDs/arrays |
| Conformal Coating | Over electronics and LEDs (but not lenses) to protect parts |
| Adhesive Zones | On PCB to lay down PET and other floating materials |
| Thermally Conductive Heatsink Materials | Manage heat transfer from LEDs and PCB away from skin and out of bandage. Thermally conductive materials include copper, aluminum, other. Surface area key element in reducing heat. Magnets may be used as a mechanism to transfer heat. |
| Outer Dressing: Silicones (Treatment Side) | Patient-contacting side/skin-side material may be optically clear to maximize light throughput while minimizing light output of LED and reducing thermal waste from each LED. Thickness 1 to 2 mm. |
| Outer Dressing: Silicones (Air Side) | In some embodiments, it may be preferable to have a silicone with some heat transfer capability. NuSil provides (a silicone material (MED15-2980P and MED20-2955P) that is thermally conductive. Air side silicone can be opaque, which can aid in reducing any light projecting towards patient/outside observer's visual field. |
| Inner Dressing: Silicone (Interstitial) | Silicone with low durometer (<50) with diffusant. This layer diffuses the LED point source light such that the irradiance measured over the LED is similar to that over the remainder of the hexagon light guide. This layer also acts as a mechanical fixture to keep the hexagon light guide in place in relationship to the LEDs and LED arrays. |
| Silicone over Foam Outer Dressing or Equivalent | Silicone may be implemented as a surface because it can be optically clear, non-adherent, and can be cleaned easily between daily uses. It is also very flexible when it has a durometer between 10 Shore A to 60 Shore A (18-30 Shore A preferable). Also, by encapsulating opto-electronics, the silicone can be ripped off after use and repackaged and re-sterilized to take advantage of the long shelf-life of the opto-electronic parts. Utilizing all silicone parts for the outer dressing along with inner dressing makes it easier/simpler to adhere these materials together with silicone adhesives or with over-molding. |
| Adhesive Zones on Outer Dressing | For burn wounds, no adhesive desired to avoid pulling at tissue that may be healing. For chronic ulcers, like diabetic foot ulcers, potentially desirable to have adhesive. |
| Other Layers | Other layers may include foams (hydrophobic or hydrophilic), polyurethanes, or other medical grade materials that are flexible, durable, light-transmitting (patient contact side), and can aid in fluid management. |
| Preferred fluid management | For burn wounds, silicone encapsulated bandage sits over the top of a hydrogel placed in wound (for example, a hydrogel from Advanced Medical Solutions, Ltd). Hydrogel can be used on dry-wounds. For low-medium-high exudating wounds, optimal dressing in the wound for fluid management is a calcium alginate (for example, a calcium alginate from Advanced Medical Solutions, Ltd), wetted or wet from exudate. |

HEXAGON SYSTEM

| | |
|---|---|
| Single Hexagon Layers (Locally) | Primarily composed of PCB, PET, light guide, LED, localized wire management system, localized interstitial silicone layer, localized silicone patient contacting side, localized thermally conductive material(s), localized thermally conductive silicone |
| Hexagon Layers (Device) | All of the above but full silicone layers, wire management, and thermal conductive layers expanded around all hexagons. |
| Primary Hexagon Light Patch Arrays in Use | 3 × 6 array, lilypad (center hexagon surrounded by 6 outside hexagons). |

TABLE 7-continued

Example hexagon light guide and electronics layout description.

| | |
|---|---|
| Stacking | Instead of larger array sizes, there is the option of stacking the smallest site arrays (i.e. the 3 × 6 array and lilypad) |
| Ideal Hexagon Size | 20 mm in longest dimension. Optimal range 5 mm to 30 mm in longest dimension. |
| Ideal Hexagon Array Sizes | 3 × 6 array, lilypad (for example, FIG. 9), and large blanket (3 ft. × 3 ft. or 1 m × 1 m) |
| Large Blanket Sizes | 50 × 50 hexagon array or an array of stacked 3 × 6 arrays or stacked lilypads |
| Ideal Hexagon Array Size for 5%-to-15% TBSA Burn | 3 × 6 array, lilypad (for example, FIG. 9) |
| Ideal Hexagon Array Size for >15% TBSA | Large blanket (3 ft. × 3 ft. or 1 m × 1 m) |
| Ideal Hexagon Size for Chronic Ulcers (Diabetic Foot and Pressure Ulcers) | 3 × 6 array, lilypad |
| Array of Hexagon Range (when Hexagon Diagonal = 20 mm) | 1 × 1, 3 × 3, 3 × 6, 6 × 6, 3 × 12, 12 × 12, 25 × 25, 50 × 50; specifically 3 × 3, 3 × 6, and 50 × 50 |
| Hexagon Size Range (Based on Diagonal) | 5 mm, 10 mm, 15 mm, 20 mm, 25 mm, 30 mm, 35 mm, 40 mm, 45 mm, 50 mm; specifically 20 mm for flexibility around arm, wrist, leg. 5 mm ideal for smaller extremities like fingers. 50 mm ideal for large flat surfaces like chest, back, or thigh. |
| HEXAGON ARRAY SPACING | |
| Spacing Between Hexagons | Balance between spacing, flexibility, and light coverage. Preferred gap between hexagons is between 0.5 mm to 3.00 mm, with an ideal distance of 1.5 mm to 2.00 mm. |
| Problem of small air gap | When bending hexagons overlap and crash into near neighbors. |
| Problem of large air gap | Light uniformity decreases. |
| WAVELENGTH AND IRRADIANCE | |
| Wavelength Range (Wavelength 1) | 380 nm-430 nm; for example, 405 nm plus/minus 10 nm. Other ranges of interest 425 nm plus/minus 10 nm and 470 nm plus/minus 10 nm. |
| Wavelength Range (Wavelength 2) | 650 nm-700 nm; for example, 675 nm plus/minus 10 nm. Other ranges of interest 625 nm plus/minus 15 nm and 690 nm plus/minus 15 nm |
| Wavelength Range (Wavelength 3) | 830 nm plus/minus 20 nm. Other wavelengths of interest 810 nm plus/minus 20 nm and 850 nm plus/minus 20 nm. |
| Wavelength 1 Irradiance Range | 1 mW/cm2 to 10 mW/cm2; for example, 3 mW/cm2 |
| Wavelength 2 Irradiance Range | 0.3 mW/cm2 to 2 mW/cm2; for example, 0.75 mW/cm2 |
| Wavelength 3 Irradiance Range | 0.3 mW/cm2 to 2 mW/cm2; for example, 0.75 mW/cm2 |
| DURATION OF TREATMENT/WAVELENGTH | |
| Duration of Treatment Wavelength 1 | 24 hours continuously or pulsed. |
| Pulsed Treatment Wavelength 1 | 5 min. on/off, repeat up to 24 hours. If pulsed, vary irradiance by 2x the irradiance of the continuous treatment. In one embodiment, range of pulsing 5 min. on/off up to 30 min. on/off. Asynchronous pulsing is an option (i.e. 10 min. on/5 min. off, repeat). |
| Duration of Treatment Wavelength 2 and 3 | Greater than 6 hours of continuously or pulsed treatment. 12 hours to 24 hours ideal. |
| Combination of Wavelengths 1 and 2; 1 and 3; and 1, 2, and 3 | 6 hrs. continuously of wavelength 1 followed by 18 hours of wavelength 2 or 3 or a combination of wavelengths 2 and 3. Alternatively, wavelengths 1, 2, and/or 3 run simultaneously up to 24 hours. |
| PULSE WIDTH MODULATION | |
| Wavelength 1 PWM | Pulse Width Modulation (PWM) is used to tune the irradiance level by turning on and off the illumination at 10 to 100 Hz (Tyler range). Wavelength 1 will have a PWM of 25% to 75%. |
| PWM Waveform Type | Synchronous and asynchronous |
| PWM Waveform Pattern | Square wave |
| Wavelengths 2 and 3 PWM | Low PWM value to account to lower irradiance requirement. |
| Thermal Management | Vary PWM to control thermal temperature |
| Visual Perception | During off-time during treatment cycle, to help aid people in realizing the device is still on and running, one can set the PWM in the 1%-to-10% range rather than 0% and then raise the PWM back to peak value when the treatment cycle is supposed to be on. |

TABLE 7-continued

Example hexagon light guide and electronics layout description.

SENSORS

| | |
|---|---|
| General Description | Device has sensors that relay information regarding the wound to the power-pack or via wireless communication to a computer |

POWER PACK

| | |
|---|---|
| General Description | Device is controlled and powered by a wearable lightweight power-pack that can run off battery or wall outlet and controls the LEDs |

USE-CASE

| | |
|---|---|
| Example 1 | Device is placed directly on the surface of the skin, skin orifice, endothelial or epithelial surface, skin wound or implanted within the body or onto an implantable medical device (e.g., prosthesis) |
| Example 2 | Can be left in contact with the patient continuously for up to 7 days |

In at least one embodiment of light patches disclosed herein, light is generated by LEDs. LEDs may generate heat, which may raise the temperature of the light patch. In some embodiments, it may be disadvantageous for the light patch to be raised to above 41° C. at a required light dose. The LEDs may be pulsed using Pulse Width Modulation (PWM) to modify a total irradiance of the patch, and to reduce the total heat that is generated by the light patch.

A material of the light patch and of an associated PCB may be selected to reduce a temperature of the bandage. For example, a first design may be directed towards thermal dissipation with two, four, and six-layer boards using standard FR-4 and 1 oz/ft of copper. A second design may include a four-layer, 2 oz copper board. A third design may include alternatives to FR-4 including, for example, a metal core.

Other thermal management techniques may include changing the layers surrounding the light patch opto-electronics (for example, layers encapsulating the LEDs) by considering: adding more silicone/polyurethane to a patient side of the light patch to increase the temperature barrier; using optically clear materials to reduce LED power requirements; adding heat sinking materials to the back of each hexagon PCB; or pulsing a certain number of hexagons at any one instant, faster than the human eye can see.

The optics around the light patch may be optimized to be delivered using hexagonal light guides with LEDs on 3 edges; where each light guide and LED array is situated on a rigid PCB that is also hexagon-shaped. To allow the system to bend, all the flexing may occur between the hexagon PCB islands. Rigid flex circuits may be used for connecting the PCB islands, but traditional rigid flex boards may not allow for enough flexibility in the small space allowed between hexagons, which may be between approximately 1.3 to 2.0 mm. As an alternative, thin (28 gauge) wire may be used to connect multiple hexagons together. For example, FIG. 34 illustrates a top view of multiple hexagons 3400 connected by thin wire.

Figure 34:
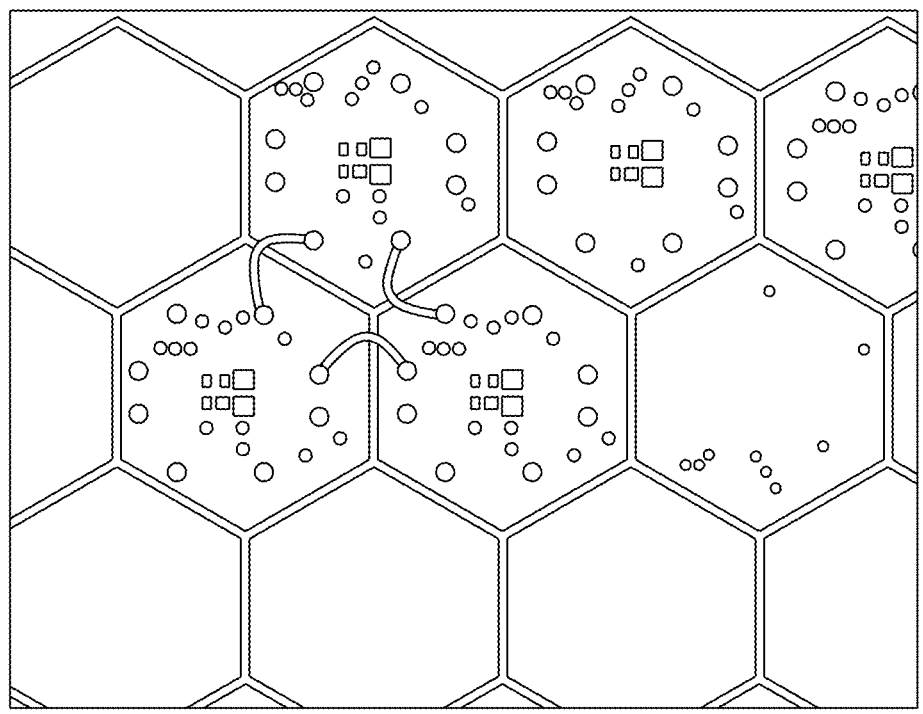
FIG. 34 illustrates a top view of multiple hexagons connected by thin wire according to an embodiment.

The layout of FIG. 34 may be problematic from a manufacturing perspective and may have reliability issues in regard to stress on solder joints, particularly if the Hexagon PCB islands are flexed often and/or with extreme bending forces. Accordingly, one of at least three solutions may be implemented according to the foregoing disadvantages.

Figure 36:
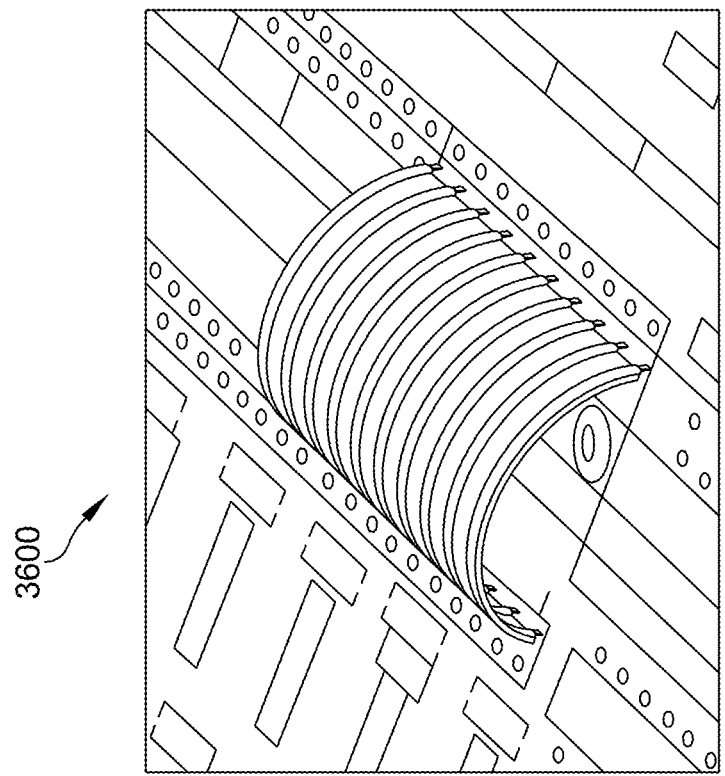
FIG. 36 illustrates a top perspective view of another flat flexible cable according to an embodiment.
Figure 35:
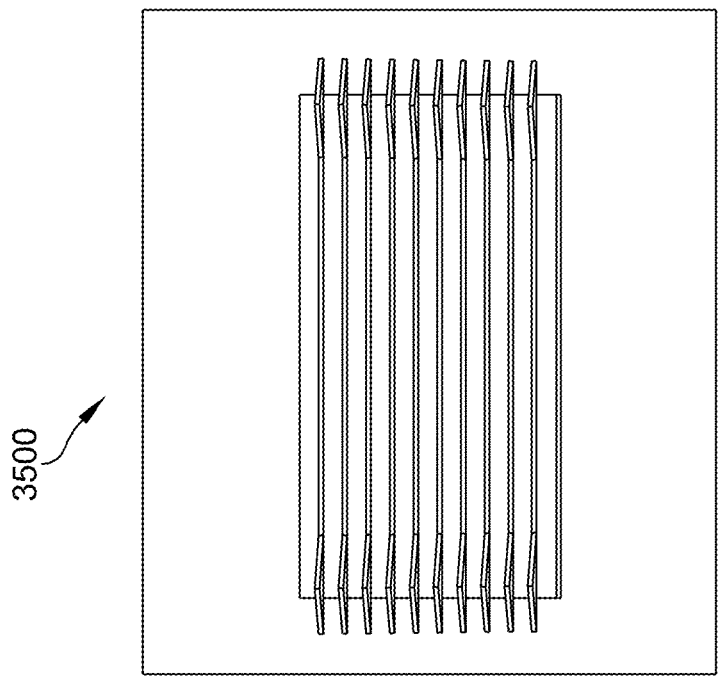
FIG. 35 illustrates a top view of a flat flexible cable according to an embodiment.

In a first solution, flat flexible cables may be used. For example, surface mount or through-hole flat cable jumpers may be used to connect the array of hexagons together. FIG. 35 illustrates a top view of a flat flexible cable 3500 according to an embodiment. FIG. 36 illustrates a top perspective view of another flat flexible cable 3600 according to an embodiment. In the embodiments illustrated by FIGS. 35 and 36, either surface mount or through hole connectors styles could be used such that the connections between hexagon PCBs could be made while still in the panel or at any more efficient stage in the PCB fabrication/assembly process.

Figure 37:
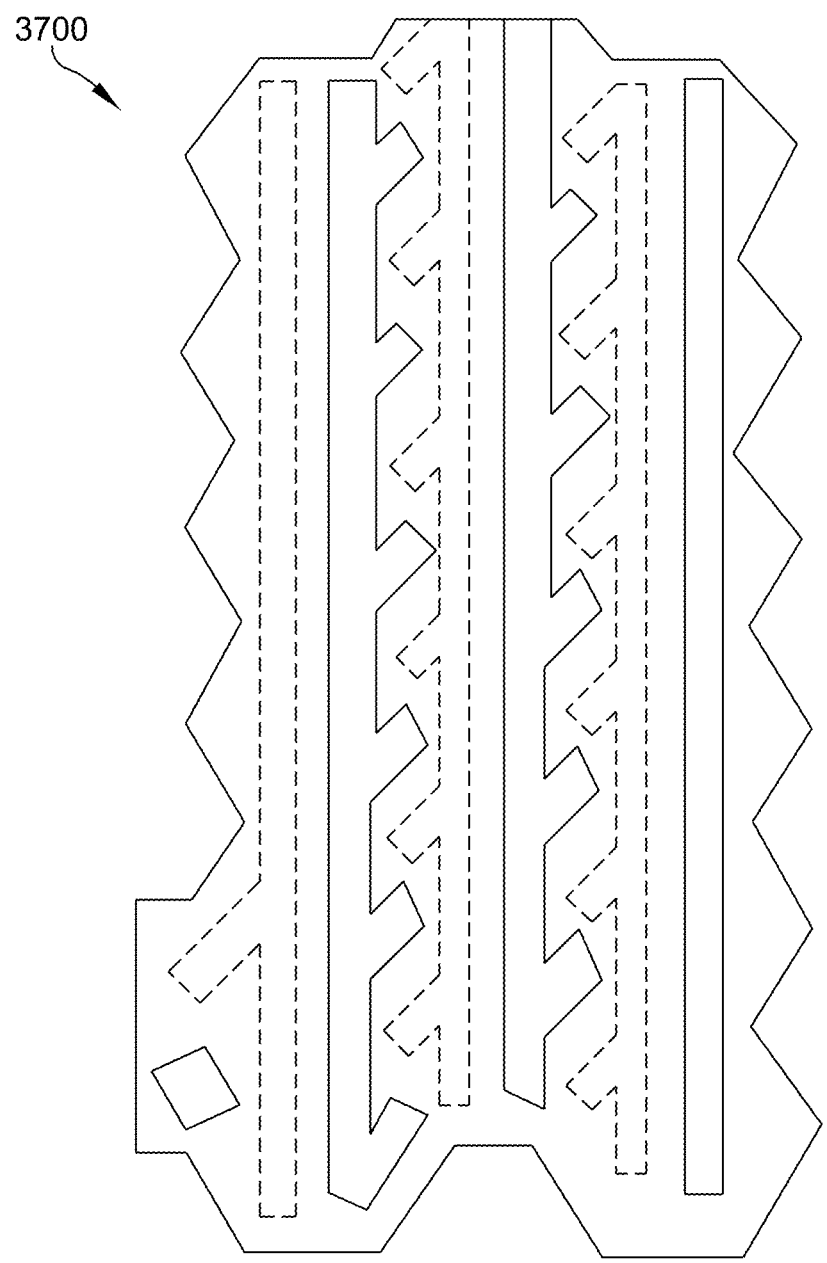
FIG. 37 illustrates a layout of a back plane connection layout according to an embodiment.
Figure 38:
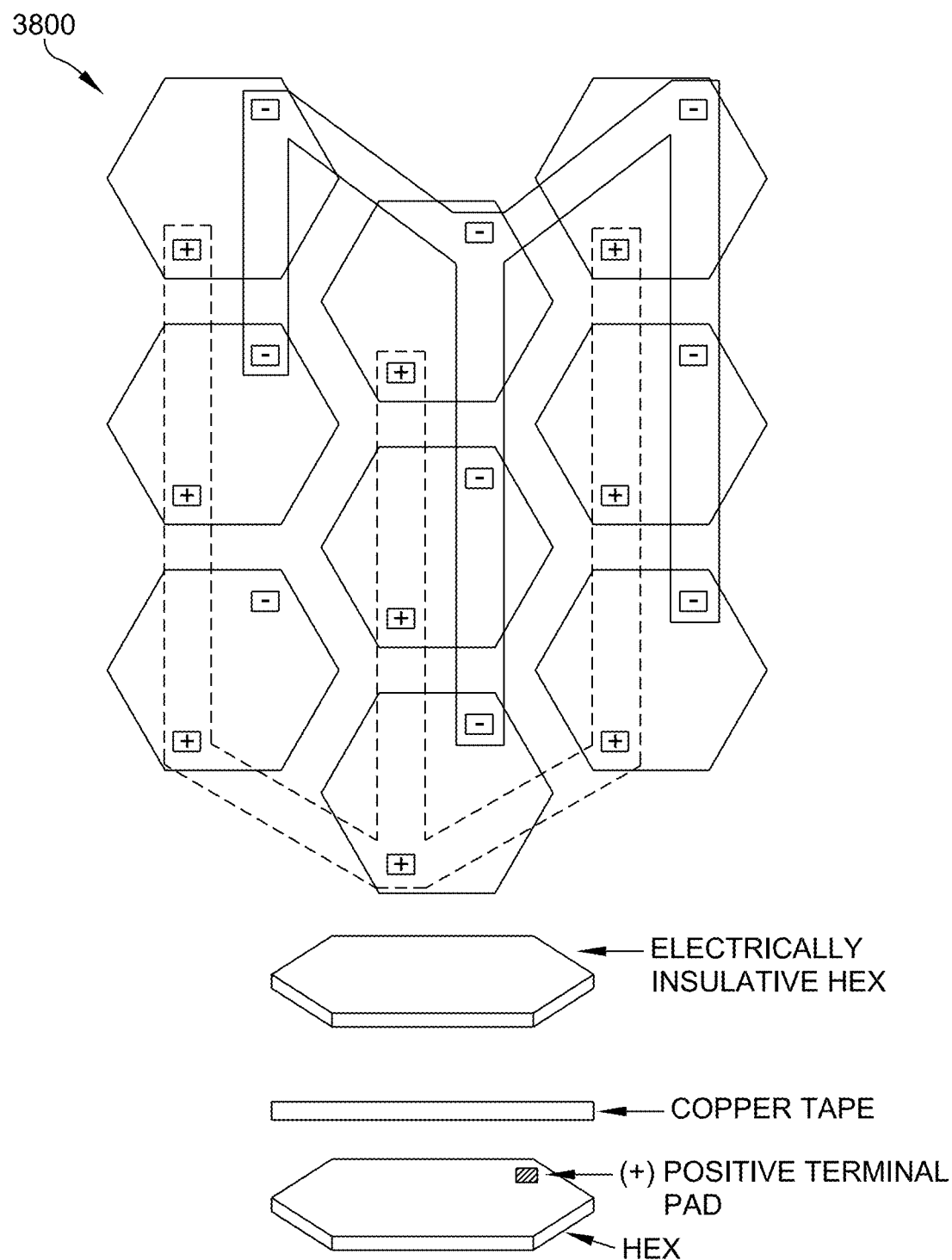
FIG. 38 illustrates a layout of a back plane connection layout according to another embodiment.

In a second solution, a conductive material may be adhered to each of the hexagon PCBs for electrical connections. For example, conductive ink may be printed onto a plastic sheet or a copper foil with a Kapton backing to be used for the electrical connection. The hexagon PCBs are still rigid PCBs but are connected by—ideally one—flexible circuit. FIG. 37 illustrates a layout of a back plane connection layout 3700 according to an embodiment. FIG. 38 illustrates a layout of a back plane connection layout 3800 according to another embodiment.

Figure 39:
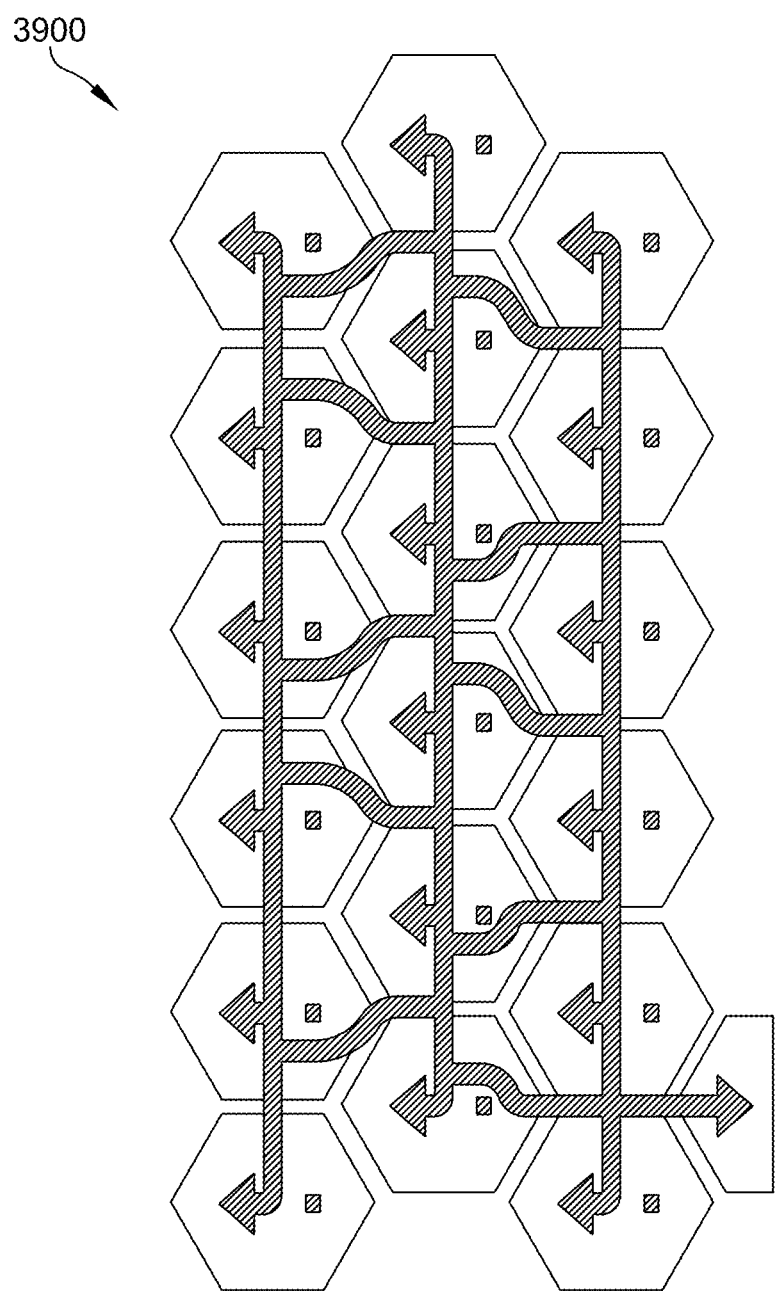
FIG. 39 illustrates shows a layout design for a Flat Flexible Circuit according to an embodiment.

In a third solution, a ZIF style connector may be used to connect each hexagon to one flat flex circuit. The flexible PCB may designed to connect all the hexagon PCBs in the 3×6 array together in a simpler process than soldering multiple connections. For example, FIG. 39 illustrates shows a layout design for a flat flexible circuit 3900 according to an embodiment. The arrows show the direction and approximate location of the connector located on each of the hexagon PCBs in this potential arrangement of connectors. The half hexagon will contain the connection out to the power source. The flat flexible circuit could be made to most easily be fit into place, reducing the number of individual hexagon-to-hexagon connections to be made.

Power Pack

In an embodiment a device comprises a power pack. In an embodiment the power pack is comprised of the following:
Rechargeable Battery
PCB control module
Power/Data Cable
Separate Power Recharge Station for Depleted Batteries The rechargeable battery can be inserted and removed from the structure/housing of the power pack. When fully charged, the battery will last up to 8-24 hours. Upon charge depletion, a new fully charged battery needs to be inserted to continue therapy. The depleted battery will need to be recharged on the separate power recharge station.

In an embodiment:
The power pack is configured to receive power from a wall outlet.
The power pack is configured to provide warning indicators using LEDs, sound, and/or displays.
The power pack is configured to allow data from the wound dressing to be processed and analyzed in the power pack.

The power pack could send data to a wireless server or network to record data and take in instructions or regiment information to individualize treatment.

Array

Embodiments of the present disclosure further include varying the size and shape of each light module, as well as the spacing between adjacent light modules.

Embodiments of the device include a light patch that is designed and built out of fiber optics. The fiber optics are in a bundle at one end which receives light from an LED source and then the light undergoes TIR through the fiber up to the other end. At the other end the fiber optics fan out into a flat array as shown in FIG. 5. FIG. 5 illustrates a fiber optic light guide 500, used for photodynamic therapy applications, where red lines indicate fiber optics and where each of the fiber optics is 0.5 mm in diameter. The fiber optic channels in the flat array zone are etched in a way to allow light to exit the TIR condition and refract out of the fiber optics. The etch is optimized to create a uniform light leakage over a 10 cm×10 cm area.

This design is very flexible and efficient, particularly when the device is bent causing "tipping" (generating a bend with a radius of curvature in one-dimension). The reason the device is flexible is because the light guides are not a "single body" so they allow tipping and some "tilting." Tilting is a bend in the device where the bend has a radius of curvature in one-dimension; typically orthogonal to the tipping bending direction. The light delivery and uniformity is efficient because the light is already in the body of a given light guide channel or fiber optic channel if there is any bending (or tipping).

Figure 6B:
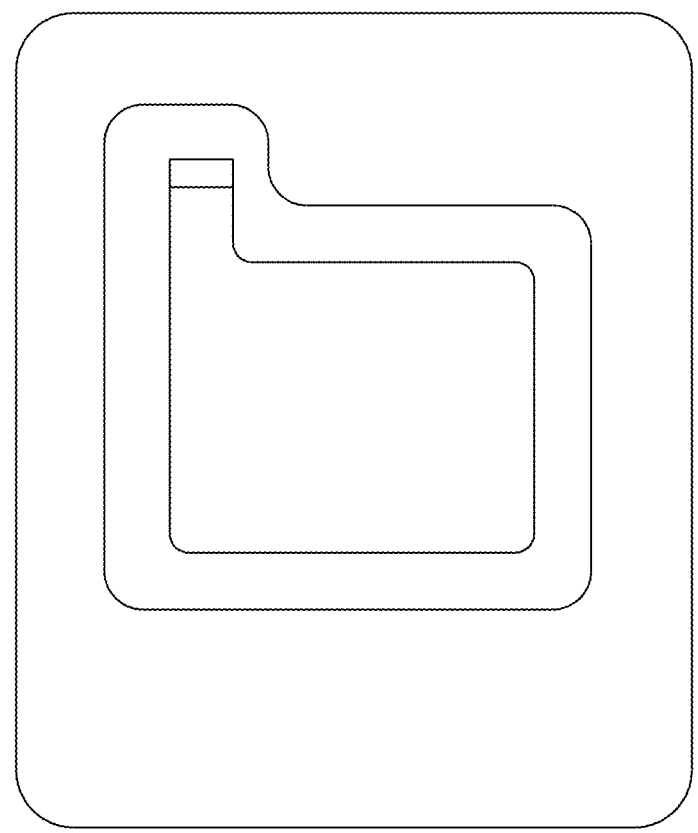
FIG. 6(b) illustrates an example implementation of the solid body light guide design.
Figure 6C:
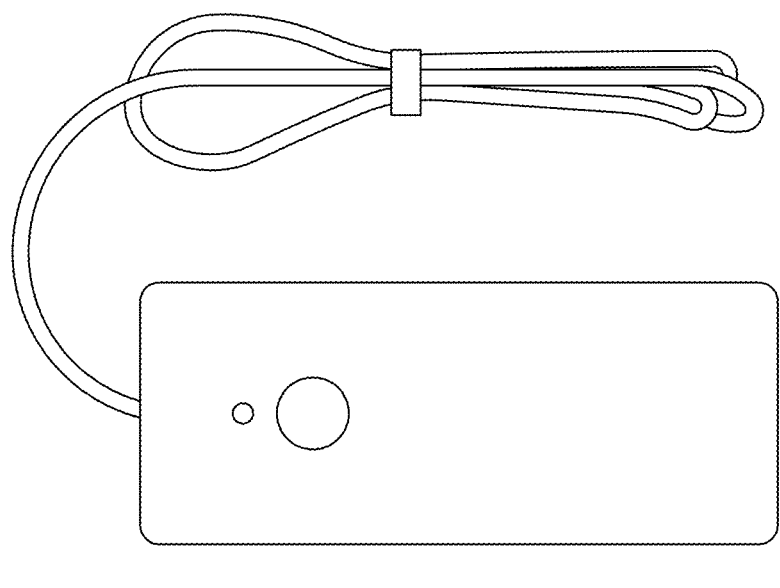
FIG. 6(c) illustrates a power pack corresponding to the example implementation of the solid body light guide design.

Due to manufacturing complexities with fiber optics, embodiments include a bandage that utilizes a "single body" light guide as shown in FIG. 6(a). FIG. 6(a) illustrates a solid body light guide design 600 for even-illumination phototherapy applications. FIG. 6(b) illustrates an example implementation 602 of the solid body light guide design 600 according to an embodiment. FIG. 6(c) illustrates a power pack 604 corresponding to the example implementation of the solid body light guide design 600 according to an embodiment.

Instead of discrete light guide channels like fiber optics the light guiding activity occurs in a single device (plate) which receives light from multiple and overlapping light sources (for example LEDs). The single body light guide design 600 is 0.5 mm and can receive light from side emitting LEDs in an array attached to a flexible PCB, wherein the red arrows illustrated in FIG. 6(a) indicate light rays from the LEDs. This design is easier to produce and it does allow for bending/flexibility for high radius of curvatures such as the chest wall (typically after mastectomy for a woman who has cutaneous metastases of breast cancer). The design also allows for more uniform and repeatable uniformity across the light guide surface. However, this design is not very flexible because now the light guide (compared to fiber optic channels separated from one another like in FIG. 5) is a single body so it retains rigidity despite the initial flexibility of the 0.5 mm thick material. Additionally, light may NOT be in the body of the light guide channel if there is any tipping (particularly extreme tipping).

Figure 7A:
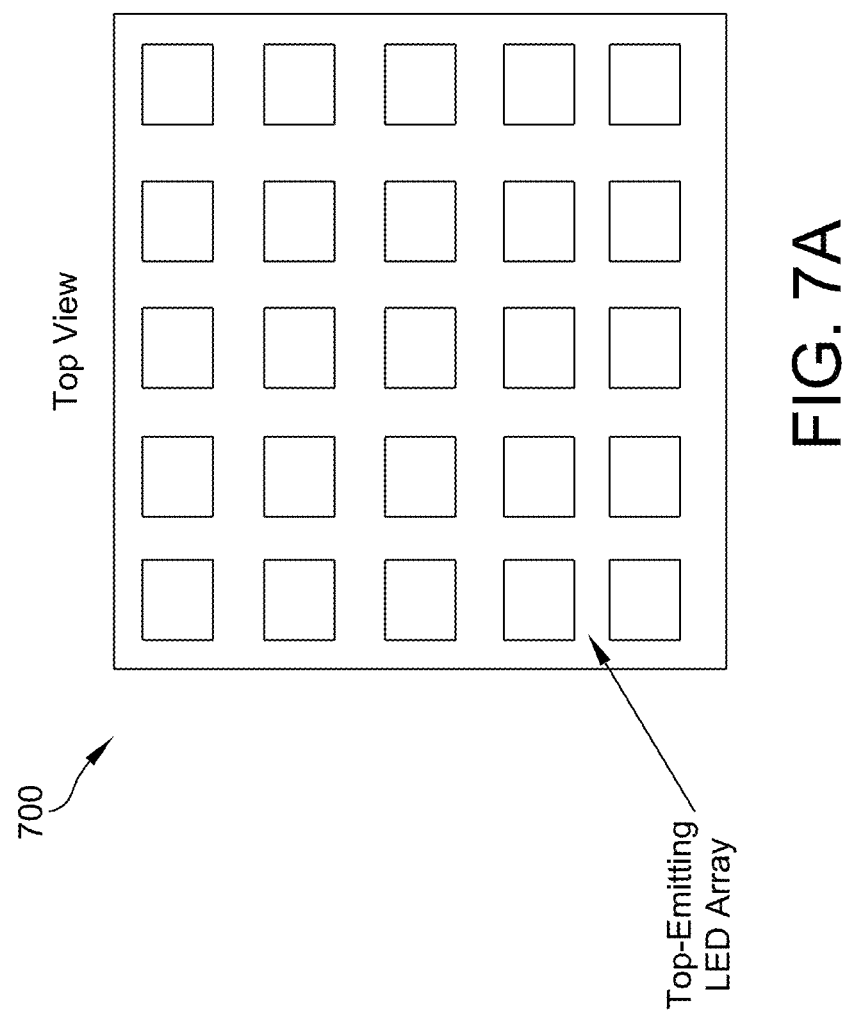
FIG. 7(a) illustrates a top view of an LED array approach to flexible light delivery.
Figure 7B:
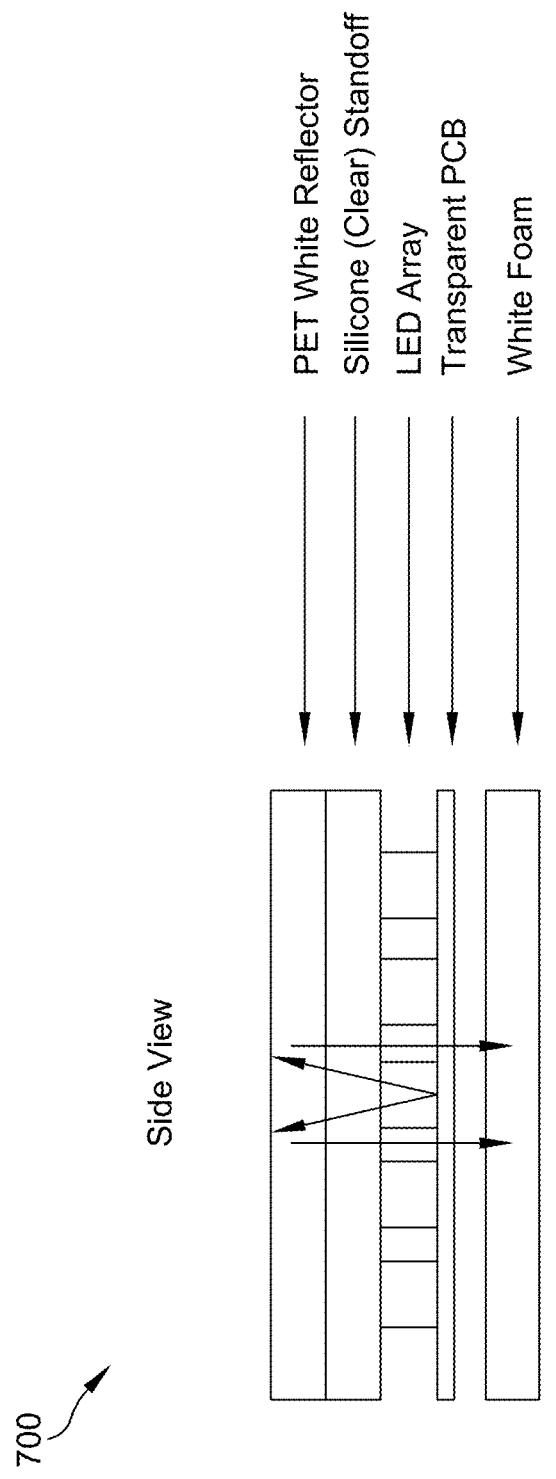
FIG. 7(b) illustrates a side view of the LED array approach to flexible light delivery.

As an alternative to the fiber optic system or the single body light body approach, embodiments of the device further include an LED array allowing flexibility in not only one dimension but in both the vertical and horizontal direction. For example, FIG. 7(a) illustrates a top view of an LED array 700 approach to flexible light delivery. FIG. 7(b) illustrates a side view of the LED array 700 approach to flexible light delivery.

In embodiments the devices described here have improved flexibility over fiber optic channels, and are configured to optimize evenness of illumination, for example, from an LED array which might otherwise have issues with even illumination due to the divergence of the light from the top emitting LED. Another problem causing a lack of uniformity is the inability to diverge and homogenize the light in such a short throw distance from the LED to the skin (it is several millimeters).

With fiber optics (FIG. 5) the device embodies flexibility (primarily in one dimension) but low light uniformity and is difficult to manufacture. With the single body light guide (FIG. 6[a]) the device is configured to have light uniformity but limited flexibility in both dimensions but the device is much easier to manufacture. With a discrete LED (light) system (FIGS. 7A and 7B) the design achieves two-dimensional flexibility and manufacturing is fairly easy, but uniformity can be compromised.

In embodiments the devices disclosed herein provide discrete light emission channels with at least two-dimensional flexibility and have the capability of emitting uniform light over a low profile (small thickness) in conjunction with ease of manufacturing.

One approach is to design the single body light guide to act as the fiber optic channels by breaking the single body light guide into an array of smaller single body light guides as shown in FIG. 8. FIG. 8 illustrates discrete light guides 800.

With the design in FIG. 8, the approach creates "pivot points" for tipping. Tilting is still limited. Compared to a single body light guide, this design approach reduces having light already in the light guide at the pivot points. The main drawbacks to this approach are that primarily only one axis has increased flexibility and, since the light is diverging, as indicated by the red lines in FIG. 8, there may be a decrease in the irradiance at the top of each light guide channel, particularly if the length of the channel is long, for example, over 50 mm.

Figure 9:
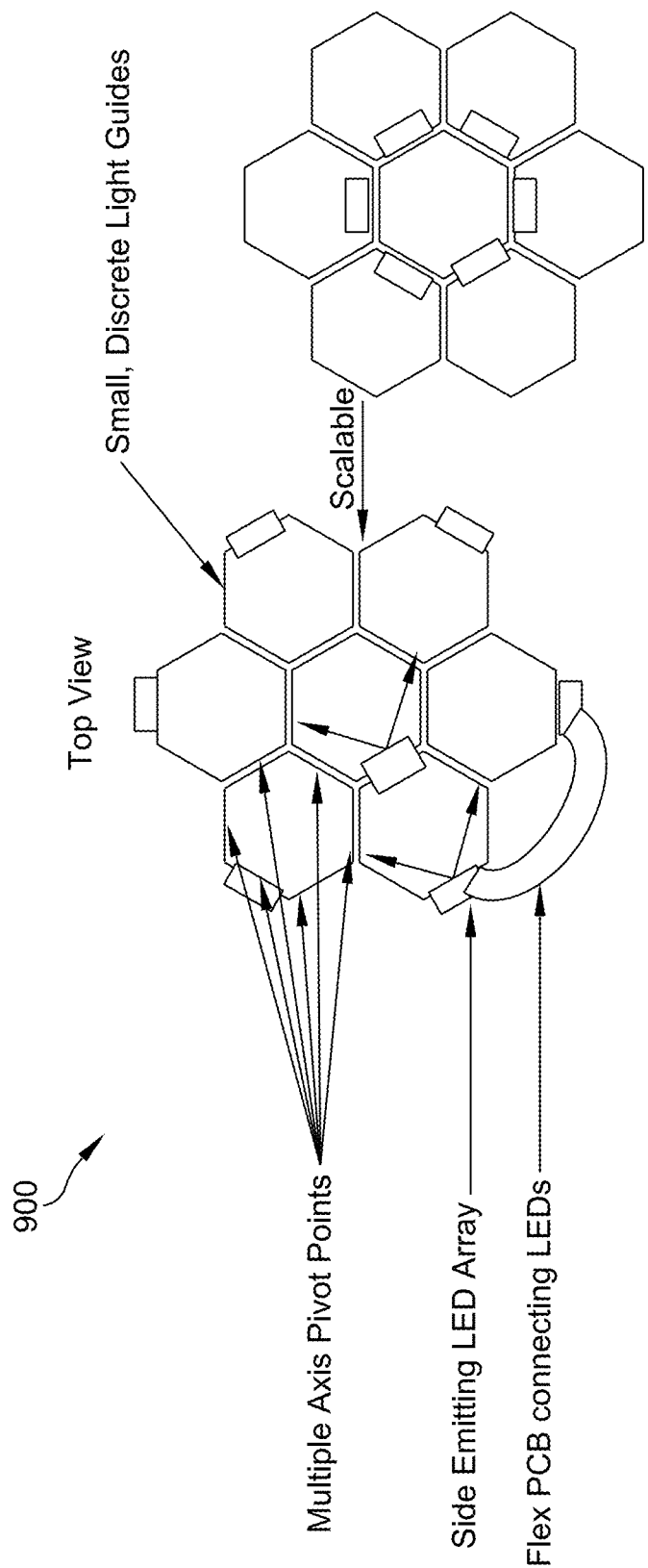
FIG. 9 illustrates an LED and hexagonal light guide array design.

An alternative approach to long/elongated but smaller single body light guides is to develop small but multifaceted shapes that allow light to enter the light guide from multiple inputs to create uniformity while also creating a functional shape that allows for multiple deflection or multiple dimensions of flexibility. An optimized shape that meets these criteria includes hexagons as shown in FIG. 9. FIG. 9 illustrates a hexagon design 900. This design also addresses the light divergence problem of long light guides and avoids the excessive throw distance/height of an LED array needed to get uniform coverage.

In FIG. 9, each hexagon is isolated, tied by a thin flex circuit. Flexibility is enabled on six planes, and each hexagon has a single LED. Each hexagon provides even illumination, which eliminates the diffusion problem of the LED array, and the hexagon surface area improves the light divergence issue.

Figure 10:
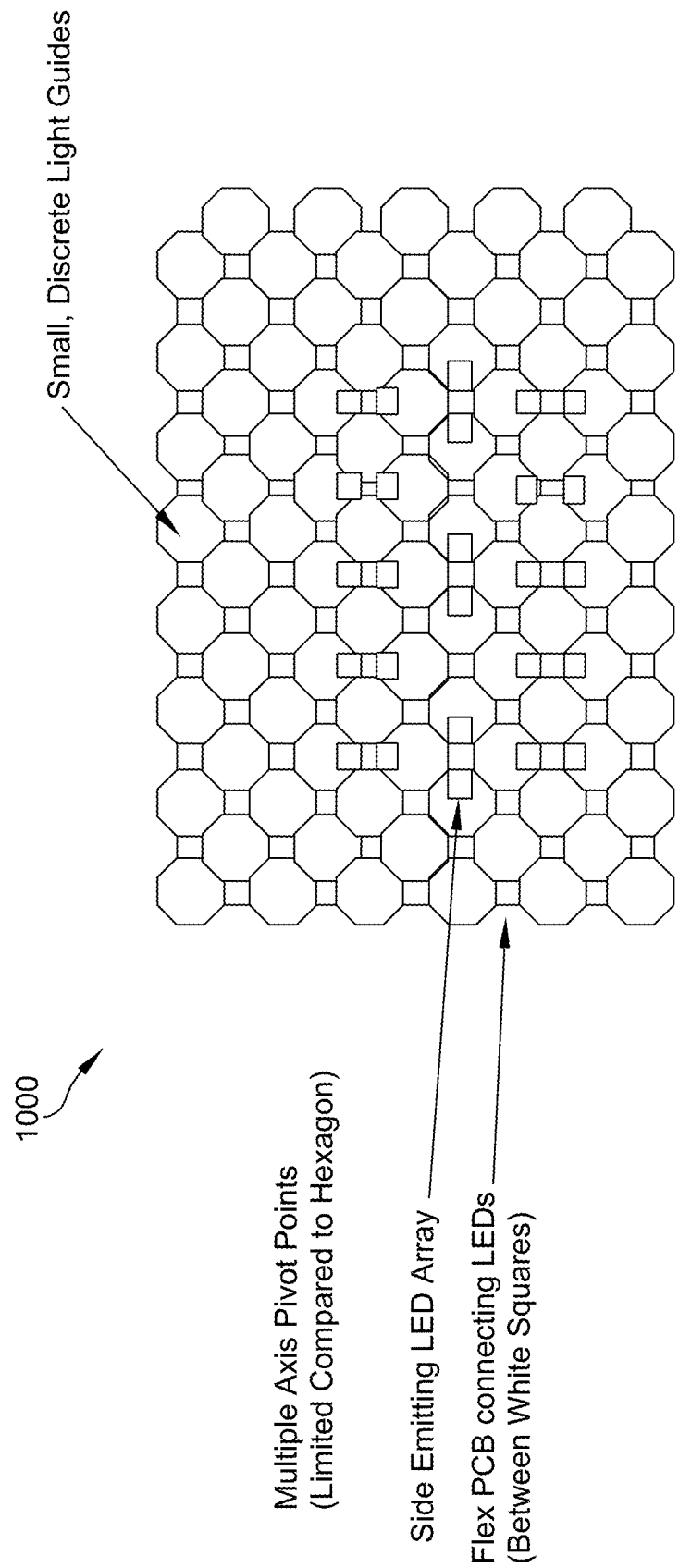
FIG. 10 illustrates an LED and octagon light guide array design.

Other polygon shapes can be used. For example, FIG. 10 illustrates an octagon design 1000. However, the hexagon shape is desirable because it allows for a wide degree of flexibility across multiple pivot points but without sacrificing continuous illumination between the spaces (aka "dead zones") between each discrete light guide. As can be seen in FIG. 10, there are much larger dead zones between each light guide, such that there will be a much larger effect of light falloff from light guide to light guide and the area in the dead zone will be dimmer/darker compared to the light exiting a given light guide. The dead zone and brightness effects can be minimized with a hexagon-shaped array compared to some other polygon shapes. Other shapes like triangles and squares could be good light guide shapes but with triangles, light uniformity from multiple edges could be a problem and an array of closely stacked squares (or rectangles) will have to deal with a greater number of issues pertaining to dead zones, light uniformity, and potential buckling when the array is bent.

In one embodiment, a preferred size is of importance based on flexibility required, the light output (expressed in milliWatts [mW]) of the LED, and the light input required for a therapeutic response. Assuming that a pivot point is based on the longest diagonal of a hexagon, then the size (or diagonal) of the hexagon should be set so that the smallest hexagon can pivot around the smallest-sized anatomy required for treatment. If a finger is to be treated with light, for example, then an ideal size for a hexagon light guide is 10 to 15 mm along the diagonal. For a leg or torso, the hexagon size could be larger, such as approximately 50 mm.

A tradeoff on the hexagon size is that smaller hexagons require more LEDs if the hexagons are built into an array that will cover a larger surface body area. As the hexagon size gets larger, the LED requirements also increase—depending on the irradiance required. If the light output out of the light guides needs to be above 1 mW/cm$^2$, then the LED has to have a large output, when coupled as an LED array, to achieve the irradiance over a large throw (light divergence) distance. Essentially, there comes a point where a large hexagon becomes as big as, or functions just like, the single body light guide as discussed in FIG. 6(a).

For arms and legs, a preferable hexagon size is between 15 mm to 25 mm with 20 mm and 22.5 mm as a most preferable size. For fingers, nose, or ear anatomy, a hexagon size of 10 mm to 15 mm is most preferable. For larger anatomical surfaces, 35 mm is preferably the maximum hexagon size.

The gap between hexagons or each individual polygon is important. The gap provides the pivot points and flexibility. The gap also provides the areas where the individual light guides and circuitry are connected and where some hard-mounted circuits such as the LEDs, resistors, LED drivers, and other items, sit. In embodiments an optimized gap allows for flexibility and placement of electronics while at the same time minimizing dead zones (areas where light is not present and where light is uniform from one polygonal light guide or emission surface to the next) and making sure that, as the entire electro-optical system is bent, the individual light guides do not crash into each other. For the hexagon, an exemplary gap size is between 0.75 mm and 2.50 mm for hexagon sizes ranging from 15 mm to 25 mm, respectively. For hexagons that are sized 22.5 mm, an exemplary gap is approximately 1.6 mm. In general, the preferable gap to diagonal width of a hexagon, as pertaining to a percentage, is between 5% and 10%.

As for the layers connecting the individual hexagon light guides, there are, in embodiments, one or more polyimide layers that include electrical traces and positional features to solder LEDs, resistors, pulse-width-modulators, LED drivers, MOSFETs, amplifiers, and other basic electrical components. In embodiments, the layers are between 25 μm to 500 μm thick and although the layers are thin between the hexagon light guides, there is a more rigid (thicker) layer behind the light guides and where the LEDs sit so as to provide greater reliability to the core light-emitting objects even when the connection layers are being flexed.

Figure 12:
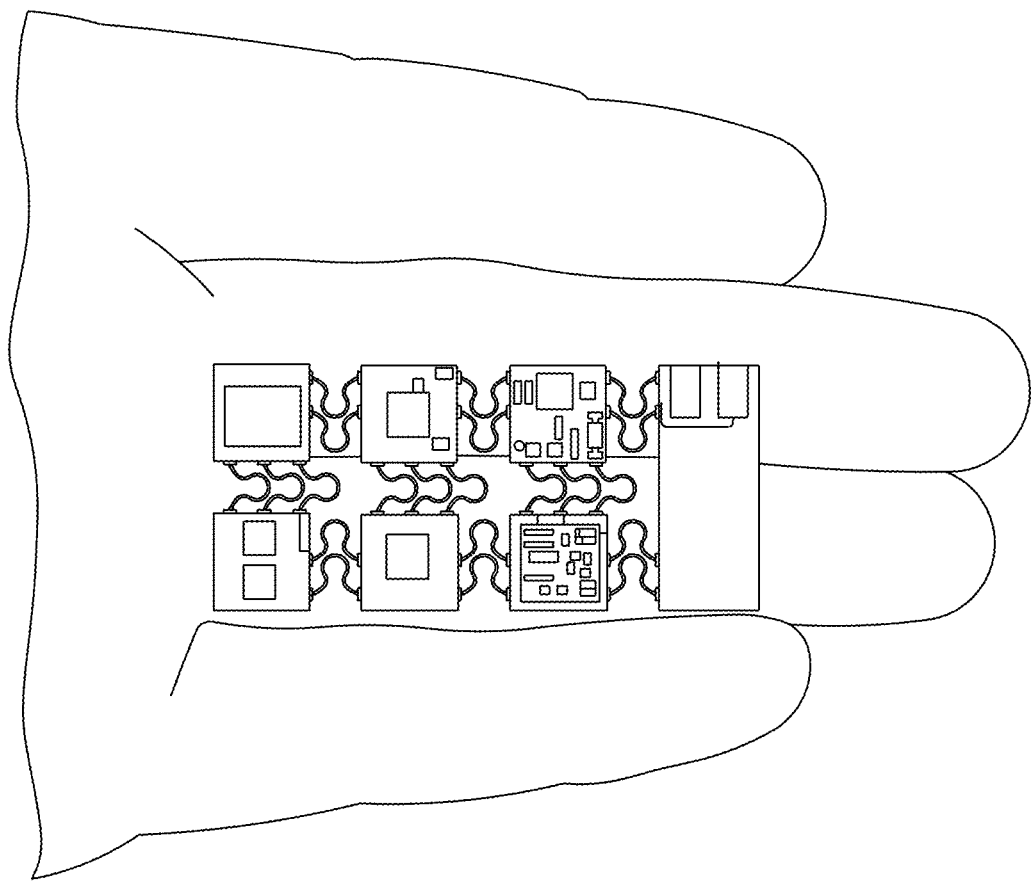
FIG. 12 illustrates multiple flex connections between components of an LED and light guide array.

In embodiments, connections between the individual hexagon light guides can be flat bridges or could be multiple flex connections. For example, FIG. 11 flat connections 1100 between light guides of an LED and light guide array, and FIG. 12 illustrates multiple flex connections 1200 between components of an LED and light guide array. Additional sensors (temperature sensors, pH sensors, capacitance sensors, etc.), can be dispersed around the primary connections between the individual light guides.

Pulsing

Killing organisms requires light, a photosensitizer, and oxygen. Administration of the light at higher irradiance depletes the endogenous photosensitizer and $O_2$. In some settings, such as in hypoxic wounds, the light can be pulsed with 2 to 10 minute dark periods to allow the organisms to produce photosensitizer and restore the tissue oxygen tension. The dark periods may need to be longer for certain parasites, such as roundworms and flat worms, where cell multiplication is much slower and requires heme from the host. In this setting the dark time may be 1 to 4 hours.

Pulsing the light source from light (ON) to dark (OFF) can provide benefits from a microbiology perspective and a device-based perspective. From a microbiology perspective, when delivering low-irradiance at a higher threshold, pulsing the light will effectively reduce the total number of photons delivered and the rate of oxygen and photosensitizer completion (photosensitizer in this case would refer to photoacceptors, porphyrins, flavonoids, chromophores, etc. already endogenous to the bacteria). The period between dark periods can allow the oxygen levels and photosensitizer to recuperate, thereby allowing for the treatment to be performed continuously—over 24 hours to 72 hours or longer. The dark period should be sufficiently long to account for the intensity or irradiance delivered by the light-source such that for higher irradiances a slightly longer dark period would be beneficial compared to lower irradiances, where a slightly shorter dark period would be beneficial. Simultaneously, the dark period should not be overly long such that bacteria are replicating (multiplying) or too short such that no further bactericidal effects can occur naturally (other than thermal damage) when the biologically affected area has depleted levels of oxygen or photo sensitizer elements available such that any photons delivered to this area cannot adequately start the ROS process.

Pulsing the light source to go from light to dark has an advantage for the device delivering the light. Higher irradiance and/or long-duration light delivery requires significant power to emit light continuously to a given treatment site. Pulsing the light source will turn the light off for a given time period which will effectively reduce the power required. This aids in the device when it is running off an external battery system that requires recharging once the power is depleted. If power is conserved by pulsing the light source, the external battery can maintain a charge longer while in operation, thereby allowing for a longer time period between recharging the battery by the user.

Pulsing the light source can by symmetric (for example, 5 minutes On and 5 minutes Off) or asymmetric (for example, 20 minutes On and 10 minutes Off; or 10 minutes On and 20 minutes Off). The pulsing can consist of different pulses so that the light intensity changes during the pulse. The pulse can be a square wave, triangle wave, trapezoid wave, sinusoidal wave, etc. The pulsing rate and pulse wave type can change in time during a given treatment. The pulsing rate and pulse wave type can vary for any given wavelength emitted by the device or system. The pulsing time can be under 1 second, 1 minute, 1 hour, or up to 1 day.

Combination Therapies

Devices and methods disclosed herein can be used with adjunctive or additional therapeutic modalities, for example, methods described herein can be used in combination with an antibiotic, for example, antibiotic primary organisms involved in skin/soft tissue infections, which include *Staphylococcus aureus* (MRSA methicillin RSA and MSSA methycilllin) and Staph epidermidis. (coagulase-negative Staph). For these types of infections, methicillin is most commonly prescribed, followed by vancomycin or doxycycline. As an adjuvant to antibiotic therapy, rifampin is prescribed in conjunction with these drugs given its antibiofilm properties for Staph species (it does not kill off the bacteria, but has been shown to penetrate through the biofilm).

In addition to Staph species, the other more significant risk for skin and soft tissue infections is *Pseudomonas*, which is most often managed through Cefepime, Zosyn and Carbapenems.

Methods and devices described herein can be used with drugs from Tables 3 and 4, below.

Methods and devices can be used with or without photosensitizers or dyes, for example, photosensitizers from Table 1.

TABLE 1

Dyes and Photosensitizer

| # | Trade Name | Molecule |
|---|---|---|
| 1 | ALA | 5-aminolevulinic acid |
| 2 | Foscan | Meta-tetra(dyroxyphenyl) chlorin |
| 3 | Lu-Tex | Lutetium texaphyrin |
| 4 | NPe6 | Mono-L-aspartyl chlorin-e6 |
| 5 | Pc4 | Silicon phthalocyanine |
| 6 | Photochlor | Hexyl ether pyropheophorbide-a derivate |
| 7 | Photofrin | Hematoporphyrin derivative |
| 8 | Photolon | Chlorin-e6-polyvinylpyrrolidone |
| 9 | Photosens | Aluminum phthalocyanine |
| 10 | Purlytin | Tin ethyl etiopurpurin |
| 11 | Tookad | Palladium-bacteriopheophorbide)-a |
| 12 | Visudyne | Benzoporphyrin derivative monoacid ring A |

In addition to the dyes and photosensitizers described in Table 1, other dyes or photosensitizers include St. John's wort, topical toluidine blue, methyl blue, and all other acridine dyes likely placed on the skin surface, on the biofilm, or on the wound bed.

Sensors and Processors

In embodiments, the device includes sensors, for example, for monitoring a parameter, for example, at the site of irradiation. For example, responsive to a signal from the sensor indicating, for example, an increase in temperature, the device or a processor or computer connected thereto alters an activity. For example, if the temperature rises, the pH drops, and turbidity increases, this signals that an infection is developing and alerts the user.

Pathogens

Devices and methods of the invention can be used against a broad spectrum of pathogens, including bacteria, fungi, protozoans, and parasites. Devices and methods of the invention can be used against gram positive bacteria and gram negative bacteria.

Some pathogens require a higher energy level. Because of heat and other concerns, it may be desirable to start with a higher symmetry value reflecting the need for a higher energy level, but as that pathogen is killed or neutralized to decrease the symmetry value.

*Klebsiella* is a gram negative facultative anerobe, and ferments lactose. A relatively higher energy level is needed to kill or neutralize it. *Klebsiella* lives in a lower $O_2$ environment, so it may need more intervening periods. *Klebsiella* also fixes N, which may deplete free radicals, making it more difficult to kill or neutralize.

Bacterial pathogens which can be treated with devices and methods described herein are provided in Table 3. Fungal infections can be treated with devices and methods described herein. Protozoans are traditionally found in aqueous environments in a wide range of trophic levels. Parasitic protozoans exhibit osmotrophy, a process by which they imbibe the nutrients from their environment directly, as they are mostly present in nutrient-rich environments. An interesting feature about these parasitic protozoans is their dramatic life cycle. The reproductive cycle includes short generation times, and alternates between an infective proliferative stage and a dormant cyst stage. Parasitic protozoa that affect humans are provided in Table 2

TABLE 2

Parasitic protozoa that affect humans

*Entamoeba histolytica* (causes amoebiasis)
Exoparasites, not related to burn risk:
*Toxoplasma gondii* (causes oxoplasmosis)
*Cryptosporidium* (causes cryptosporidiosis)
*Trichomonas* (causes trichomoniasis)
*Trypanosoma cruzi* (causes Chagas disease)
*Leishmania* (causes leishmaniasis)
*Trypanosoma brucei* (causes African trypanosomiasis)
*Naegleria fowleri* (causes Naegleriasis)

Parasites will now be discussed in greater detail.

*Trypanosoma cruzi*. More than 300,000 Americans are infected with *Trypanosoma cruzi*, the parasite that causes Chagas disease, and more than 300 infected babies are born every year. Chagas disease is transmitted through a bite from the triatomine bug, which then deposits its feces in the skin opening. Chagas disease can cause long-term digestive, cardiac, and neurological complications. Death from the infection is often caused by heart attack. However, if caught early, the condition is easily cured with medication.

Cysticercosis. This parasitic infection, caused by the *taenia solium* tapeworm, makes its home in human tissues such as the brain and muscles. Larval cysts from the parasite form in the body and can cause a number of complications, including seizures. There are at least 1,000 hospitalizations for cysticercosis per year in the U.S. This tapeworm infection is often the result of eating uncooked pork that contains larval cysts.

Toxocara. Approximately, 13.9 percent of the U.S. population has antibodies against this parasitic infection. Sadly, the rest of us are at risk for acquiring it through roundworms often found in the intestines of dogs and cats. About 14 percent of Americans have had exposure to toxocara, and at least 70 people die from the infection each year. According to the CDC, most of the infections are in children and many suffer blindness due to related eye disease.

Methods and devices described herein can be used to treat subjects having a drug resistant pathogen, for example, a pathogen from Table 3 or a pathogen resistant to a drug from Table 3 or 4.

TABLE 3

Bacteria and resistance

| # | Bacteria Type | Antibiotics Resistant |
|---|---|---|
| 1 | *Acinetobacter baumannii* | Carbapenem |
| 2 | *Pseudomonas aeruginosa* | Carbapenem |
| 3 | Enterobacteriaceae | Carbapenem, ESBL-producing |
| 4 | *Enterococcus faecium* | Vancomycin |
| 5 | *Staphylococcus aureus* | Methicillin-resistant, Vancomycin-intermediate |
| 6 | *Helicobacter pylori* | Clarithromycin |
| 7 | *Campylobacter* spp. | Fluoroquinolone |
| 8 | *Salmonellae* | Fluoroquinolone |
| 9 | *Neisseria gonorrhoeae* | Cephalosporin-resistant, Fluoroquinolone-resistant |
| 10 | *Streptococcus pneumoniae* | Penicillin-non-susceptible |
| 11 | *Haemophilus influenzae* | Ampicillin |
| 12 | *Shigella* spp. | Fluoroquinolone |

TABLE 4

List of Drugs

| # | Drug |
|---|---|
| 1 | Ampicillin - Ciprofloxacin |
| 2 | Methicillin |
| 3 | Vancomycin |
| 4 | Doxycycline |
| 5 | Carbapenem |
| 6 | Cefepime |
| 7 | Zosyn |
| 8 | Fluoroquinolone |
| 9 | Clarithromycin |
| 10 | Cephalosporin |
| 11 | Penicillin |

Killing organisms requires light, a photosensitizer, and oxygen. Administration of the light at higher irradiance depletes the endogenous photosensitizer and $O_2$. In some settings, such as in hypoxic wounds, the light needs to be pulsed with 2-10 minute dark periods to allow the organisms to produce photosensitizer and restore the tissue oxygen tension. The dark periods may need to be longer for certain parasite such as roundworms and flat worms where cell multiplication is much slower and requires heme from the host. In this setting the dark time may be 1-4 hours.

Targets for irradiation treatment include burns, ulcers, and points of percutaneous entry. The target can be on a surface of the subject, for example, the skin or the surface of a wound, or the surface of any natural orifice.

Burn patients' wounds are kept in an aqueous environment to prevent desiccation of the burn wound. *Pseudomonas* and MRSA are therefore the most common contaminants in these wounds and can cause infection. *Pseudomonas* thrives in an aqueous environment. In addition, *Candida albicans* is a yeast that can be killed with 405 nm light and is also very common in moist environments.

Free radicals that interfere with bata lactamse production, such as VRE, can convert MRSA to make it penicillin sensitivity. The bacteria has plasmids, they code for small molecules that form Ab resistance. Free radicals poke holes in the cell membrane. They may also damage the ER.

Targets include natural orifices and the contents thereof, for example, the oral cavity, nasal passages, urethra, anus, vagina, and ears. Thus infections that enter through, or occur in, a natural orifice can be treated with continuous low-irradiance and the devices that deliver continuous low-irradiance. Included are infections, for example, bladder infections and prostatitis where the organisms swims up the urethra, and sinusitis with the organism comes in through the nasal passages, ear canal, etc. Method and devices disclosed herein can be used to treat iatrogenic infections in which the organism gains access through a puncture (intentional or otherwise) made through the skin or other tissue, for example, a puncture occurring with a via or a catheter to generate infections, for example, central line infections, arthroscopy infections, etc. or percutaneous implants infections.

Negative Pressure Wound Therapy And Non-Adherent Wound Bed-Facing Members

Devices described herein can be configured to place the wound bed at sub-atmospheric pressure, sometimes referred to herein as negative pressure wound therapy (NPWT). Unwanted substances, including exudates that inhibit healing, or materials that comprise infectious agents, or mediators of inflammation, for example, T cells, B cells, or macrophage, can thus be suctioned away and the amount thereof reduced at the wound bed.

Devices described herein can be configured to comprise a non-adherent member adjacent to the wound bed. In embodiments this optimizes healing, minimizes, reduces, or inhibits, the growth or level of unwanted organisms, for example, a bacterium, spore, or fungal element, and minimizes negative effects of dressing changes or device removal.

These embodiments can also be combined. Thus, in embodiments a device described herein is configured to provide NPWT and a non-adherent member adjacent to the wound bed.

Components for use in the devices described herein can be adapted from known components, see, for example, U.S. Pat. Nos. 8,444,611, 7,857,806, 7,534,240, 5,636,643, 9,717,829, 9,642,950, 9,352,076, 9,302,034, 9,089,630, 8,772,567, all of which are hereby incorporated by reference.

In an embodiment a light-emitting element, for example, an array of a plurality of light emitting modules, is disposed between the wound bed and a gas-impermeable member which allows a pressure differential between the wound bed, or the space defined by the gas-impermeable membrane (the reduced pressure space), and ambient atmosphere. The gas-impermeable member separates the wound or the reduced pressure space from the outside environment, and allows the negative pressure to act on the area of the wound. In embodiments the gas-impermeable membrane forms a seal with the surface of the subject.

The reduced pressure space is typically configured to be continuous with a vacuum or reduced-pressure source, for example, a suction device, for example, a pump, or wall suction. The connection to the vacuum source can be controlled, for example, by a valve. The valve or application of negative pressure can be under manual control, computer control, or both. The application of vacuum can be programmed to occur at predefined times, periods, or conditions. The reduced pressure space can be connected to the source of vacuum by way of a fenestrated tube or disc.

In an embodiment the application of negative pressure is constant throughout the use of the device or throughout a portion of the time the device is contacted with the subject. In embodiments, the device is configured to allow different pressures, for example, at different times of the day, at different stages of treatment or healing, or with different wavelengths of light being applied. For example, in an embodiment a first level of negative pressure is applied at a first point of a preselected period, for example, a 24 hour period, and a second level of negative pressure is applied at a second point of the preselected period. In an embodiment a first level of negative pressure is applied at a first stage of healing or treatment, and a second level of negative pressure is applied at a second stage of healing or treatment. In an embodiment a first level of negative pressure is applied during irradiation at a first wavelength, and a second level of negative pressure is applied during irradiation with a second wavelength. In an embodiment a high level of negative pressure (more suction) is applied during irradiation with a first wavelength and a lower level of negative pressure is applied during irradiation with a second wavelength. In an embodiment the first wavelength is shorter than the second wavelength, for example, the first wavelength comprises light in the blue region of the spectrum and the second wavelength comprises light in the red region of the spectrum. Control of pressure can be effected automatically or manually. Control can be effected by a device, for example, a device comprising a computer or microprocessor, which device can also control other parameters, for example, wavelength, intensity, temperature, and the like.

Application of vacuum can be continuous or intermittent. In an embodiment negative pressure is provided at between −75 mm Hg to −125 mm Hg.

Devices described herein, for example, devices configured for providing negative pressure at the wound bed, can include a non-adherent member disposed adjacent to or in contact with the wound bed, for example, disposed between the subject, for example, the wound bed, and other elements of the device, for example, an array of a plurality of light emitting modules. In embodiments the non-adherent member minimizes fibroblast, keratinocyte, or other cell growth into the device or a component of the device such as the non-adherent member. In embodiments growth into the non-adherent member is minimized as compared to what is seen with a porous material, for example, an open cell foam or gauze. The non-adherent member allows separation from the wound bed, for example, in changing a dressing, or removal or adjustment of a device described herein with minimized removal of new cells. In an embodiment use of a non-adherent member, or other material that minimizes open cells, minimizes bacterial growth, which can occur in the cells of porous materials.

Non-adherent members, for example, a light-emitting element, for example, an array of a plurality of light-emitting modules, can comprise a synthetic rayon mesh material, a closed-cell foam, or low-surface coatings and materials. In embodiments the non-adherent member comprises a woven element, for example, gauze, coated with a non-adherent material, for example, Teflon® or polytetrafluoroethylene. In an embodiment a non-adherent member comprises a Telfa® coated woven mesh or other element.

A non-adherent member can be separate from, or integral with, another element of the device, for example, a light-emitting member or array, for example, hexagonal members. In an embodiment a light emitting element, for example, an array of a plurality of light-emitting modules, has a non-adherent member, for example, a layer, disposed, for example, formed or coated on, a surface that faces the wound bed. The non-adherent member can be disposed, for example formed or coated, directly on the light-emitting surface of a light-emitting array, or on an additional optical layer disposed on the light-emitting array. In an embodiment the device comprises an array of light-emitting modules having a non-adherent surface exposed to the wound bed, an absorbent element positioned to accept exudate or other liquid produced or present at the wound bed, and an element that seals the device with the subject allowing for the maintenance of negative pressure at the wound bed.

The non-adherent member can comprise a closed-cell foam or other non-adherent material, including porous materials provided with, for example, coated with, a non-adherent surface.

In embodiments the light-emitting array comprises an element, for example, a coating, for example, a conformal coating, that inhibits contact of liquid, for example, water, with the light-emitting array or components thereof. This can inhibit damage by liquid, water, or other environmental corruption. The layer, for example, a conformal coating, can be used in conjunction with other non-adherent layers.

In an embodiment, an element of a device described herein, for example, a non-adherent member or element, for example, a light-emitting array which comprises a non-adherent surface, can be configured to allow fluid transfer, for example, transfer away from the wound bed. For example, the element can comprise one or a plurality of conduits or channels, for example, holes, which provide for transfer of liquid away from the wound bed. A conduit, channel, or hole can be several micrometers to millimeters in diameter or perimeter. In an embodiment the device comprises a reservoir to receive transferred liquid. The reservoir can comprise an absorbent member, for example, which can comprise open cell foam or gauze-like materials. In an embodiment the reservoir is disposed on the surface of the light-emitting array that does not face the wound bed and the light-emitting array is configured to channel fluid away from the wound bed to the reservoir. In an embodiment the reservoir, for example, open cell foam or gauze, is attached to the light-emitting array by direct contact and application of a gas-impermeable member, for example, a drape/semi-occlusive dressing, to create a seal for NPWT. In an embodiment a reservoir, for example, open cell foam or gauze, is adhered, for example, by an acrylic or silicone adhesive, to the back (non-wound side) layer of the light-emitting array. Distal to the wound bed, on the side of the light-emitting array that does not face the wound, a gas-impermeable member, for example, a drape or semi-occlusive dressing is used to seal the wound for NPWT.

In an embodiment the light-emitting array, for example, acts as a single "non-adherent" surface in a NPWT dressing. This allows for epithelization to occur without disrupting new growth. In an embodiment, the non-adherent light-emitting array provides anti-microbial light-based effects to the wound site and to the liquid, for example, exudate, disposed in or traveling throughout the pores of the device into a reservoir, for example, a reservoir comprising open-cell foam or gauze. The light from the light-emitting array can decrease the rate of colonization of bacteria and formation of biofilms in both the wound bed and adjacent materials that interact with the wound. Thus, in embodiments, wound healing, for example, the rate of wound healing, is optimized.

Some embodiments are discussed in more detail below.

Figure 22:
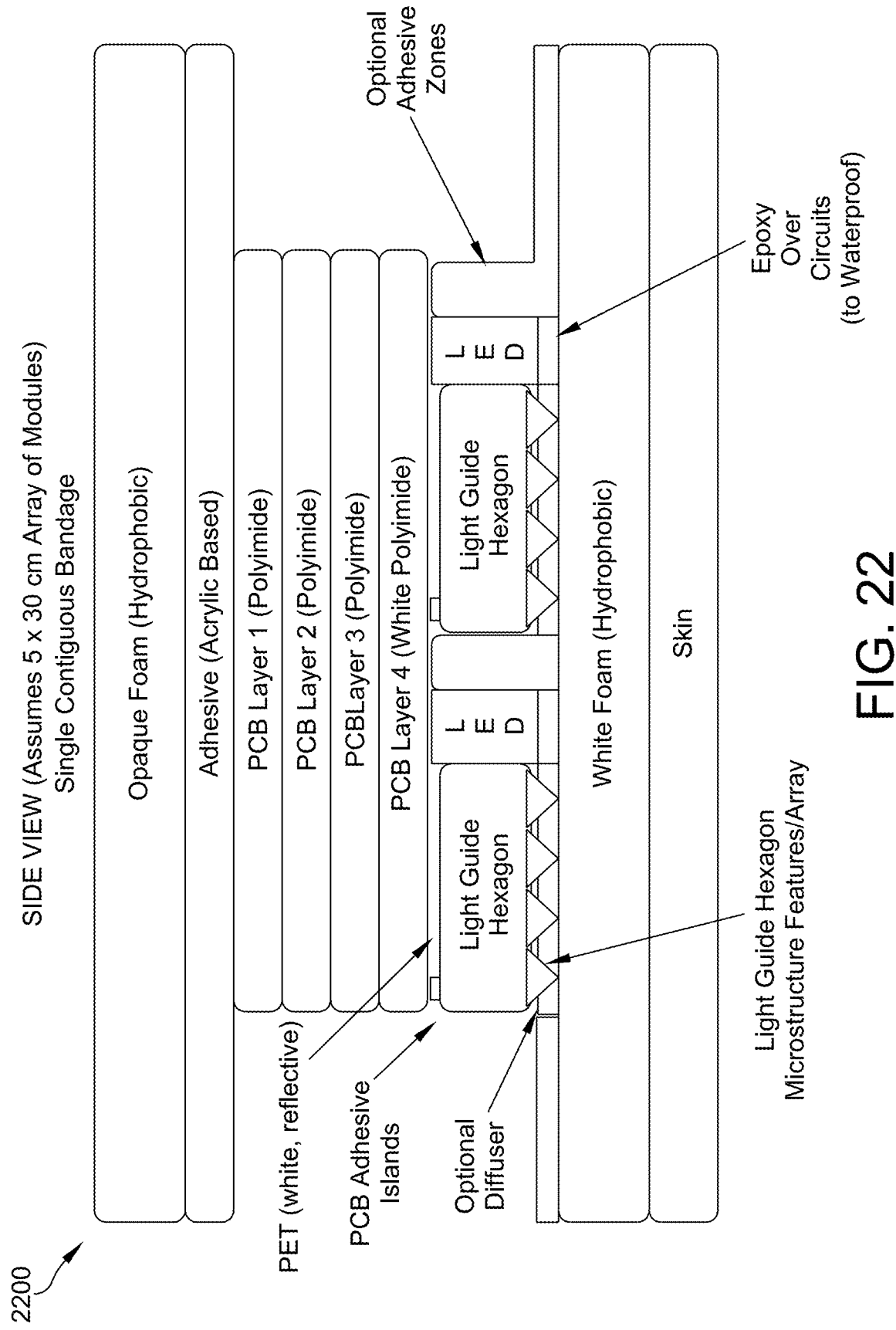
FIG. 22 depicts an example of a hexagon electronics and light guide array.
Figure 23:
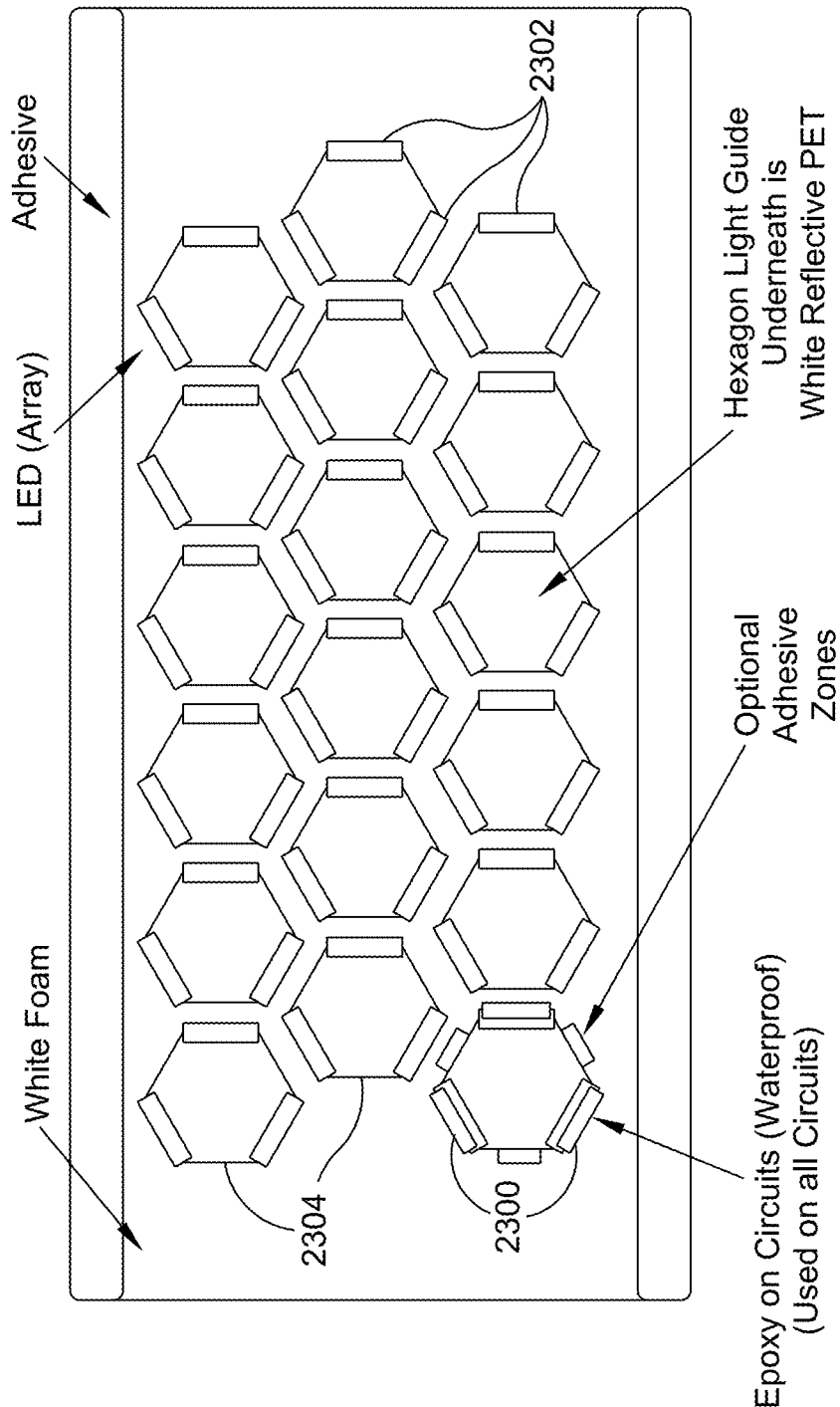
FIG. 23 depicts an example of the hexagon electronics and light guide array from a top view with the most immediate layers near the skin/wound.

FIGS. 22 and 23 show elements of an exemplary device 2200 from the side profile and top view, respectively. The hexagon light guide is discussed earlier, but the electronics include LEDs, LED drivers, resistors, and other electrical circuits reside on PCB layers with copper traces connecting the circuitry to an external power source. The PCB layers are typically made of polyimide of varying thicknesses from 10 microns to 1 millimeter or thicker, and the layers can be composed of varying color. A white layer is chosen where the hexagon light guide is positioned. This white layer could potentially be used as a white reflective substrate to bounce the light from the LEDs emitting light from a side of a hexagon light guide. The electronics and optics are kept in place with several strategic adhesive zones. The electronics and optics are sandwiched between various diffusers, reflectors, and foams which can be hydrophobic (repel fluids) or hydrophilic (absorb fluids).

In FIG. 23, the view is a top view; however the most immediate layer is nearest to the skin. An element that can be used instead of epoxy 2300 (green color rectangles labeled in FIG. 23) over the LEDs 2302 (LED array, yellow color rectangles labeled in FIG. 23) is either a white PET opaque material to cut down or reduce stray light coming from the side emitting LEDs which is not directly projected into the hexagon light guides 2304 (light blue colored hexagons labeled in FIG. 23). Alternatively, the epoxy can be substituted with a resin which can be transparent, or coated or embedded with a diffusive material like reflective glass or plastic beads (Cospheric Solid Soda Lime Glass Microspheres 2.5 g/cc d50~4 um—Uncoated) which can cut back on stray light but also allow the light to be equal in irradiance (or designer specific light output based on effective use case desire) to the irradiance at the center or non-LED array edge of the hexagon light guide arrays.

Figure 24:
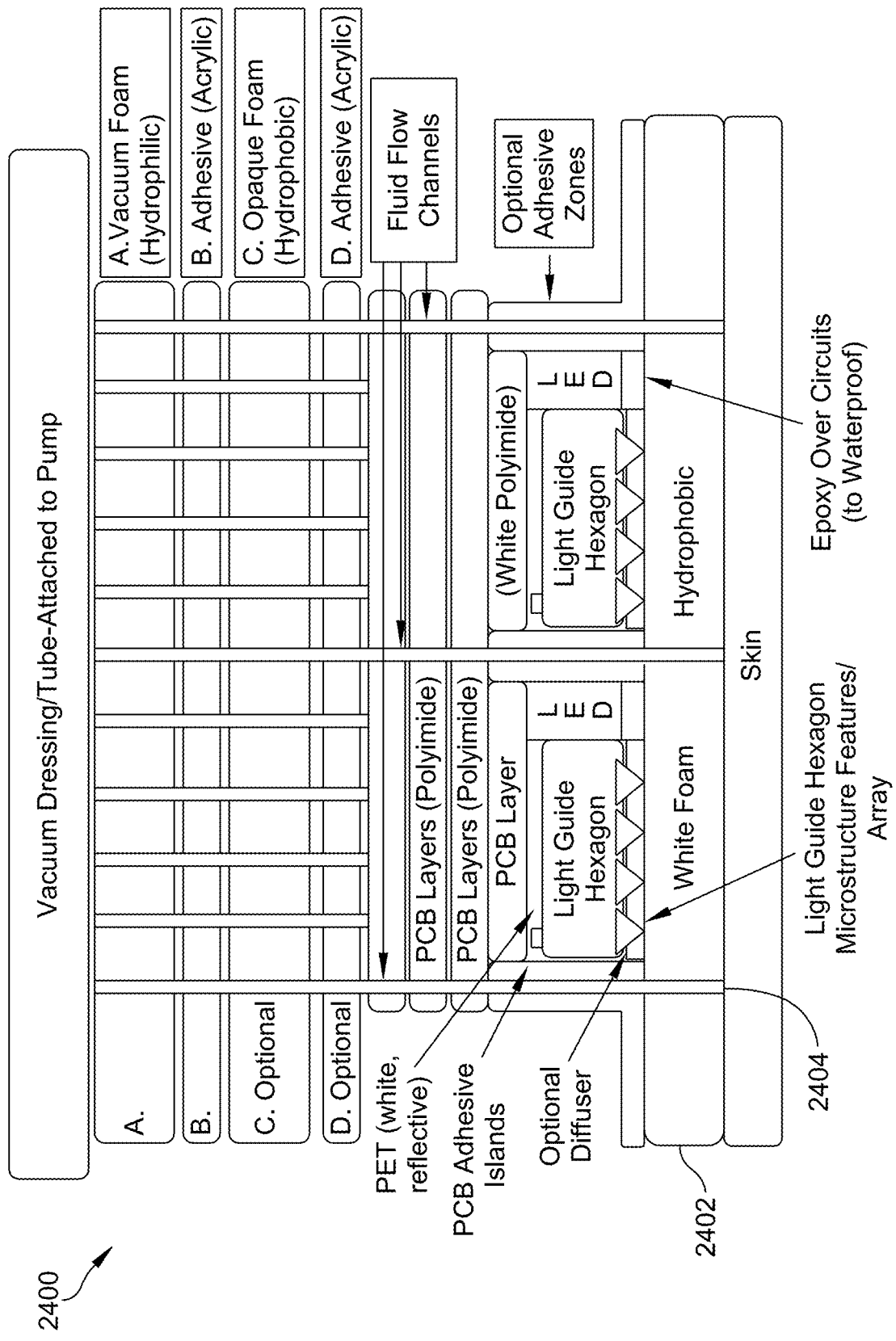
FIG. 24 depicts an example of a hexagon electronics and light guide array configured for use in a NPWT vacuum dressing.
Figure 25:
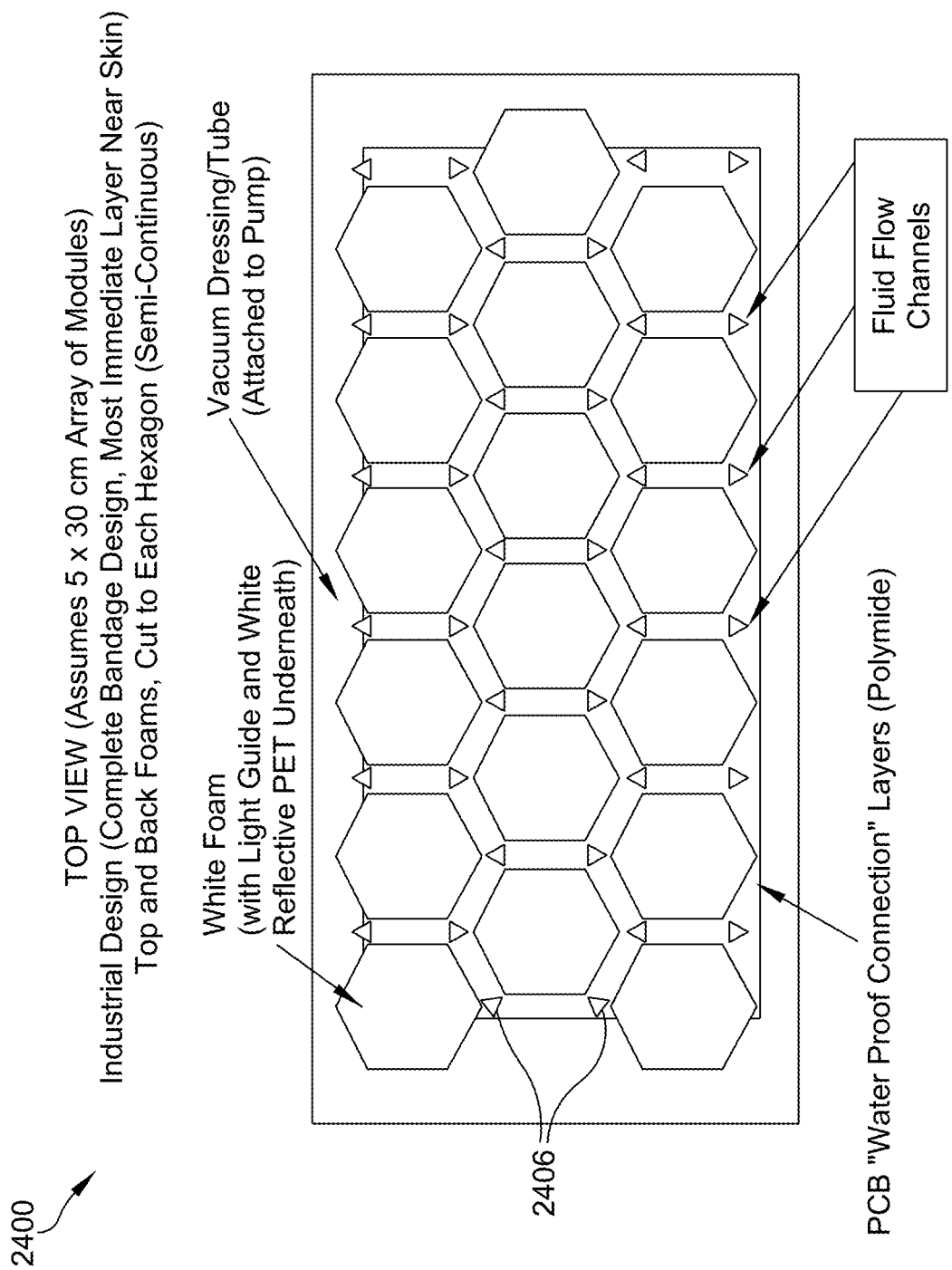
FIG. 25 depicts an example of a hexagon electronics and light guide array.

FIGS. 24 and 25 show a side and top view profile of an embodiment comprising a NPWT vacuum dressing 2400. All the electronic and optical components are water proofed and the most immediate layer making contact with the skin can be either hydrophobic or hydrophilic. An exemplary option is for the layers in direct contact with the top or bottom of the electronics and optics contain hydrophobic foam 2402 (see white foam layer by the skin and layer C. in FIG. 24). Fluid from the wound is wicked away or is directed through fluid flow channels 2404 (yellow channels shown in FIG. 24) which reside on the corners of adjacent hexagons 2406 (yellow channels shown in FIG. 25). In FIG. 24, Layer A is made of the typical NPWT hydrophilic foam, which takes in the fluid from the wound that has traveled past the hexagon electronics and light guide array. The vacuum dressing layer takes the fluid and transports it to the vacuum canister.

Figure 26:
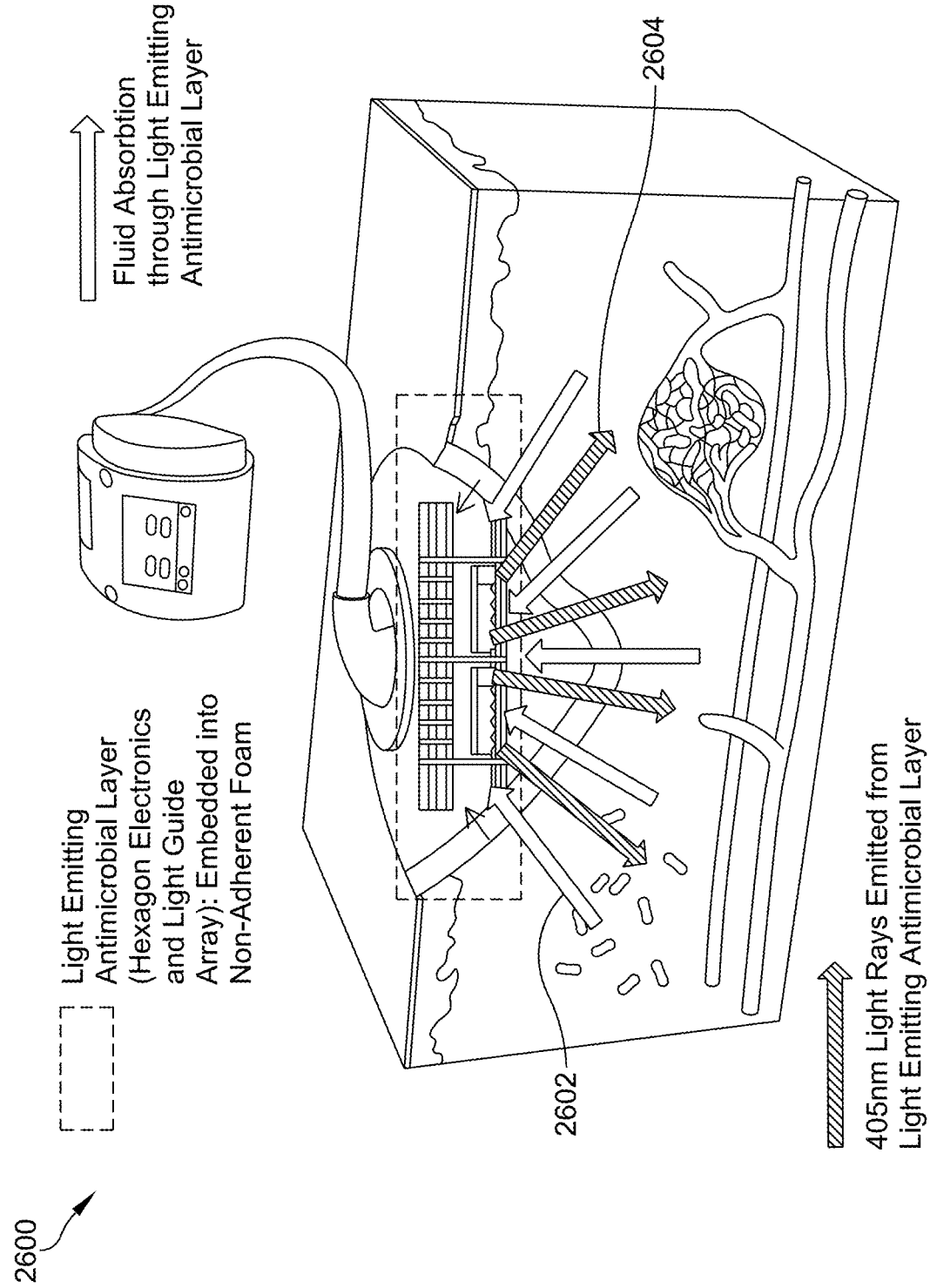
FIG. 26 depicts an example of a hexagon electronics and light guide array embedded with a NPWT vacuum dressing.

FIG. 26 shows an example application of the embedded hexagon electronics and light guide array 2600 (also referred to as the light-emitting antimicrobial layer) with the foam and semi-occlusive dressing in a NPWT vacuum dressing on an wound with fluids and exudate. Fluid 2602 (yellow arrows) flows into the dressing through the "Fluid Flow Channels" in the hexagon electronics and light guide array area up into the hydrophilic foam which is in direct contact with the tubing and section of the vacuum system. Simultaneously, the hexagon electronics and light guide array are projecting out light, quantified as irradiance, at various wavelengths, specifically 405 nm (+/−10 nm) into the wound bed 2604 (blue and white dotted arrows). The light acts as an antimicrobial, killing bacteria, fungi, spores, and other infectious-related substances and materials that impact wound healing.

In some embodiments discussed above, hexagon light guides and corresponding electronics layouts are described. Table 5 indicates exemplary design parameters for components of the hexagon light guides and corresponding electronics layouts described above.

TABLE 5

Exemplary Design Parameters

| PCB Thickness (mm) | Hexagon Maximal Width (mm) | Bend Radius of Curvature (mm) | Min. Air Gap (mm) | Max. Air Gap (mm) | LEDs Per Side | Spacing of LEDs | LED Half Angle (Deg.) |
|---|---|---|---|---|---|---|---|
| 1.6 | 5 | 25 | 1.22 | 3.41 | 1 | Equal | 55 |
| 1.6 | 5 | 50 | 1.11 | 3.30 | 1 | Equal | 55 |
| 1.6 | 5 | 100 | 1.05 | 3.24 | 1 | Equal | 55 |
| 1.6 | 5 | 250 | 1.02 | 3.21 | 1 | Equal | 55 |
| 1.6 | 20 | 25 | 1.75 | 2.75 | 3 | Equal | 55 |
| 1.6 | 20 | 50 | 1.43 | 2.43 | 3 | Equal | 55 |
| 1.6 | 20 | 100 | 1.22 | 2.22 | 3 | Equal | 55 |
| 1.6 | 20 | 250 | 1.09 | 2.09 | 3 | Equal | 55 |
| 1.6 | 50 | 25 | 2.56 | 5.24 | 5 | Equal | 55 |
| 1.6 | 50 | 50 | 1.95 | 4.64 | 5 | Equal | 55 |
| 1.6 | 50 | 100 | 1.53 | 4.22 | 5 | Equal | 55 |
| 1.6 | 50 | 250 | 1.22 | 3.90 | 5 | Equal | 55 |
| 0.8 | 5 | 25 | 1.14 | 3.33 | 1 | Equal | 55 |
| 0.8 | 5 | 50 | 1.07 | 3.26 | 1 | Equal | 55 |
| 0.8 | 5 | 100 | 1.03 | 3.22 | 1 | Equal | 55 |
| 0.8 | 5 | 250 | 1.01 | 3.20 | 1 | Equal | 55 |
| 0.8 | 20 | 25 | 1.48 | 2.48 | 3 | Equal | 55 |
| 0.8 | 20 | 50 | 1.27 | 2.27 | 3 | Equal | 55 |
| 0.8 | 20 | 100 | 1.14 | 2.14 | 3 | Equal | 55 |
| 0.8 | 20 | 250 | 1.06 | 2.06 | 3 | Equal | 55 |
| 0.8 | 50 | 25 | 1.99 | 4.68 | 5 | Equal | 55 |
| 0.8 | 50 | 50 | 1.61 | 4.30 | 5 | Equal | 55 |
| 0.8 | 50 | 100 | 1.34 | 4.02 | 5 | Equal | 55 |
| 0.8 | 50 | 250 | 1.14 | 3.83 | 5 | Equal | 55 |

EXAMPLES

Example 1: Methicillin-Resistant *Staphylococcus Aureus* Killing

Phase 1: The experimental setup of the study in Phase 1 involved cultures of methicillin-resistant *Staphylococcus aureus* (MRSA) suspended in Tryptic Soy Broth (TSB), and prepared to densities of 105 colony forming units per milliliter (CFU/mL), as confirmed through measurement of the solutions' optical densities (OD600), as well as through standard plate counts. Two hundred seventy-five microliters (275 µL) of the suspended cultures were loaded into each well of a 24-well microplate to receive light exposure. A total of four microplates were used in a given trial, wherein the microplates were randomly assigned to one of the following cohorts: (1) Control Microplate (Receiving No Light Treatment); (2) 75 J/cm$^2$ LIMB system delivered over 2 hours (10.44 mW/cm$^2$ irradiance); (3) 75 J/cm$^2$ LIMB delivered over 4 hours (5.22 mW/cm$^2$ irradiance); and (4) 75 J/cm$^2$ LIMB system delivered over 6 hours (3.48 mW/cm$^2$ irradiance). To ensure that each well within a given microplate was receiving identical irradiances, a THOR-LABS Optical Power Meter (Thor Laboratories, Newton, N.J.) was placed over each well to quantitate the exact irradiance being delivered. Throughout the course of this experiment, there were three separate trials conducted to ensure consistency and to evaluate both the intraplate and interplate bactericidal effects. During each trial, the optical density at 600 nm (OD600) of the cultures was recorded at baseline and following treatment. Additionally, fifty-microliter aliquots were taken from four randomly selected wells during those increments to be aseptically transferred onto Tryptic Soy Agar (TSA) plate using a Whitley Automated Spiral Plating system for analysis. Data throughout the course of this study was analyzed post-hoc using an ANOVA ($\alpha$=0.05) followed by a two-sided t-test. Each illumination condition was compared to both their control and accompanying experimental conditions. P values<0.05 were considered to be statistically significant.

Figure 13:
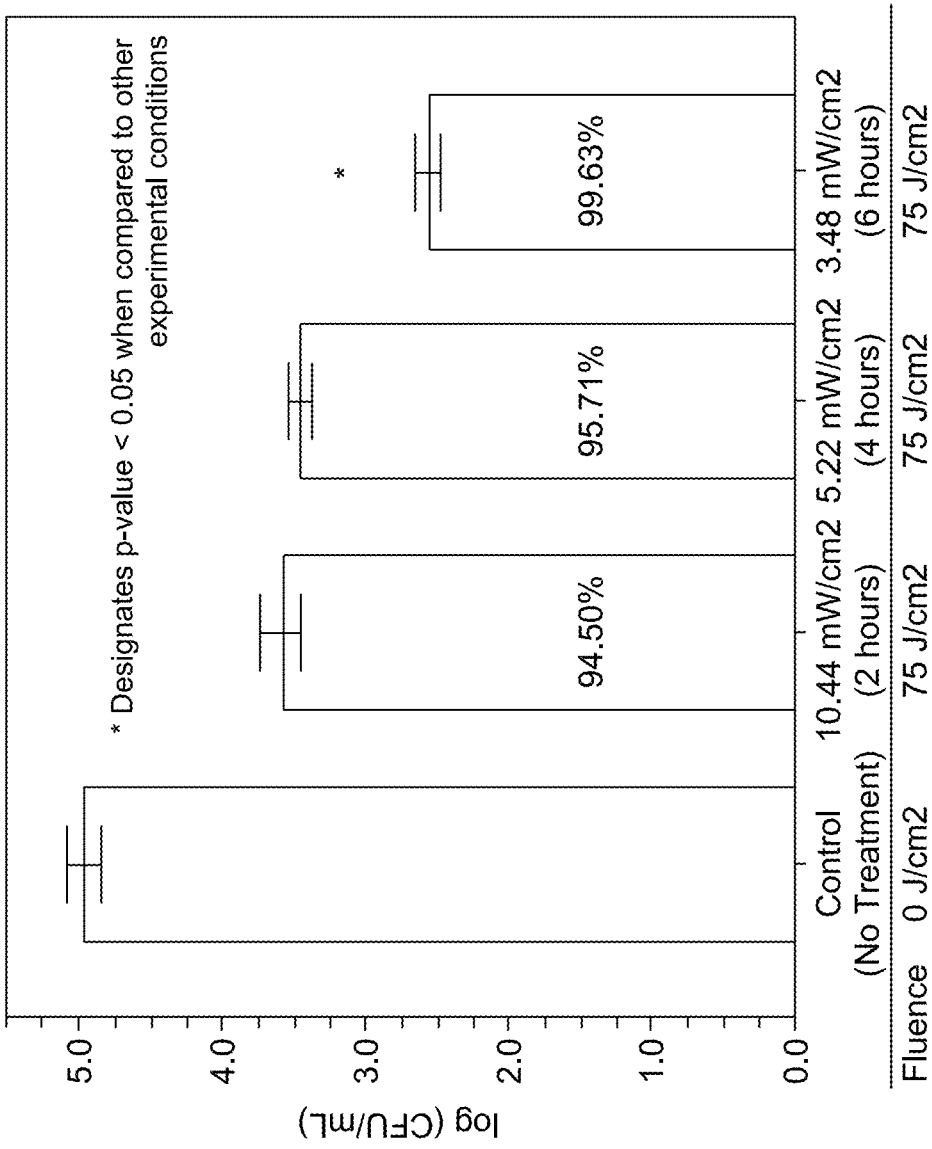
FIG. 13 illustrates a bar graph showing the viability of MRSA clinical isolates following exposure to 75 J/cm$^2$ LIMB system at varying irradiances and exposure durations.

FIG. 13 illustrates a chart 1300 which indicates viability of MRSA clinical isolates following exposure to 75 J/cm$^2$ LIMB system at varying irradiances and exposure durations. Statistical analysis was conducted post-hoc, and consisted of ANOVA and two-sided t-test. Asterisks identify statistically significant variance (P<0.05) when compared to both control and experimental conditions.

FIG. 13 indicates that there was a correlation associated with a greater bacterial load reduction when an identical fluence of 75 J/cm$^2$ 405-nm LLLT was administered at a lower irradiance and subsequently an increased exposure time. A statistically significant bacterial load reduction was observed when the irradiance was decreased from 10.44 mW/cm$^2$ and 5.22 mW/cm$^2$ (95.71% reduction) to 3.48 mW/cm$^2$ (99.63% reduction [p<0.004]).

Based on these statistically significant findings, the antimicrobial potential of the LIMB system further was evaluated by administering treatments over the course of 24 hours at irradiances reduced by as much as over 1000-fold compared to prior studies. Through this study, it was determined if there was a particular irradiance threshold of the LIMB system by exposing MRSA cultures to irradiances of: 145 µW/cm$^2$; 290 µW/cm$^2$; 580 µW/cm$^2$; 1.16 mW/cm$^2$ and 2.31 mW/cm$^2$. Through this matrix of conditions each culture received the LIMB system for 24 hours continuously. During each trial, the optical density at 600 nm (OD600) of the cultures was recorded at baseline and in 6-hour increments throughout the LIMB system treatment. Additionally, fifty-microliter aliquots were taken from four randomly selected wells during those six-hour increments to be aseptically transferred onto Tryptic Soy Agar (TSA) plate using a Whitley Automated Spiral Plating system for analysis. Data throughout the course of this study was analyzed post-hoc using an ANOVA (α=0.05) followed by a two-sided t-test. Each illumination condition was compared to both their control and accompanying experimental conditions. P values<0.05 were considered to be statistically significant.

Figure 14:
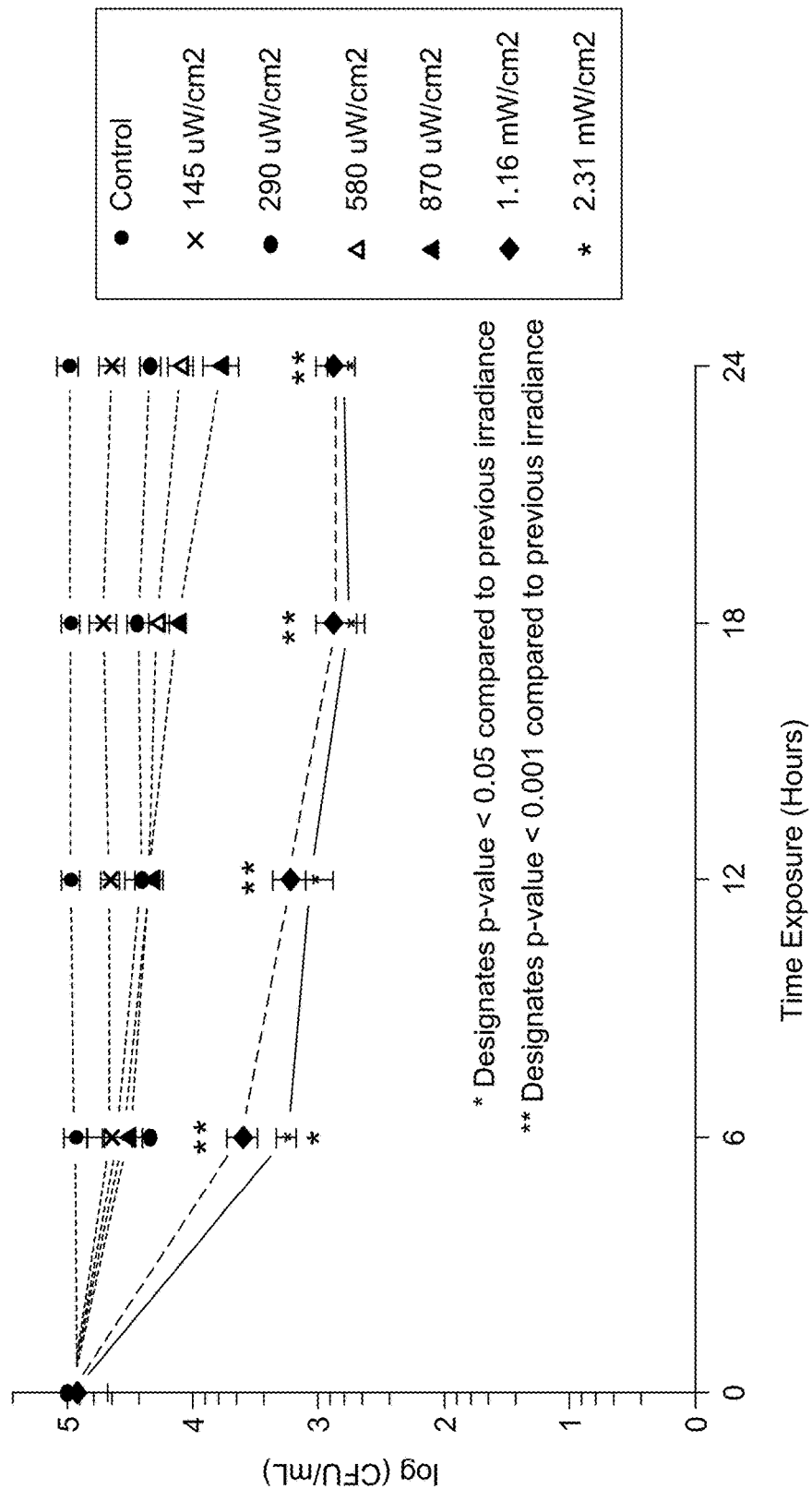
FIG. 14 illustrates a graph showing the viability of MRSA clinical isolates following exposure to the LIMB system continuously for 24 hours at varying irradiances.

FIG. 14 illustrates a chart 1400 which indicates the viability of MRSA clinical isolates following exposure to the LIMB system continuously for 24 hours at varying irradiances. Aliquots were collected from each treatment condition in 6-hour increments throughout the course of the 24 hour exposure periods. Statistical analysis was conducted post-hoc, and consisted of ANOVA and two-sided t-test. Asterisks identify statistically significant variance (P<0.05) when compared to both control and experimental conditions.

As illustrated in FIG. 14, continuous delivery of the LIMB system for 24 hours at each of the tested irradiances (145 µW/cm$^2$-2.31 mW/cm$^2$) provided a statistically significant reduction of MRSA bacterial density when compared to the control, untreated aliquots. In addition, it was determined as early as 6 hours across all three replicate trials, that there was a statistically significant (p<0.001) variation in the reduction of aliquots treated at 1.16 and 2.31 mW/cm$^2$ among the other irradiance ranges, respectively. This finding suggests that there is potentially a discrete range for continuous LIMB system delivery, and that irradiances below said range could demonstrate limited antimicrobial efficacy. Therefore, based on initial criteria, the lowest-irradiance to administer an antimicrobial LIMB system and achieve a minimum of 99.0% bacterial load reduction was 1.16 mW/cm$^2$.

Upon completion of Phase 1, a discrete dose-range can be optimized in Phase 2 to deliver a minimum 2.0 log (99.0%) bacterial load reduction within a single LIMB system treatment of the following multidrug-resistant organisms (MDROs): MRSA, *Pseudomonas aeruginosa* (*P. aeruginosa*), carbapenem-resistant *Klebsiella pneumoniae* (CRE), New Delhi metallo-beta-lactamase *K. pneumoniae* (NDM-1) and Vancomycin-resistant *Enterococcus faecium* (VRE).

To validate the antimicrobial effects of LIMB system at this particular dosimetry for both Gram Positive and Gram Negative MDROs, samples of *P. aeruginosa* were first treated under the identical parameters outlined in FIG. 14 and observed a bacterial load reduction of 99.21% [p<0.001 compared to control species] at irradiances as low as 1.16 mW/cm$^2$.

Following this procedure, the bactericidal properties of LIMB system on each of the aforementioned MDROs can be investigated at irradiances ranging from 2.78 mW/cm$^2$-8.33 mW/cm$^2$ (at fluences ranging between 240-720 J/cm$^2$) delivered over a period of 24 hours.

Example 2: Inhibition of MDRO Colonization

Two hundred microliter (200 µL) aliquots of overnight cultures of *P. aeruginosa* suspended in Tryptic Soy Broth (at cell density of 105 CFU/mL) were loaded into individual wells of a Corning® clear bottom 96-well microplate (n=48 wells per organism per plate). Following bacterial seeding, each microplate was transferred into an incubator at 37° C. and 5% $CO_2$ to allow for optimal bacterial growth conditions. Within each given trial, there were 5 microplates used. Each microplate was randomly assigned to one of the following conditions within the incubator: (1) Control plate (receiving no intervention); (2) 60 J/cm$^2$ LIMB system exposure over 24 hours; (3) 120 J/cm$^2$ LIMB system exposure over 24 hours; (4) 240 J/cm$^2$ LIMB system exposure over 24 hours; and (5) 5.0 mg/L Ciprofloxacin over 24 hours. The LIMB system was delivered below each microplate via a light emitting system with an appropriate heat sink of an embodiment of the disclosure, and was designed ensure light uniformity across the course of a given treatment. All treatment parameters were repeated in triplicates to demonstrate intraplate and interplate consistency.

The rate of bacterial growth and biofilm formation of each experimental cohort was evaluated at both 18 and 24 hours into therapy. The rate of biofilm formation was completed using a Crystal Violet assay, as described by O'Toole. Bacterial growth was monitored using serial dilutions and plating 10 µL aliquots of each experimental parameter on Cetrimide Agar plates using the Track Dilution Plating Method to determine bacterial density (CFU/mL). In order to account for biofilm encapsulated organisms, each well plate was placed on a microplate shaker at 800 rpm for 10 minutes to ensure mechanical disruption of the biofilm prior to aliquot collection.

Figure 15:
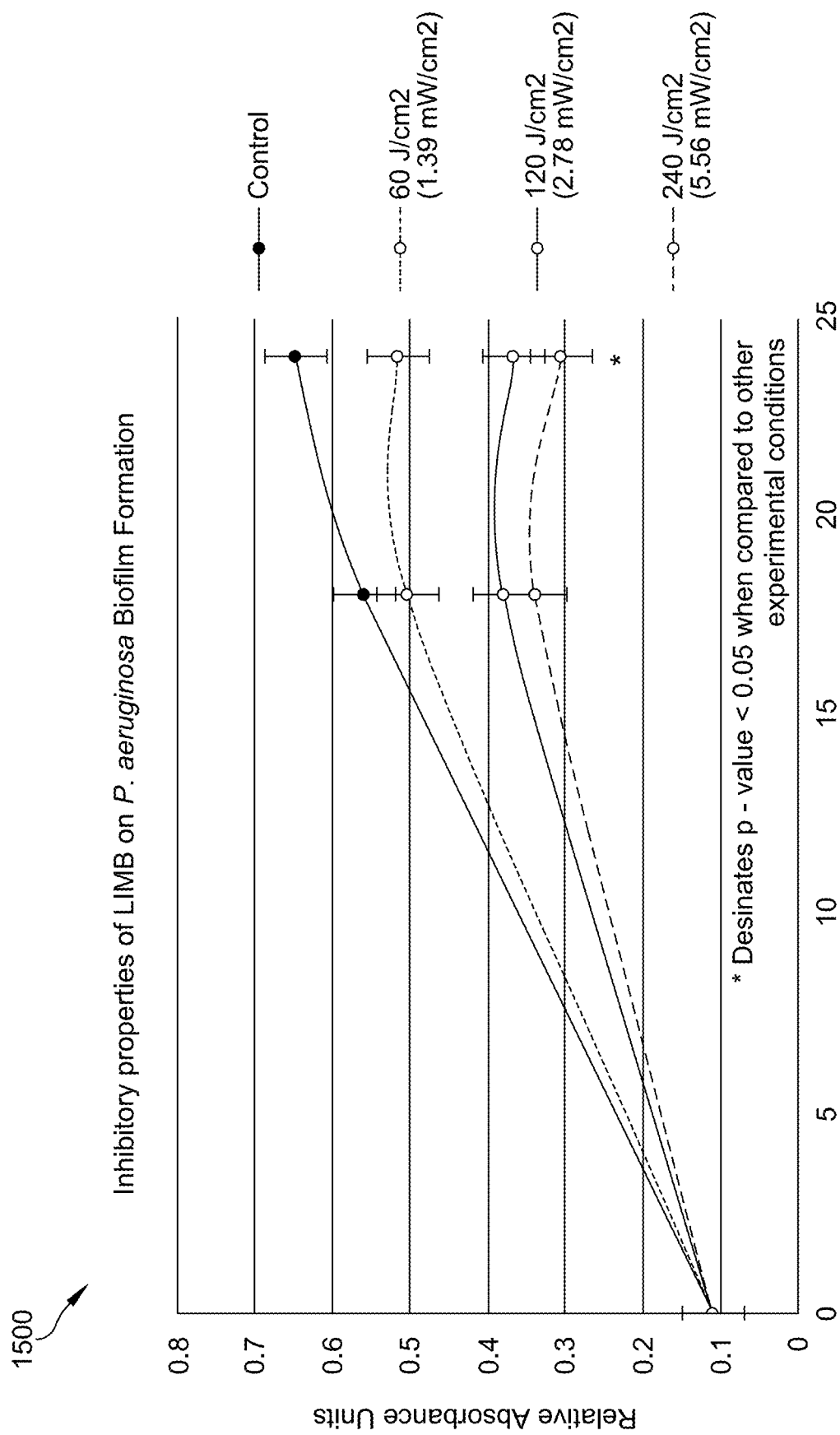
FIG. 15 illustrates a graph showing the delivery of a single cycle of 405 nm LIMB system over a 24 hour time period at irradiances of 1.39 mW/cm$^2$, 2.78 mW/cm$^2$, and 5.56 mW/cm$^2$ on cultures of P. aeruginosa in growth conditions of 37° C. and 5% $CO_2$.

FIG. 15 illustrates a graph 1500 indicating delivery of a single cycle of 405 nm LIMB system over a 24 hour time period at irradiances of 1.39 mW/cm$^2$, 2.78 mW/cm$^2$, and 5.56 mW/cm$^2$ on cultures of *P. aeruginosa* in growth conditions of 37° C. and 5% $CO_2$. A crystal violet stain was completed on the cultures throughout the course of treatment to demonstrate the formation of microbial biofilms. Assay performed: Crystal Violet Stain.

Figure 16:
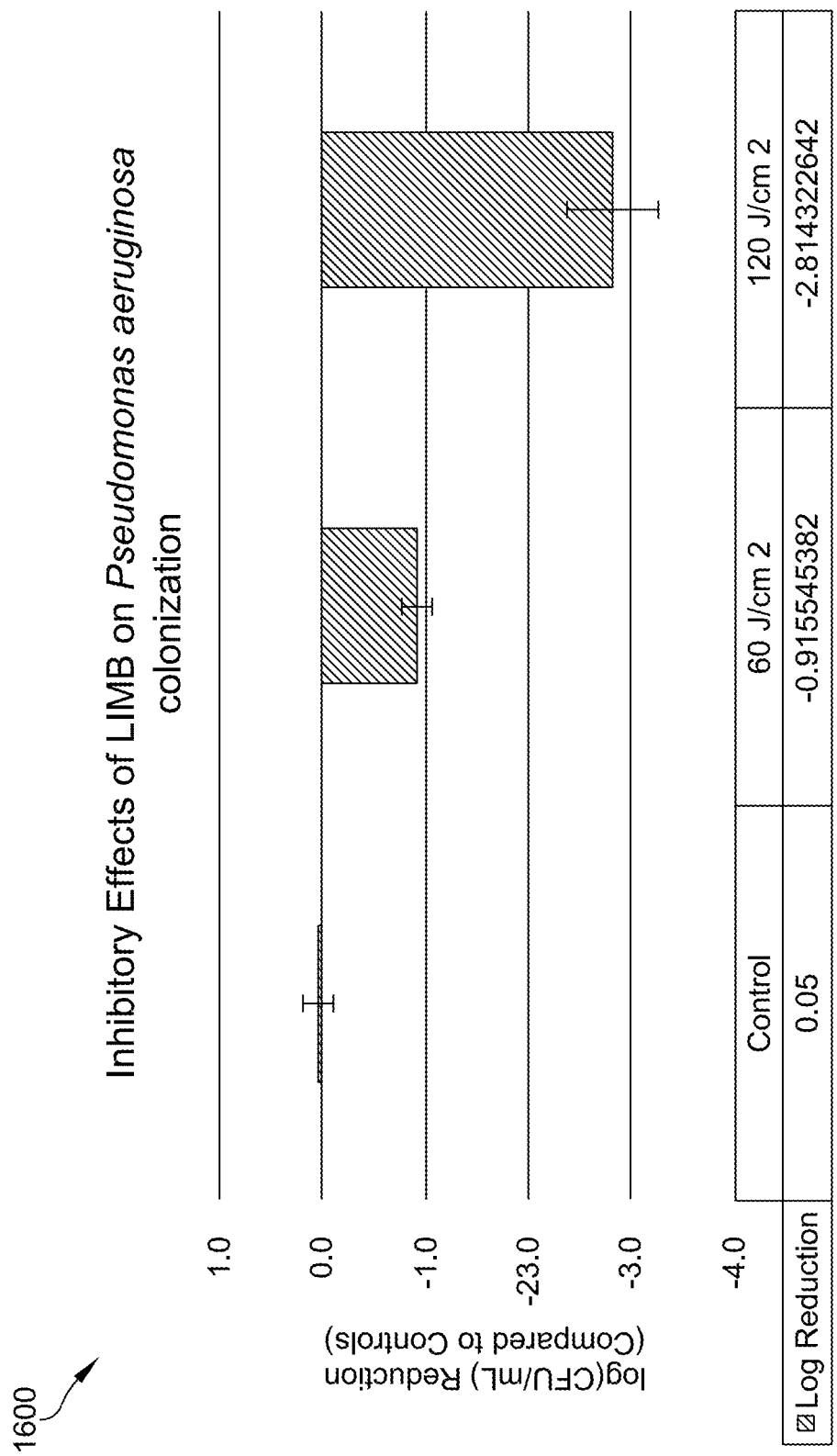
FIG. 16 illustrates graph showing the delivery of a single 24-hour cycle of LIMB system at fluences of: 60 J/cm$^2$; 120 J/cm$^2$ and 240 J/cm$^2$, and exposure to ciprofloxacin (5 mg/L) on cultures of P. aeruginosa in growth conditions of 37° C. and 5% $CO_2$.

FIG. 16 illustrates a chart 1600 indicating a delivery of a single 24-hour cycle of LIMB system at fluences of: 60 J/cm$^2$; 120 J/cm$^2$ and 240 J/cm$^2$, and exposure to ciprofloxacin (5 mg/L) on cultures of *P. aeruginosa* in growth conditions of 37° C. and 5% $CO_2$. Aliquots were collected upon completion of treatment, and were analyzed using sonication and serial dilution to determine the percent reduction of viable *P. aeruginosa* organisms in both control and treated-samples.

As illustrated in FIGS. 15 and 16, delivery of the LIMB system at varying irradiances to planktonic cultures of *P. aeruginosa* for 24 hours provided a statistically significant inhibition of bacterial colonization (>99.0% reduction) and biofilm density when compared to the control, untreated aliquots (p<0.05). In addition, it was determined that administration of the LIMB system at higher energy levels (240 J/cm$^2$) provided a statistically similar antimicrobial response as Ciprofloxacin (p>0.10) in regards to biofilm formation and bactericidal properties. These finding suggests that administration of the LIMB system holds the potential to delay the onset of bacterial colonization and biofilm formation through a mechanism with comparable efficacy to clinical relevant antibiotic agents.

Example 3: Reduction and Elimination of Biofilms in Wounds

Two hundred microliter (200 µL) aliquots of overnight cultures of *P. aeruginosa* suspended in Tryptic Soy Broth (at cell density of 105 CFU/mL) were loaded into individual wells of a Corning® clear bottom 96-well microplate (n=48 wells per organism per plate). Following bacterial seeding, each microplate was transferred into an incubator at 37° C. and 5% $CO_2$, and was allowed to grow under static conditions for either 24 or 48 hours. Prior to initiation of the LIMB system or Ciprofloxacin exposure, the growth media from each biofilm was discarded, and the biofilms were carefully rinsed with 200 µL phosphate buffered saline (PBS).

Within each given trial, there were 5 microplates used. Each microplate was randomly assigned to one of the following conditions after growing for 24 hours: (1) Control plate (receiving no intervention); (2) 120 J/cm$^2$ LIMB system exposure over 24 hours; (3) 240 J/cm$^2$ LIMB system exposure over 24 hours; (4) 360 J/cm$^2$ LIMB system exposure over 24 hours; and (5) 5.0 mg/L Ciprofloxacin over 24 hours. The LIMB system was delivered below each microplate via a light emitting system with an appropriate heat sink developed, and was designed ensure light uniformity across the course of a given treatment. All treatment parameters were repeated in triplicates to demonstrate intraplate and interplate consistency.

The rate of bacterial growth and biofilm formation of each experimental cohort was evaluated at both 18 and 24 hours into therapy. The rate of biofilm formation was completed using a Crystal Violet assay, as described by O'Toole. Bacterial growth was monitored using serial dilutions and plating 10 µL aliquots of each experimental parameter on Cetrimide Agar plates using the Track Dilution Plating Method to determine bacterial density (CFU/mL). In order to account for biofilm encapsulated organisms, each well plate was placed on a microplate shaker at 800 rpm for 10 minutes to ensure mechanical disruption of the biofilm prior to aliquot collection.

FIG. 1700 illustrates a graph 1700 which indicates delivery of a single cycle of 405 nm LIMB system over a 24 hour time period at fluences of 120 J/cm$^2$; 240 J/cm$^2$ and 360 J/cm$^2$ on *P. aeruginosa* biofilms previously grown for 24 hours at 37° C. and 5% $CO_2$. The LIMB system exposure was completed at room temperature. A crystal violet stain was completed on the cultures throughout the course of treatment to demonstrate the remaining fraction of microbial biofilms.

Figure 18:
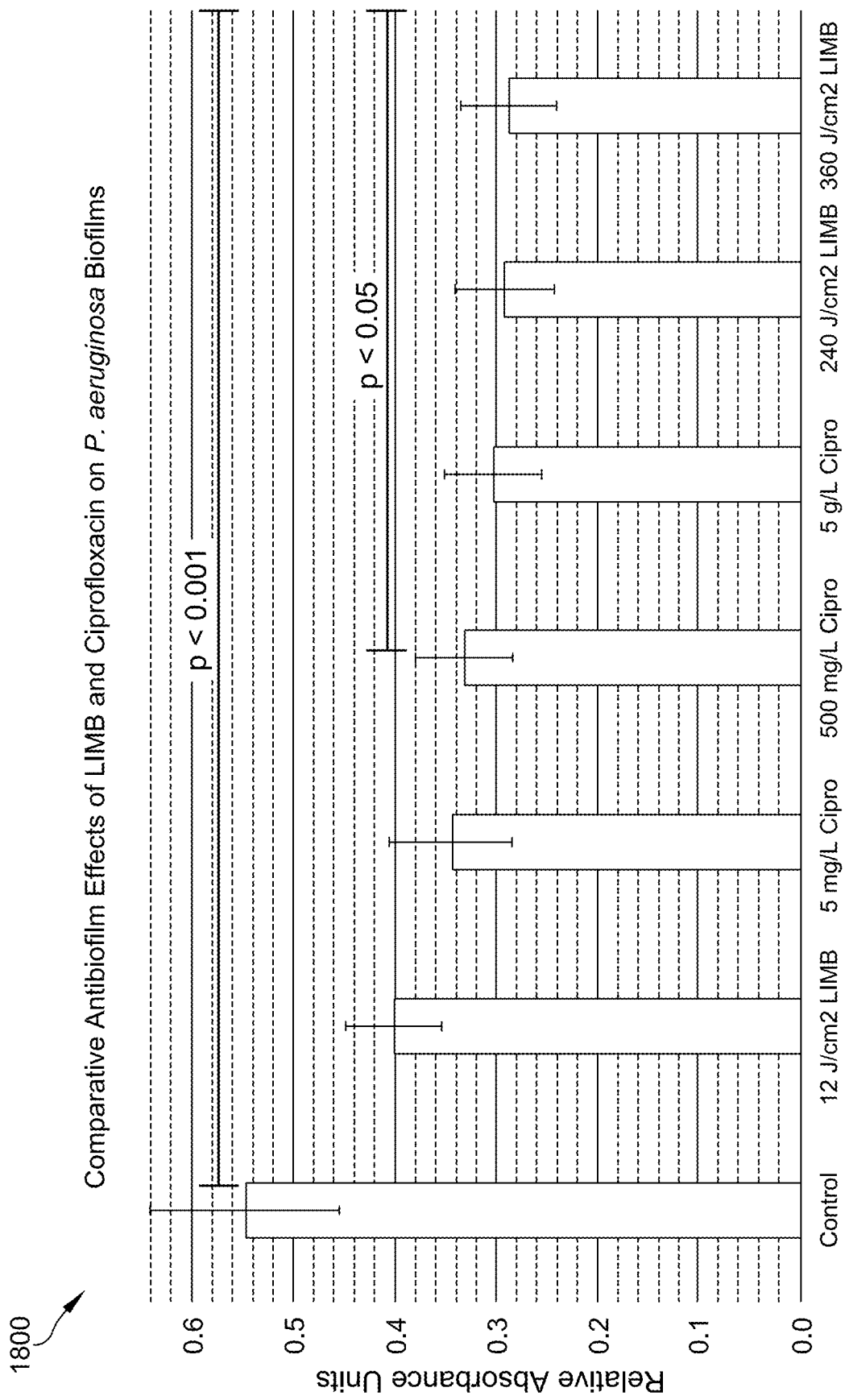
FIG. 18 illustrates the delivery of a single cycle of the LIMB system over a 24 hour time period at fluences of 120 J/cm$^2$; 240 J/cm$^2$; and 360 J/cm$^2$, as well as ciprofloxacin concentrations of 5 mg/L; 500 mg/L; and 5 g/L on P. aeruginosa biofilms previously grown for 24 hours at 37° C. and 5% $CO_2$.

FIG. 18 illustrates a chart 1800 indicating delivery of a single cycle of the LIMB system over a 24 hour time period at fluences of 120 J/cm$^2$; 240 J/cm$^2$; and 360 J/cm$^2$, as well as ciprofloxacin concentrations of 5 mg/L; 500 mg/L; and 5 g/L on *P. aeruginosa* biofilms previously grown for 24 hours at 37° C. and 5% $CO_2$. The LIMB system exposure was completed at room temperature. A crystal violet stain was performed upon completion of each condition to demonstrate the remaining fraction of microbial biofilms. Statistical analysis was conducted post-hoc, and consisted of ANOVA and two-sided t-test.

Figure 17:
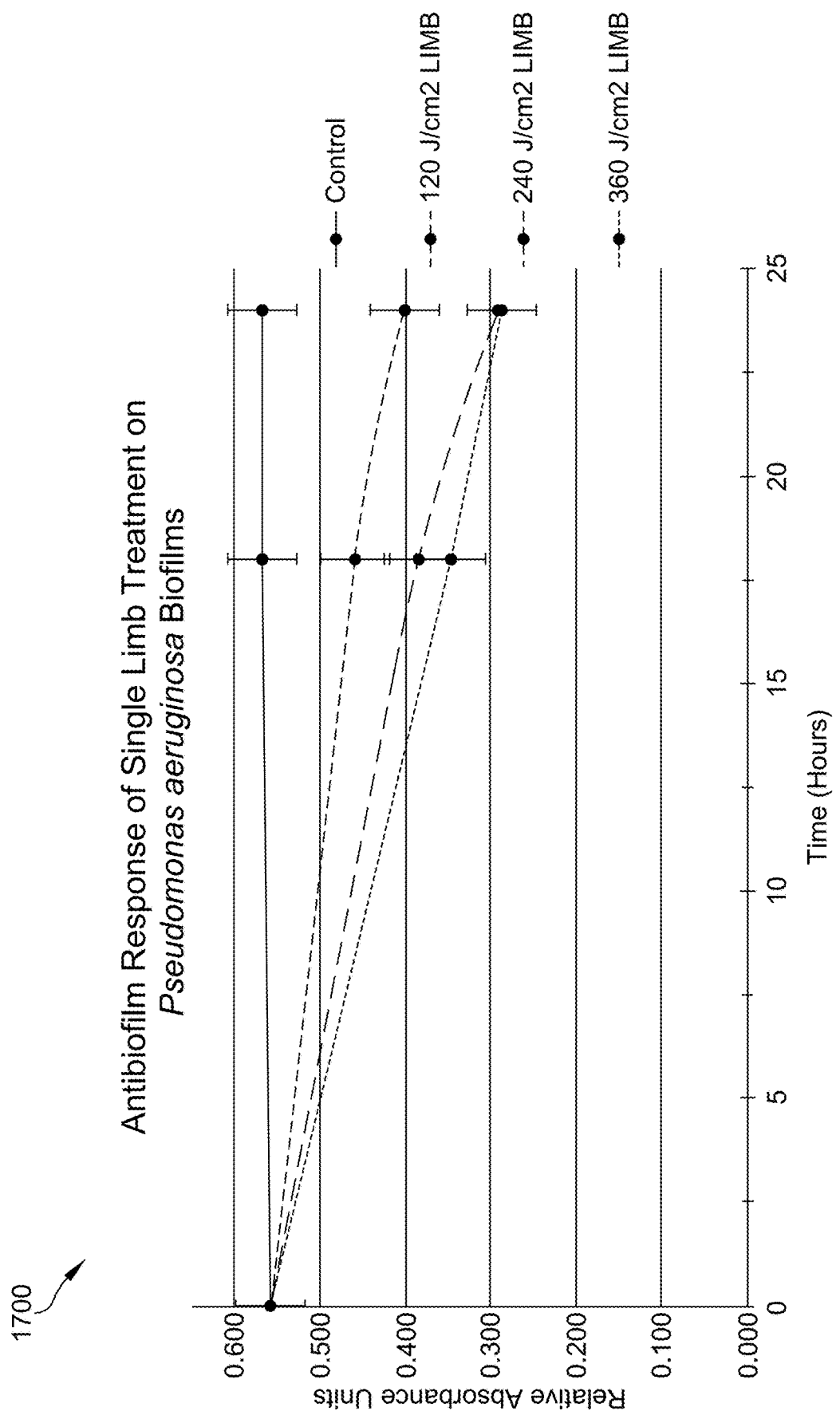
FIG. 17 illustrates a bar graph showing the delivery of a single cycle of 405 nm LIMB system over a 24 hour time period at fluences of 120 J/cm$^2$; 240 J/cm$^2$ and 360 J/cm$^2$ on P. aeruginosa biofilms previously grown for 24 hours at 37° C. and 5% $CO_2$.

FIGS. 17 and 18 demonstrate the antimicrobial properties of the LIMB system in comparison to Ciprofloxacin therapy following 24 hour exposure at varying treatments. It was also determined in FIG. 18 that significant variance (p<0.001) was observed among control biofilms and all experimental conditions. Furthermore, significant variance (p<0.05) was observed when comparing 500 mg/L ciprofloxacin treated biofilms to when compared to biofilms treated with 5 g/L ciprofloxacin and 240 and 360 J/cm$^2$ LIMB system, respectively.

Example 4: Disruption of Biofilms

Two hundred microliter (200 µL) aliquots of overnight cultures of *P. aeruginosa* or MRSA suspended in Tryptic Soy Broth (at cell density of 105 CFU/mL) were loaded into individual wells of a Corning® clear bottom 96-well microplate (n=24 wells per organism per plate). Following bacterial seeding, each microplate was transferred into an incubator at 37° C. and 5% $CO_2$ to allow for optimal bacterial growth conditions. Within each given trial, there were 2 microplates used. Each microplate was randomly assigned to one of the following conditions within the incubator: (1) Control plate (receiving no intervention); (2) LIMB system exposure over 24 hours. The LIMB system was delivered below each microplate via a light-emitting system with an appropriate heat sink developed, and was designed to ensure light uniformity across the course of a given treatment. All treatment parameters were repeated in triplicates to demonstrate intraplate and interplate consistency. All images were evaluated using a FilmTracer LIVE/DEAD® Biofilm Viability Kit (Invitrogen) upon completion of the exposure periods, and were quantitatively analyzed using the program Comstat 2.1 through ImageJ.

Figure 19:
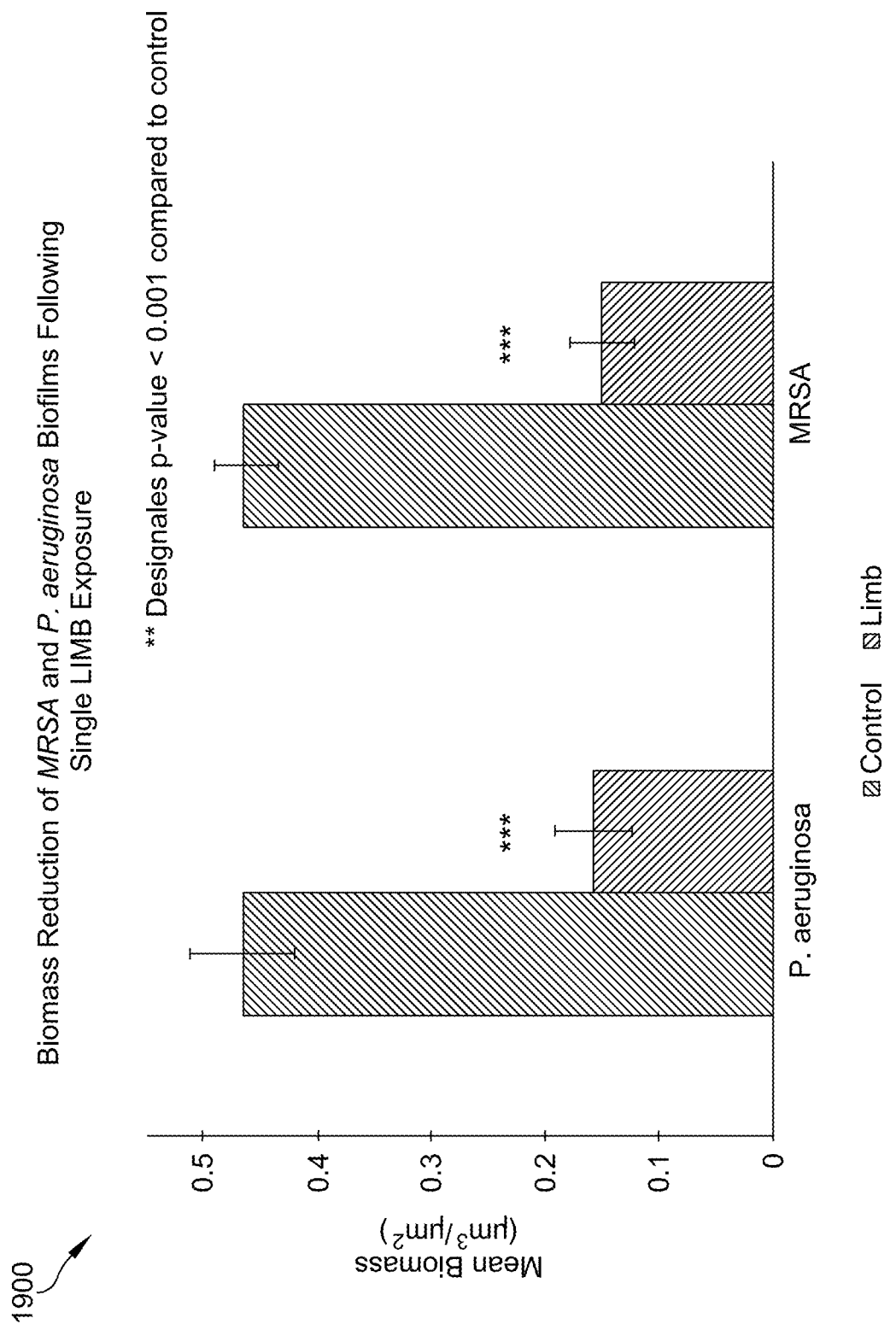
FIG. 19 illustrates the quantitative analysis of Live/Dead Confocal Microscopy Staining of mature P. aeruginosa and MRSA biofilms exposed to a single LIMB system treatment over 18 hours.

FIG. 19 illustrates a chart 1900 indicating quantitative analysis of Live/Dead Confocal Microscopy Staining of mature *P. aeruginosa* and MRSA biofilms exposed to a single LIMB system treatment over 18 hours. Mean Biomass ratios were collecting using the biofilm analysis software Comstat 2.1®, and this ratio serves as a direct measurement of presence of live and intact microbial biofilms.

Figure 20:
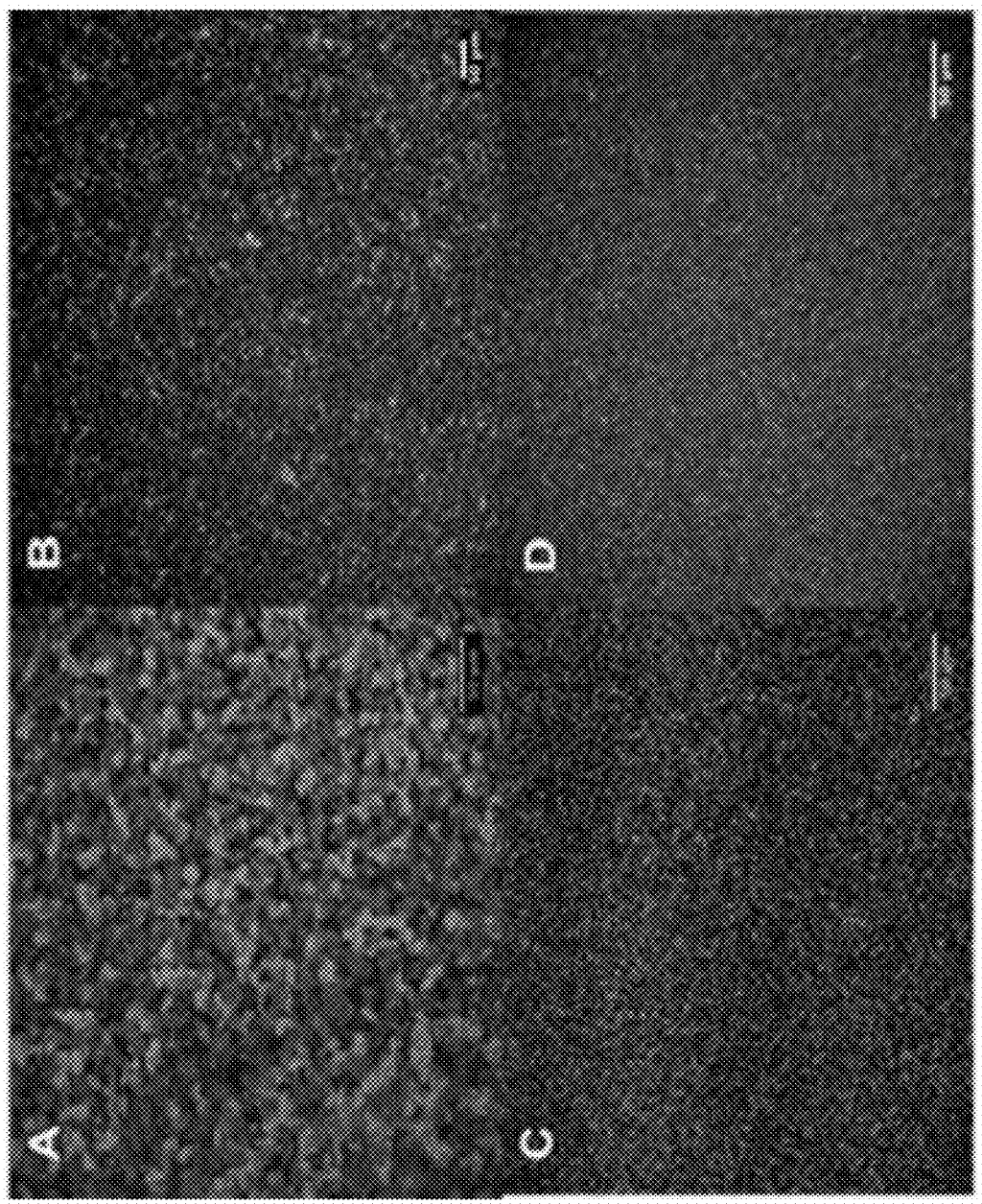
FIG. 20 illustrates a Live/Dead Staining Assay of MRSA (A-B) and P. aeruginosa (C-D) following LIMB system treatment. A) MRSA and C) P. aeruginosa Control Groups, Receiving Sham Light Treatment; B) MRSA and D) P. aeruginosa following the LIMB system over 18 hours. (Green indicates intact cell membrane and Red indicates damaged/lysed membranes.)

FIG. 20 illustrates an image 2000 of a Live/Dead Staining Assay of MRSA (A-B) and *P. aeruginosa* (C-D) following LIMB system treatment. A) MRSA and C) *P. aeruginosa* Control Groups, Receiving Sham Light Treatment; B) MRSA and D) *P. aeruginosa* following the LIMB system over 18 hours. (Green indicates intact cell membrane and Red indicates damaged/lysed membranes).

FIG. 19 demonstrates that a single treatment of the LIMB system provided a statistically significant reduction (p<0.01) in microbial biomass when compared to control, non-illuminated biofilms. These findings, derived from confocal analysis illustrated in FIG. 8, support the underlying mechanism of action of the LIMB system, and suggest that the LIMB system's capabilities to penetrate through microbial biofilms can serve as a promising adjuvant to conventional antibiotics rendered otherwise ineffective in biofilms.

To further evaluate this theory, a matrix of three discrete LIMB system doses (240 J/cm² [irradiance 2.78 mW/cm²]; 240 J/cm² [irradiance 5.56 mW/cm² and 480 J/cm² [5.56 mW/cm²]) was delivered in conjunction with varying concentrations of Ciprofloxacin (5 μg/mL; 0.5 mg/mL and 5 mg/mL) on *P. aeruginosa* biofilms.

Figure 21:
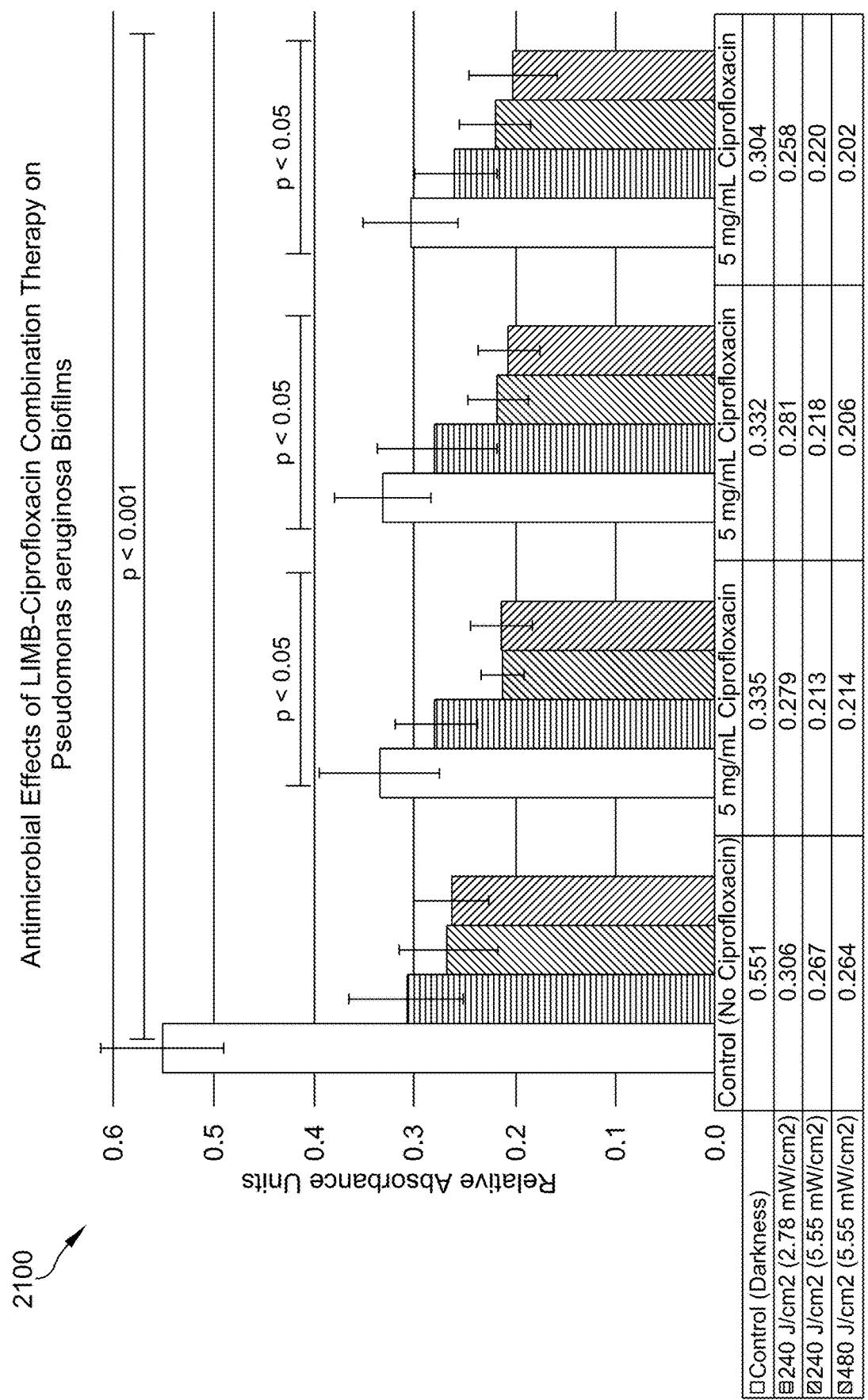
FIG. 21 illustrates delivery of a single cycle of 405 nm LIMB system over a 24 hour time period at fluences of 240 J/cm$^2$; and 480 J/cm$^2$ in the presence and absence of Ciprofloxacin on P. aeruginosa biofilms previously grown for 24 hours at 37° C. and 5% $CO_2$.

FIG. 21 illustrates a chart 2100 indicating a delivery of a single cycle of 405 nm LIMB system over a 24 hour time period at fluences of 240 J/cm²; and 480 J/cm² in the presence and absence of Ciprofloxacin on *P. aeruginosa* biofilms previously grown for 24 hours at 37° C. and 5% $CO_2$. The LIMB system exposure was completed at room temperature. A crystal violet stain was completed on the cultures to demonstrate the remaining fraction of microbial biofilms. Statistical analysis was conducted post-hoc, and consisted of ANOVA and two-sided t-test. Asterisks identify statistically significant variance ($p<0.05$ or $p<0.001$) when compared to both control and experimental LIMB system conditions within a given Ciprofloxacin cohort.

FIG. 21 demonstrates that across each Ciprofloxacin concentration employed, there was a statistically significant ($p<0.05$) reduction of *P. aeruginosa* biofilm at all three discrete LIMB system fluences.

Discussion will now be directed to light guides and Light Guide Films (LGFs). A light guide or LGF is a device designed to transport light from a light source to a point at some distance with minimal loss. Light is transmitted through a light guide by means of total internal reflection (TIR). Light guides are usually made of optical grade materials such as acrylic resin, polycarbonate, epoxies, and glass. A light guide can be used to transmit light from an LED lamp on a Printed Circuit Board (PCB) to a front panel for use as status indication, can be used to collect and direct light to backlight an LCD display or legend, and can be used as the means to illuminate a grid pattern on a see-through window. For the purposes of certain products, the LGF is used to create precision Light Emitting Surfaces (LES) to deliver exact, within +/−20% of the mean irradiance (mW/cm²), uniform light of one or more wavelengths to a therapy site. Uniformity is crucial to guarantee all locations in the treatment site receive identical illumination and reduce variability in treatment and treatment outcomes.

Light delivery in a LGF is achieved similar to the principal behind LED edge-lit displays. In short, LEDs are placed in a sideways orientation and coupled to a thin, optically clear material with a surface pattern design to extract light in a specific way from the material.

Figure 27:
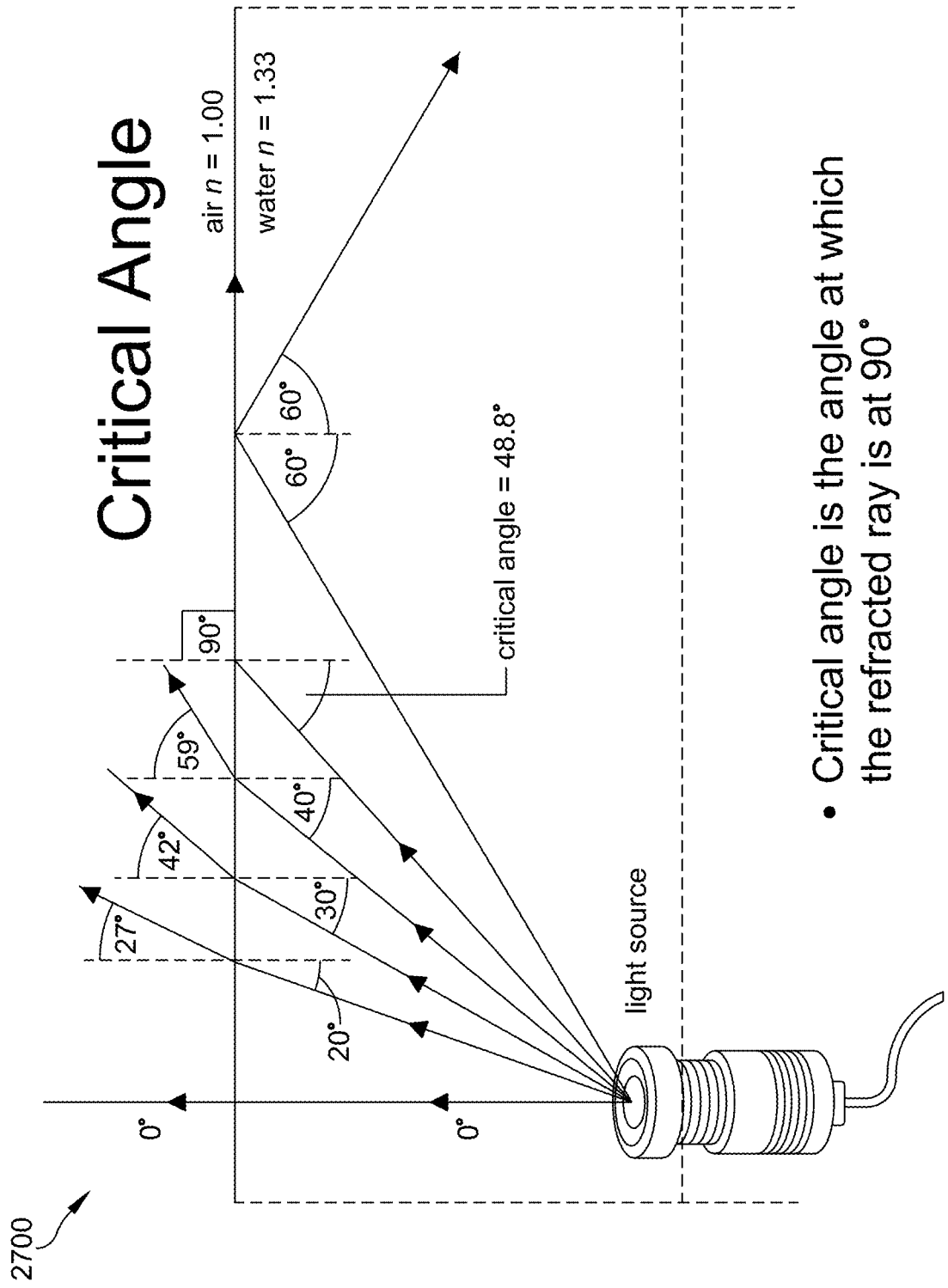
FIG. 27 depicts an example of a schematic diagram illustrating light behavior at a material boundary.

One feature of light delivery through an LGF is taking advantage of TIR and the critical angle where light within a higher index of refraction medium or material is surrounded by a lower index of refraction medium or material. For example, FIG. 27 illustrates a schematic diagram 2700 illustrating light behavior at a material boundary. As illustrated by FIG. 27, the higher index of refraction medium is water surrounded by the lower index of refraction medium of air.

When light traveling through the higher index of refraction material hits the boundary of the material at an angle less than the critical angle, the light primarily refracts out of the material into the lower index of refraction material. If the light hits this boundary at an angle greater than the critical angle, the light total internally reflects within the higher index of reflection material, as if the boundary of the material acts like a mirror, where the light reflects at the same angle as when it hit the material boundary.

The critical angle ($f_c$) can be determined using Equation 1, $$\sin f_c = \frac{n_f}{n_i} \tag{1}$$

where $n_f$ is the low (typically outside) index of refraction material and $n_i$ is the high index of refraction material.

Figure 28:
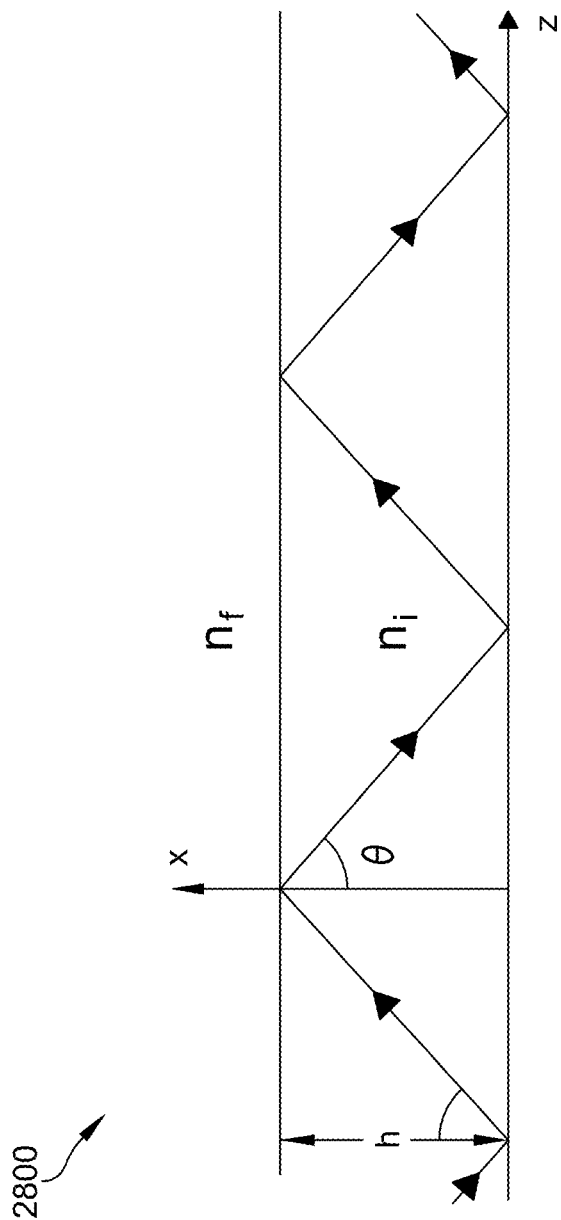
FIG. 28 depicts an example of a schematic diagram of TIR conditions where $n_f < n_i$.

Once light within the higher index of refraction material has met the TIR condition from having an angle larger than the critical angle, this light can be trapped in this material (a/k/a the propagation material) and continue to bounce off each side of the material boundaries like a mirror as long as several conditions are met, primarily: a) the top and bottom boundaries remain flat and parallel to one another; b) the index of refraction of materials surrounding the propagation material remains lower than the index of refraction of the propagation material; or c) if one or both sides of the propagating material are surrounded by mirror-like reflection materials that will bounce any refracted light back into the propagation material. For example, see FIG. 28, which illustrates a schematic diagram 2800 of TIR conditions where $n_f < n_i$.

In regard to creating uniform light delivery across an LGF, methods to allow light rays that are trapped by TIR to reach a condition in which the ray's angle becomes less than the critical angle and can escape the LGF are disclosed herein. One simple method of creating this effect is to create surface features that present controlled or random angles to the light rays in the propagating material. In many cases a white reflective PET layer is used to create an efficient mirror like surface (reflectance up to 98%) on the bottom (non-light-emission-side) of the LGF and to have a top-most layer with a diffuser layer which has nanometer or micrometer sized features to disrupt the angular context of the light. For example, see FIG. 29, which illustrates a schematic diagram 2900 of disrupting TIR within an LGF.

These nanometer and micrometer structures can be applied to the LGF propagating materials in many different forms including diffusion materials or sheets laid on top of the propagating material. Alternatively, the nano- and microstructures can be embossed or cured onto the propagating material. Regarding the reflective material typically used on one side of the LGF, other highly reflective mirror like substrates can be substituted for the white reflective PET layer such as silver foil or a white painted surface.

Typically, the objective of using an LGF as a light delivery source is to create a uniform light distribution across the output interface. As mentioned, creating surfaces that bend the light inside the LGF to fall under the critical angle for TIR allows the light to exit. However, if the surface for disrupting the ray angles is too extreme, too much light can exit the LGF on the side closest to the light source (side-emitting LEDs) and result in little light exiting the opposite side of the LGF resulting in a non-uniform light distribution field across the LES.

Figure 29:
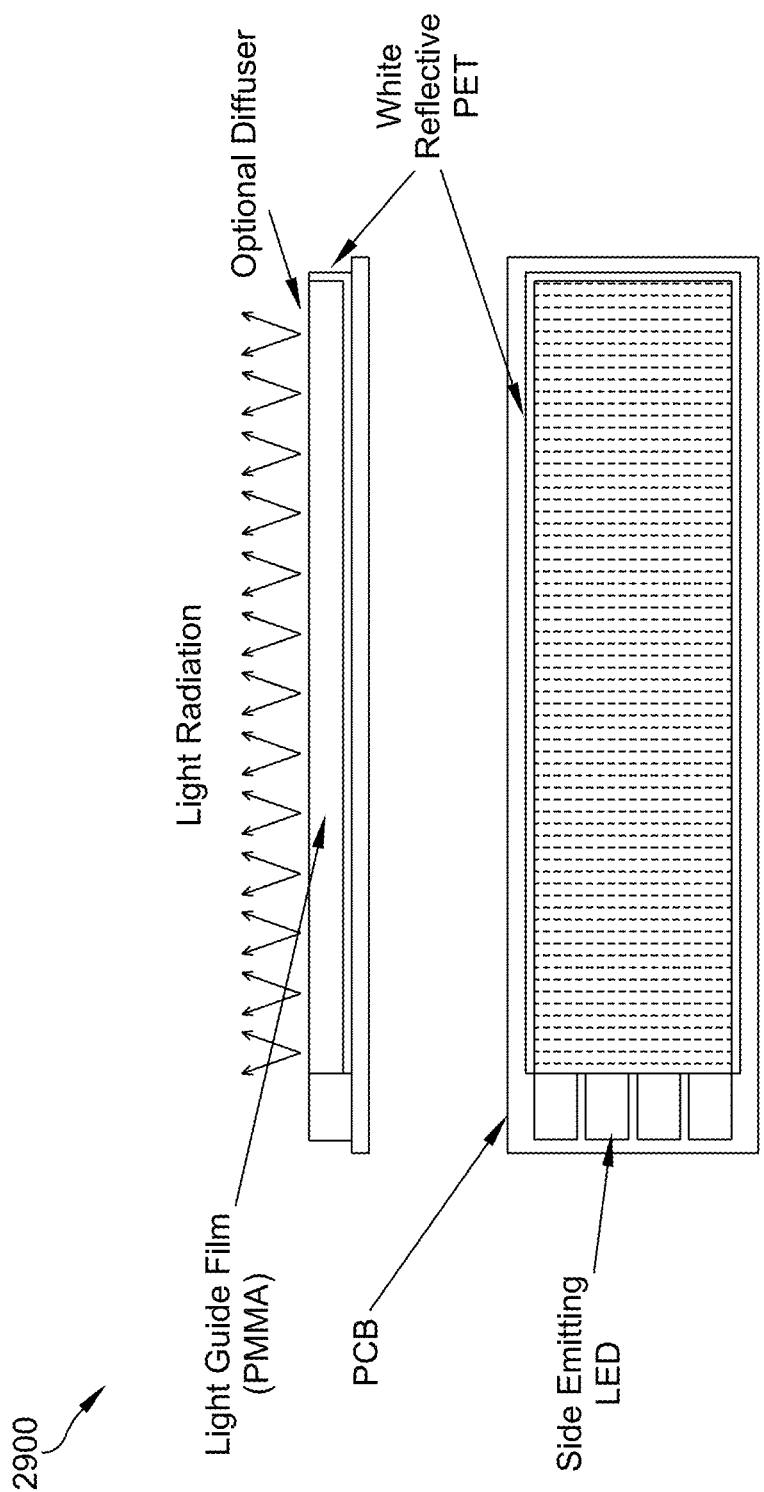
FIG. 29 depicts an example of a schematic diagram of disrupting TIR within an LGF.
Figure 30:
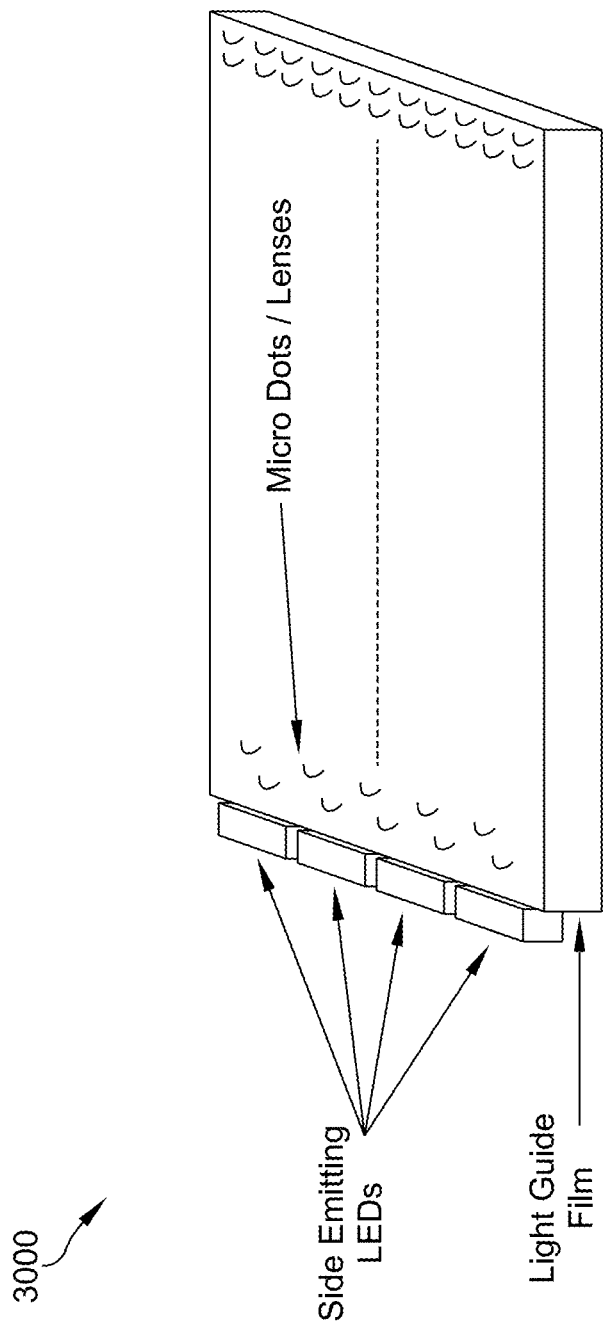
FIG. 30 depicts an example of a schematic diagram of microstructure size and location.
Figure 31:
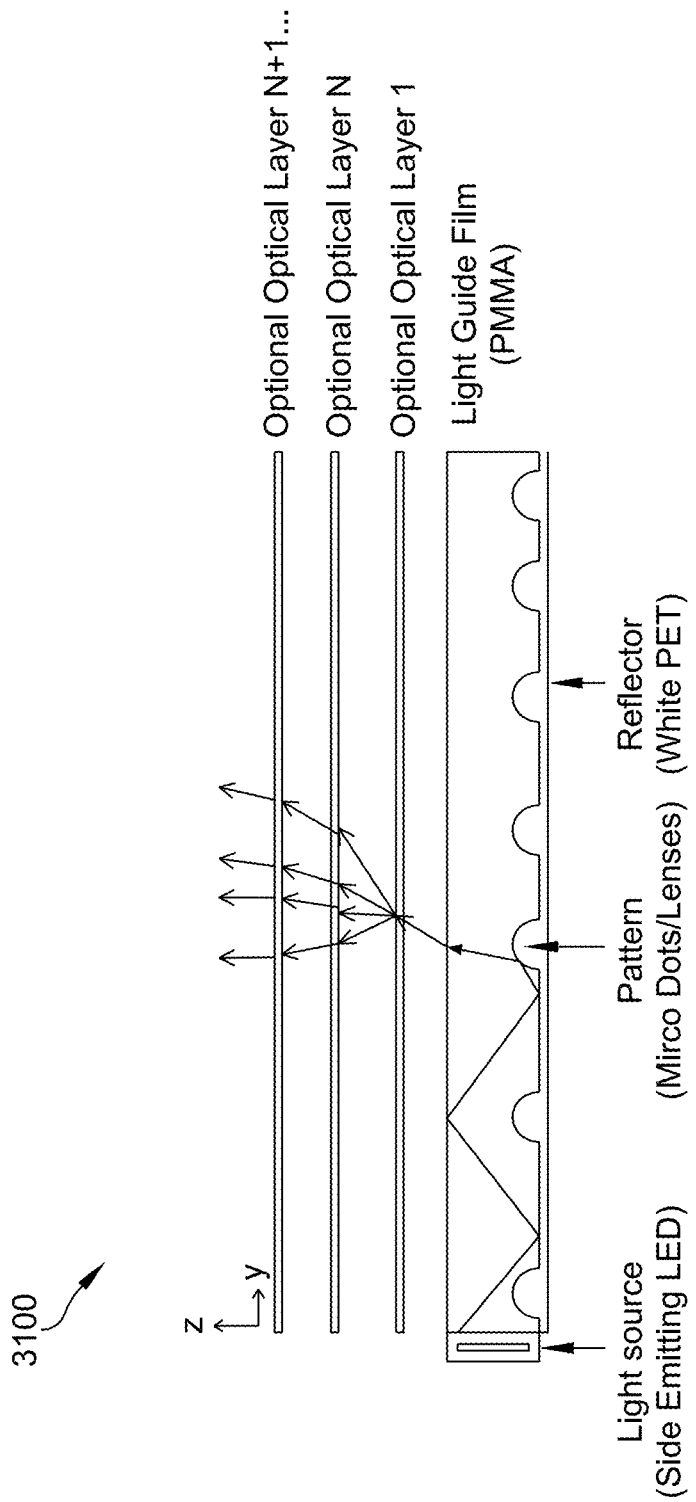
FIG. 31 depicts an example of a schematic diagram of microstructure size and location.

To generate a more uniform light distribution over a large surface area, when dealing with a one-dimensional LGF where light is only delivered along one input face (as seen in FIG. 29 and FIG. 30, discussed below), the nanostructures or microstructures, as one moves away from the light input surface, need to vary in size, going from larger and deeper structures closest to the light input and smaller and shallower structures furthest away from the light input. Additionally, the spacing or density between structures ideally becomes tighter the further away the structure is from the light input source. For example, FIGS. 30 and 31 show an example of the microstructure size and location as the structure moves further from the light source.

More specifically, FIG. 30 is a schematic diagram 3000 of microstructure size and location. With reference to FIG. 30, micro dots or micro lenses are considered structures that disrupt light ray angles inside the LGF that will allow rays to slowly break the critical angle and TIR conditions. By varying the structure in size and location across the LGF, light exitance can be more precisely controlled to create a uniform light output surface. FIG. 31 is a schematic diagram 3100 of microstructure size and location according to another embodiment. With reference to FIG. 31, the micro dot or micro lens structures can be imprinted on either the front or back side of the LGF. The structures can be convex, concave, or a combination of varying shapes.

Figure 32:
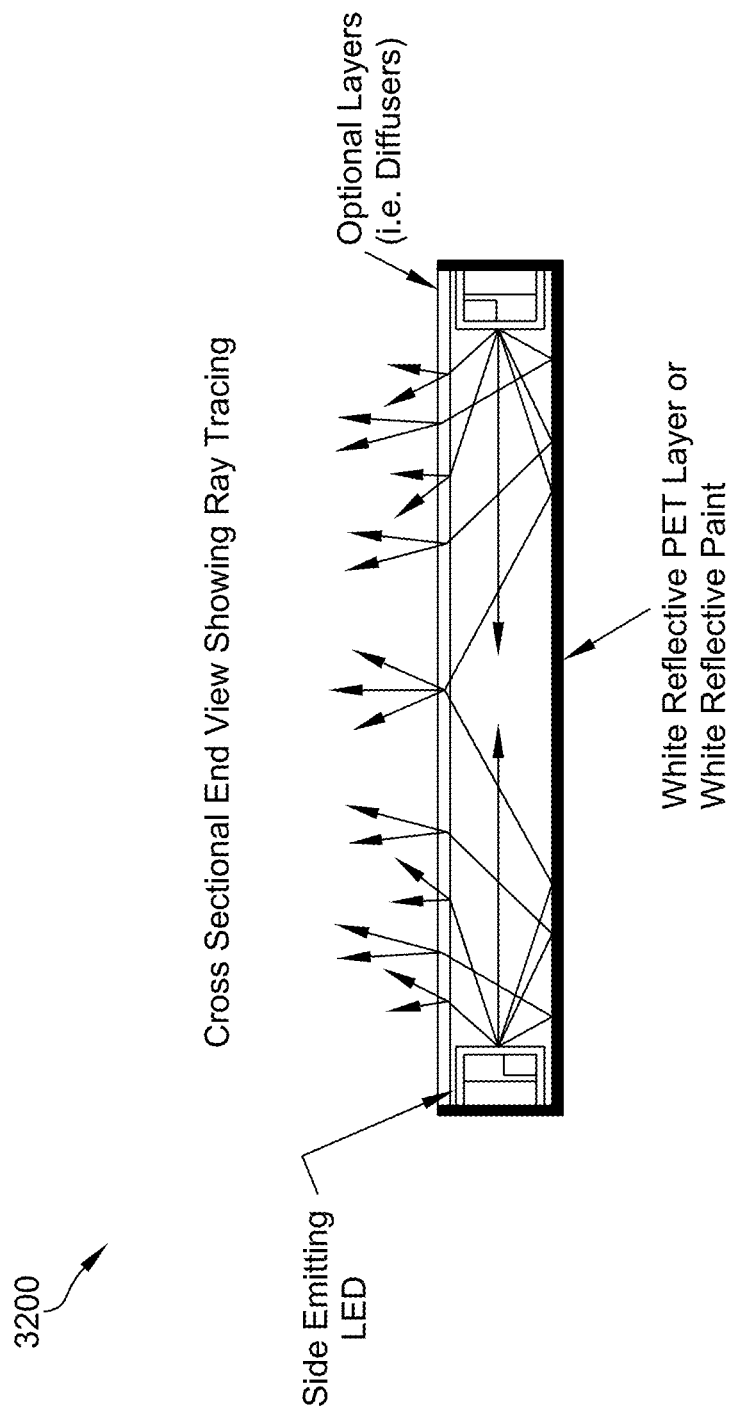
FIG. 32 depicts an example of a schematic view of multiple-sided light input sources.

An alternative to a one-dimensional or one-sided light source-based LGF is to have light enter the LGF from multiple input faces. An advantage of this approach is to address the limited efficiency from the side-emitting light sources when more light output is required from the light-emission surface and to account for optical light losses that may occur over the length of travel in the LGF. An example of a multisided illumination input interface LGF is shown in FIG. 32. FIG. 32 illustrates a schematic view 3200 of multiple-sided light input sources according to an embodiment.

Light input can come from multiple sides. In a multi-sided light input interface, such as the embodiment illustrated in FIG. 32, the nanometer and micrometer scale structure size and density will be two-dimensional, dependent upon the LGF shape. For example, the size of the structures will be larger and deeper closest to the illumination sources and in the center of the LGF, smaller and deeper. The density of the structures will increase as the structures move closest to the illumination source to the center of the LGF. If the LGF has light source input from more than 2 sides, the likely structural pattern is radial with structures becoming smaller and denser the further the structures are from the light input sources.

There are several techniques to create the nanometer and micrometer sized structures for the LGF. The simplest approach with very little precision is to roughen the surface. Sample production of this technique can be demonstrated on one surface of the propagating material with sandpaper. For more precision using this technique, another possible setup is to bring up small rough-surfaced dots on one side of the propagating material. The dots can be created with typical sanding/etching processes.

For more precision and to match with current optical design and modeling tools is to use modern manufacturing technologies with electron beam lithography, direct laser beam lithography, or diamond turning. Each of these techniques enables highly accurate tooling of nanostructures and microstructures. The preferred approach is using a nickel electroforming approach for tooling since it enables cost effective copy tools for mass production, while preserving nanoscale accuracy. Table 6 provides specifications for each of the processes that are generally available for LGF manufacturing.

TABLE 6

Precision Manufacturing Processes and Specifications for Nanostructures and Microstructures.

| Electron Beam Lithography | Direct Write Laser Lithography | Diamond Turning |
|---|---|---|
| sub-micron structures, feature sizes less than 100 nm binary/multilevel/continuous structure profiles typical patterned area up to 15 square centimeters typical structure depth < 1-2 um | structure size over a micrometer binary/continuous structure profile patterned area up to 45 cm squared typical structure depth < 15-20 um | micrometer scale structures circular/1-dimensional line patterns v-groove/triangle structure profiles small acute angle radius a high optical quality structure depths deeper than 1-3 um |

Figure 33:
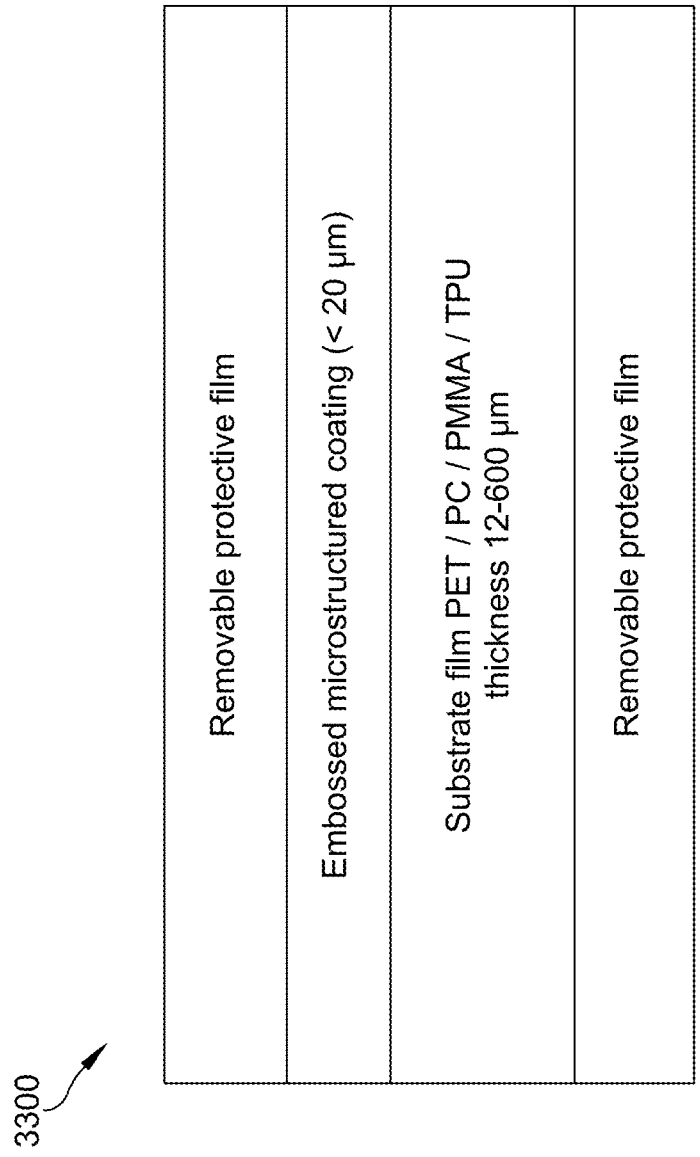
FIG. 33 depicts an example of a schematic view of an LGF, a combination of an embossed structure coating with a substrate film.

In low-volume production a master tool—a reverse imprint of the nanostructures and microstructures or, depending on the replication technique, the positive version of the structures—will be made and then embossed using standard techniques and tools into embossing material, such as UV-curable lacquer, that resides on a base substrate material, like transparent PET/PC/PMMA/TPU. Together the embossed structure coating and the substrate film make up the LGF, as illustrated in FIG. 33. FIG. 33 illustrates a schematic view 3300 of an LGF, a combination of an embossed structure coating with a substrate film. The removable protective film of FIG. 33 is applied to protect the structures prior to deployment/use.

In large-scale production, roll-to-roll production is a preferred mass manufacturing technology for nanostructures and microstructures, offering cost efficiency and nanometer accuracy. Again, as in the low-volume production process, the nanostructures and microstructures are printed on a UV-curable lacquer on a substrate film. Typically, all LGF production is performed in a cleanroom with machine vision and individual component markings to ensure controlled manufacturing. Cutting of parts is typically performed with precision die-cutting or laser-cutting.

Enumerated Embodiments

Method of Treating a Subject

1. A method of treating a subject, the method comprising:
    irradiating the subject with light having a wavelength between 380 nm and 500 nm, for example, at 405 nm, at 25 to 25 milliWatts/cm$^2$,
    wherein the irradiation is for a time sufficient to treat a subject, and wherein treating comprises:
        a) treating a subject at risk for a pathogen infection;
        b) treating a subject having a pathogen infection;
        c) preventing the infection by a pathogen;
        d) reducing the level of a pathogen;
        e) reducing the virulence of a pathogen in the subject, for example, reducing its ability to damage the subject, slowing the growth of the pathogen, or reducing the release of a toxin by the pathogen;
        f) reducing or otherwise ameliorating an unwanted manifestation of infection by a pathogen;
        g) reducing the level or transmission of a transmissible nucleic acid, for example, a plasmid or an RNA, by a pathogen, for example, to a second pathogen; or
        h) modulating, for example, inhibiting, reducing, or degrading the structure or integrity an extracellular matrix;

i) modulating the microbiome of the subject, for example, at the site of irradiation or at site outside the site of irradiation, for example, reducing one or more members of a polymicrobial community; or j) irradiating a site at which a device, for example, a catheter or conductor, enters the subject's body.

2. The method of numbered embodiment 1, further comprising treating a subject at risk for a pathogen infection.

3. The method of any of numbered embodiments above, further comprising treating a subject having a pathogen infection.

4. The method of numbered embodiment above, further comprising preventing the infection by a pathogen, of a subject.

5. The method of numbered embodiment above, further comprising reducing the level of a pathogen in a subject.

6. The method of any of numbered embodiments above, further comprising reducing the virulence of a pathogen in the subject, for example, reducing its ability to damage the subject, slowing the growth of the pathogen, or reducing the release of a toxin by the pathogen.

6b. The method of any of numbered embodiments above, further comprising reducing or otherwise ameliorating an unwanted manifestation of infection by a pathogen.

7. The method of any of numbered embodiments above, further comprising reducing the level or transmission of a transmissible nucleic acid, for example, a plasmid or an RNA, by a pathogen, for example, to a second pathogen.

7a. The method of any of numbered embodiments above, wherein the transmissible nucleic acid comprises a sequence that confers resistance to an antibiotic.

7b. The method of numbered embodiment any of above, further comprising modulating, for example, inhibiting, reducing, or degrading an extracellular matrix, for example, a biofilm, for example, in the area irradiated.

7c. The method of any of numbered embodiments above, further comprising increasing the porosity of a biofilm, for example, increasing the porosity to a drug, for example, an antibiotic.

7d. The method of any of numbered embodiments above, further comprising modulating, for example, inhibiting, reducing, or degrading the structure or integrity a biofilm, for example, forming fenestrations in the biofilm.

7e. The method of any of numbered embodiments above, further comprising modulating the microbiome of the subject, for example, at the site of irradiation or at site outside the site of irradiation for example, decreasing the proportion or numbers of a first microbe, for example, a pathogen, for example, MRSA, VRE, and optionally, increasing the proportion of numbers of a second microbe, for example, a non-pathogen, for example, Lactobacillus.

7f. The method of any of numbered embodiments above, further comprising irradiating a site at which a device, for example, a catheter or conductor, enters the subject's body.

8. The method of any of numbered embodiments above, wherein the subject has a wound.

8a. The method of any of numbered embodiments above, wherein the subject has an acute wound such as a trauma, surgical, or burn wound.

8b. The method of any of numbered embodiments above, wherein the subject has a chronic wound such as from decubitus, pressure, diabetic, venous stasis ulcers.

8c. The method of any of numbered embodiments above, wherein the subject has compromised renal function, for example, renal function that has been impaired by a disorder or a medical treatment, for example, antibiotic treatment.

8d. The method of any of numbered embodiments above, wherein the subject has compromised hepatic function, for example, hepatic function that has been impaired by a disorder or a medical treatment, for example, antibiotic treatment.

9. The method of any of numbered embodiments above, wherein the subject has a burn, for example, a burn that is greater than a Grade 1 burn, for example, a superficial first-degree burn of the epidermis, or outer layer of skin.

9a. The method of any of numbered embodiments 1-9, wherein the subject has a burn, for example, a burn that is greater than a Grade 1 Burn, covering at least 1%, 10%, 50%, or 100% of Total Body Surface Area (TBSA).

9b. The method of any of numbered embodiments 1-9, wherein the subject has a burn, for example, a burn that is greater than a Grade 1 burn, covering 1% to 100%; 5% to 80%; or 10% to 50%, of TBSA.

10. The method of any of numbered embodiments 1-9b, wherein the subject is less than 1, 2, 5, 10, 18, 30, 50, 60 75 or 100 years of age.

11. The method of any of numbered embodiments 1-9b, wherein the subject is between 30 days and 100 years, or 1 and 5, 3 and 18, 18 and 50, 50 and 60 or 60 and 80 years of age.

12. The method of any of numbered embodiments 1-9b, wherein the subject more than 30 days of age.

13. The method of any of numbered embodiments above, wherein the subject is immune-compromised, for example, the subject has a hereditary or acquired or induced immune deficiency, or compromised organ function, for example, compromised hepatic or renal function.

13a. The method of any of numbered embodiments above, wherein the site irradiated comprises skin.

13b. The method of any of numbered embodiments above, wherein the site irradiated is disposed in whole or part on the arm, leg, torso, genitals, back, neck, head, face, hand, or foot.

13c The method of any of numbered embodiments above, wherein the site irradiated is disposed in whole or part in a natural orifice, for example, in the nose, sinus, urethra, ear canal, male or female genital tract, nasal passage, mouth, throat, upper GI tract and rectum.

13d. The method of any of numbered embodiments above, wherein the site irradiated comprises entry point of a medical device, for example, the point of entry of a conduit, catheter, PIC line, Hickman catheter.

13e. The method of any of numbered embodiments above, wherein the site irradiated comprises entry point of a conductor, for example, from a power source, for example, the power source for an LVT assist device.

13f. The method of any of numbered embodiments above, wherein the site irradiated comprises entry point of a conductor or conduit to an implanted medical device, for example, a stent, for example, a biliary stent.

14. The method of any of numbered embodiments 1-13e, wherein the light has a wavelength between 380 nm and 500 nm.

14a. The method of any of numbered embodiments 1-13e, wherein the light has a wavelength between 390 nm and 430 nm.

14b. The method of any of numbered embodiments 1-13e, wherein the light has a wavelength between 395 nm and 415 nm.

14c. The method of any of numbered embodiments 1-13e, wherein the light has a wavelength between: 380 nm and 415 nm.

15. The method of any of numbered embodiments 1-13e, wherein the light has a wavelength 405 nm+/−10 nm.

16. The method of any of numbered embodiments 1-13e, wherein the light has a wavelength 405 nm+/−20 nm.

17. The method of any of numbered embodiments 1-13e, wherein the light has a wavelength 405 nm.

18. The method of any of numbered embodiments above, wherein the light is provided at between 0.25 and 25 milliWatts/cm$^2$.

18b. The method of any of numbered embodiments 1-17, wherein the light is provided at between 1 and 15 milliWatts/cm$^2$.

18c. The method of any of numbered embodiments above, wherein the light is provided at between 5 and 10 milliWatts/cm$^2$.

19. The method of any of numbered embodiments 1-17, wherein the light is provided at 470+/−10.

19. The method of any of numbered embodiments 1-17, wherein the light is provided at 470+/−20.

20. The method of any of numbered embodiments 1-17, wherein the light is provided at 5-10 mW/cm$^2$.

20a. The method of any of numbered embodiments 1-17, wherein the light is provided at 5.5-8.33 mW/cm$^2$.

20b. The method of any of numbered embodiments 1-20a, wherein the subject has an acute infection, for example, an acute MRSA, MSSA, or *S. epidermis* infection and the light is provided at 5.5-8.33 mW/cm$^2$.

20c. The method of any of numbered embodiments 1-20a, wherein the subject has a chronic infection, for example, a chronic infection or a chronic antibiotic infection, a VRE, KPC, or NDM1, and the light is provided at 5-10 mW/cm$^2$, for example, 8.33 mW/cm$^2$.

21. The method of any of numbered embodiments above, wherein the light is provided for a time sufficient to prevent the infection of a subject by a pathogen.

22. The method of any of numbered embodiments above, wherein the light is provided for a time sufficient reduce the level of a pathogen in a subject.

23. The method of any of numbered embodiments above, wherein the light is provided for a time sufficient reduce the level of viable pathogen at the site of irradiation by 1.5, 2, 3, 4, 5, 6, 7, 8, 9, 10, 20, 50, or 100 fold.

24. The method of any of numbered embodiments 1-23, wherein the light is provided for at least 6, 24, 72, or 168 hours.

25. The method of any of numbered embodiments 1-23, wherein the light is provided for 6 to 168; 12 to 120; or 24 to 72 hours.

26. The method of any of numbered embodiments above, wherein the light is provided at a total fluence sufficient 240 J/cm2 a pathogen in a subject.

27. The method of any of numbered embodiments 1-25, wherein the light is provided at a total fluence of at least 60, 240, 6,480, or 15,120 J/cm$^2$.

28. The method of any of numbered embodiments 1-25, wherein the light is provided at a total fluence of 60 to 15,120; 120 to 10,800; or 240 to 6,480 J/cm$^2$.

29. The method of any of numbered embodiments 1-25, wherein the light is provided at a total fluence of 60; 240; 6,480; or 15,210 J/cm$^2$.

30. The method of any of numbered embodiments above, wherein the light provided is sufficient to kill the pathogen but does not result in damage to normal surrounding healthy tissue, such as fibroblasts, keratinocytes, nerves and blood vessels.

31. The method of any of numbered embodiments above, wherein the level of pathogen is reduced sufficiently such that there is at least 99.0% or 99.9% reduction in colony forming units/milliliter (cfu/ml), for example, at the site of irradiation.

31a. The method of any of numbered embodiments above, wherein the level of pathogen is reduced sufficiently to confer antibiotic sensitivity.

32. The method of any of numbered embodiments above, wherein the level of the pathogen in the irradiated tissue is reduced.

33. The method of any of numbered embodiments above, wherein the systemic or circulatory level of the pathogen is reduced.

34. The method of any of numbered embodiments 1-33, wherein 0.1 to 2000.0; 0.25 to 1000.0; 0.5 to 100.0; and 1.0 to 50.0, cm$^2$ of the surface of the subject is irradiated.

35. The method of any of numbered embodiments 1-33, wherein the surface irradiated comprises: 0.1, 1.0, 100.0, or 2000.0 cm$^2$ of any cutaneous and mucutaneous surface.

36. The method of any of numbered embodiments above, wherein the surface irradiated comprises: a wound, a burn, an ulcer, rash, surgical incision, cut, catheter, bone, cast, orthopedic implant, or bandage dressing.

37. The method of any of numbered embodiments above, wherein the surface irradiated comprises a diabetic ulcer, a pressure ulcer, a decubitus ulcer, or a venous stasis ulcer.

38. The method of any of numbered embodiments above, wherein the irradiation is administered in a health care facility, for example, a hospital, clinic, or physician's office.

39. The method of any of numbered embodiments 1-37, wherein the irradiation is administered at a place other than a health care facility, for example, a hospital, clinic, or physician's office, for example, the irradiation is administered after discharge or exit from a health care facility, for example, a hospital, clinic, or physician's office.

40. The method of any of numbered embodiments above, wherein the irradiation is initiated in a health care facility, for example, a hospital, clinic, or physician's office.

41. The method of any of numbered embodiments above, wherein the irradiation is initiated at a place other than a health care facility, for example, a hospital, clinic, or physician's office, for example, the irradiation is administered after discharge or exit from a health care facility, for example, a hospital, clinic, or physician's office.

42. The method of any of numbered embodiments 1-40, wherein the irradiation is initiated in a health care facility, for example, a hospital, clinic, or physician's office and is continued at a place other than a health care facility, for example, a hospital, clinic, or physician's office.

43. The method of any of numbered embodiments above, wherein the irradiation is provided as a single treatment, for example, without a period where the irradiation ceases.

44. The method of any of numbered embodiments 1-42 wherein the irradiation is provided as a plurality of treatments, for example, the irradiation is initiated and continues for a time, is halted, and is initiated a second time.

45. The method of any of numbered embodiments 1-42, wherein the irradiation is initiated in a health care facility, for example, a hospital, clinic, or physician's office and is continued for at least 6 hours, 1 day, 7 days, or 30 days in the health care facility.

46. The method of any of numbered embodiments 1-42, wherein the irradiation is continued or reinitiated at a place other than the health care facility, and, for example, is continued for at least 6 hours, 1 day, 7 days, or 30 days at the place other than the healthcare facility.

46a. The method of any of numbered embodiments above, wherein the irradiation is provided by a wearable device.

46b. The method of any of numbered embodiments above, wherein the irradiation is provided by a device weighing less than 15, 10, 5, or 2 kilograms.

46c. The method of any of numbered embodiments above, wherein the irradiation is provided by a device comprising a power source, for example, a wearable power source.

46d. The method of any of numbered embodiments above, wherein the irradiation is provided by a device comprising a battery.

46e. The method of any of numbered embodiments above, wherein the irradiation is provided by a device described herein, for example, in any of numbered embodiments above.

46f. The method of any of numbered embodiments above, wherein the light is delivered at a radiance that does not deplete $O_2$ in the pathogen.

46g. The method of any of numbered embodiments above, wherein the light is delivered at a radiance that does not bleach a chromophore, for example, an endogenous chromophore, in the pathogen.

46gi. The method of any of numbered embodiments above, wherein a light related parameter, for example, wavelength, intensity, duration, or cycle can be varied (the alternation of periods of irradiation with an intervening period in which irradiation is not provided, can be varied over area and or time).

46gii. The method of any of numbered embodiments above, wherein light related parameter can be provided at a first value at a first location, for example, a location with relatively more healing, and a second value at a second location, for example, a location with relatively less healing.

46giii. The method of any of numbered embodiments above, wherein the light is delivered at a first intensity for a first period of time and at a second intensity for second period of time.

46h. The method of any of numbered embodiments above, wherein the light is delivered at a first intensity to a first site on the subject and at a second intensity at a second site on the subject.

46i. The method of any of numbered embodiments above, wherein the light is delivered at a first wavelength for a first period of time and at a second wavelength for second period of time.

46j. The method of numbered embodiment above, wherein the light at the first wavelength is optimized for killing a pathogen, for example, blue light, for example, light having a wavelength of between 390 nm and 420 nm, and the light at the second wavelength is optimized for promoting wound healing, for example, red or infrared light, for example, light having a wavelength between 600 nm and 700 nm, for example, light having a wavelength between 700 nm and 1000 nm.

46k. The method of numbered embodiment above, wherein the first period of time occurs before the second period of time.

46l. The method of any of numbered embodiments above, wherein the light is delivered at a first wavelength to a first site on the subject and is delivered at a second wavelength to a second site on the subject.

46m. The method of numbered embodiment above, wherein the first site comprises a first injury or lesion and the second site comprises a second injury or lesion.

46n. The method of numbered embodiment above, wherein the first site comprises a burn and the second site comprises a burn.

46o. The method of numbered embodiment above, wherein the burn at the first site comprises burn having a different severity than the burn at the second site.

46p. The method of numbered embodiment above, wherein the first site comprises a third or fourth degree burn.

46q. The method of numbered embodiment above, wherein the second site comprises a first or second degree burn.

46r. The method of any of numbered embodiments above, wherein the first site is irradiated with light of wavelength of less than 400 nm, for example, between, 280 and 315 nm (UV-B) or 315 nm and 400 nm (UV-A).

46s. The method of any of numbered embodiments above, wherein the second site is irradiated with light of wavelength between, 390 nm and 420 nm, for example, 405 nm.

46t. The method of any of numbered embodiments above, wherein the method includes a period or pulse of irradiation, an intervening period when irradiation is not provided, and a subsequent period or pulse of irradiation.

46u. The method of numbered embodiment above, wherein the intervening period is sufficient in duration to allow an increase in $O_2$ in the pathogen, as compared to what is present at the beginning of the intervening period.

46i. The method of any of numbered embodiments above, wherein irradiation is provided as a plurality of periods or pulses wherein the pulses are separated by intervening periods when irradiation is not provided, for example, darkness.

46ii. The method of any of numbered embodiments above, further comprising providing a plurality of periods or pulses of irradiation of at least 0.1, 3,600, or 86,400 seconds each, separated by a intervening periods of at least 0.1, 3,600, or 86,400 seconds each when irradiation is not provided.

46iii. The method of any of numbered embodiments above, wherein each pulse of the plurality is of equal duration.

46iv. The method of any of numbered embodiments above, wherein a first pulse and a second pulse of the plurality are of different duration.

46v. The method of any of numbered embodiments above, wherein each intervening period is of equal duration.

46vi. The method of any of numbered embodiments above, wherein a first intervening period and a second intervening period are of different duration.

46vii. The method of any of numbered embodiments above, wherein the device is configured such that ambient light does not reach the surface covered by the area, for example, such that the surface is in darkness when the irradiation is not provided.

46viii. The method of any of numbered embodiments 1-46vii, wherein at least 1, 100,000, 1,000,000, or 1,000,000,000 pulses of irradiation are provided.

46ix. The method of any of numbered embodiments 1-46vii, wherein irradiation is provided at 3600, 30, 15, 5 or 1 cycle(s) per hour, wherein a cycle is a period or pulse of irradiation and intervening period.

46x. The method of any of numbered embodiments 1-46vii, wherein irradiation is provided at 3600 to 1; 30 to 5; or 20 to 10 cycle(s) per hour, wherein a cycle is a period or pulse of irradiation and intervening period.

46xi. The method of any of numbered embodiments 1-46vii, wherein a period of irradiation (for example, over a 24-hour period) delivers 0.00025 (0.25 mW*1 sec), 1, 10, 100, 1000, or 2,160 (25 mW*86,400 sec) J/cm$^2$.

46xii. The method of any of numbered embodiments above, wherein a period of irradiation (for example, over a 24-hour period) delivers 0.00025 to 2,160; 1 to 1,000; or 100 to 500 J/cm$^2$ 46xiii. The method of any of numbered embodiments above, wherein a period of irradiation delivers sufficient light that bacteria cell death occurs, for example, 99.0% or 99.9% Log reduction in CFU/ml.

46xiv. The method of any of numbered embodiments above, wherein a period of irradiation is sufficiently limited that it does not result in damage to surrounding normal healthy tissue.

46xv. The method of any of numbered embodiments above, wherein intervening period is of sufficient duration that:
i) there is regeneration of chromophores that absorb at the irradiated frequency;
ii) O$_2$ in the wound increases, for example, increases sufficiently that the photodynamic reaction can occur; or
iii) diffusion of O$_2$ from surrounding tissues occurs.

46xvi. The method of any of numbered embodiments above, wherein the irradiation is pulsed and the symmetry remains constant throughout the treatment.

46xvii. The method of any of numbered embodiments above, wherein the irradiation is pulsed and the symmetry value changes over time.

46xvii. The method of any of numbered embodiments above, wherein the irradiation is pulsed and the symmetry value increases over time.

46xix. The method of any of numbered embodiments above, wherein the irradiation is pulsed and the symmetry value decreases over time.

46xx. The method of any of numbered embodiments above, wherein the irradiation is pulsed and the symmetry value changes or is changed over time in response to the condition of the subject.

46xxi. The method of any of numbered embodiments above, wherein the irradiation is pulsed and the wave form of the irradiation period is step or square wave, a saw-tooth wave form, a triangle wave form, a discrete piece wise wave form, or a sinusoidal wave form.

46v. The method of numbered embodiment above, wherein the intervening period is sufficient to allow an increase in a chromophore in the pathogen, as compared to what is present at the beginning of the intervening period.

46w. The method of numbered embodiment 46v, wherein the intervening period is 0.00167 to 60, 1 to 20, for example, 1, 2, 3, 4, or 5, minutes in duration.

46wi. The method of numbered embodiment 46v, wherein the intervening period is at least 1, 2, 3 4, 5, 6, 7, 8, 9 or 10 hours in duration.

46x. The method of any of numbered embodiments above, wherein irradiation is cycled between periods of irradiation and intervening periods for at least 0.0000277, 1, 10, 24, 48, 72, or 96 hours.

47. The method of any of numbered embodiments above, wherein the pathogen comprises a bacterium, fungus, protozoan, spore, virus, helminthes (for example, a. Nematode, flatworm, roundworm), or an extoparasite.

48. The method of any of numbered embodiments above, wherein the pathogen comprises a bacterium from Table 3, a fungus, or a protozoan from Table 2.

49. The method of any of numbered embodiments above, wherein the pathogen comprises a drug resistant pathogen.

50. The method of any of numbered embodiments above, wherein the pathogen comprises a bacterium and is resistant to a drug from Table 3 or 4.

51a. The method of any of numbered embodiments above, wherein the pathogen comprises *Acinetobacter baumannii*, for example, carbapenem-resistant *Acinetobacter baumannii*.

51b. The method of any of numbered embodiments above, wherein the pathogen comprises *Pseudomonas aeruginosa*, for example, carbapenem-resistant *Pseudomonas aeruginosa*.

51c. The method of any of numbered embodiments above, wherein the pathogen comprises Enterobacteriaceae, for example, carbapenem-resistant or ESBL-producing Enterobacteriaceae.

51d. The method of any of numbered embodiments above, wherein the pathogen comprises *Enterococcus faecium*, for example, vancomycin-resistant *Enterococcus faecium*.

51e. The method of any of numbered embodiments above, wherein the pathogen comprises *Staphylococcus aureus*, for example, methicillin-resistant, vancomycin-intermediate and resistant *Staphylococcus aureus*.

51f. The method of any of numbered embodiments above, wherein the pathogen comprises *Helicobacter pylori*, for example, clarithromycin-resistant *Helicobacter pylori*.

51g. The method of any of numbered embodiments above, wherein the pathogen comprises *Campylobacter* spp, for example, fluoroquinolone-resistant *Campylobacter* spp.

51h. The method of any of numbered embodiments above, wherein the pathogen comprises Salmonellae, for example, fluoroquinolone-resistant Salmonellae.

51i. The method of any of numbered embodiments above, wherein the pathogen comprises *Neisseria gonorrhoeae*, for example, cephalosporin-resistant or fluoroquinolone-resistant *Neisseria gonorrhoeae*.

51j. The method of any of numbered embodiments above, wherein the pathogen comprises *Streptococcus pneumoniae*, for example, penicillin-non-susceptible *Streptococcus pneumoniae*.

51k. The method of any of numbered embodiments above, wherein the pathogen comprises *Haemophilus influenzae*, for example, ampicillin-resistant *Haemophilus influenzae*.

51l. The method of any of numbered embodiments above, wherein the pathogen comprises *Shigella* spp., for example, fluoroquinolone-resistant *Shigella* spp.

51m. The method of any of numbered embodiments above, wherein the pathogen comprises a parasitic infection, and the parasite obtains heme from the subject.

51n. The method of any of numbered embodiments above, wherein the pathogen comprises *Trypanosoma cruzi*.

51o. The method of any of numbered embodiments above, wherein the pathogen comprises *taenia solium*.

51p. The method of any of numbered embodiments above, wherein the pathogen comprises toxocara.

52. The method of any of numbered embodiments above, wherein the pathogen comprises *Staphylococcus aureus* (MRSA methicillin RSA and MSSA methycilllin) and Staph. epidermidis (coagulase-negative Staph) and is resistant to methicillin, vancomycin, or doxycycline.

53. The method of any of numbered embodiments above, wherein the pathogen is a pathogen from Table 3 and is resistant to a drug from Table 3 or 4.

55. The method of any of numbered embodiments above, wherein the subject comprises a second, third, fourth, fifth, sixth or seventh pathogen.

56. The method of any of numbered embodiments above, wherein the subject has a burn and the burn is infected with, or at risk for infection with, the pathogen.

57. The method of any of numbered embodiments above, wherein the subject has an injury to the skin or mucosa resulting in a partial- or full-thickness wound.

59. The method of any of numbered embodiments above, wherein the subject has not been treated with an exogenous compound, for example, a dye or photosensitizer, for example, one selected from Table 1, for example, photofrin or ALA.

59. The method of any of numbered embodiments 1-57, wherein the subject has been treated with an exogenous compound, for example, a dye or photosensitizer, for example, one selected from Table 1, for example, photofrin or ALA.

60. The method of any of numbered embodiments above, wherein, at a time during irradiation, for example, at initiation, or for the entire course of irradiation, the irradiated tissue does not comprise an exogenous compound which absorbs light at 380 nm to 500 nm, for example, an exogenous compound, for example, a dye or photosensitizer, for example, photofrin or ALA.

61. The method of any of numbered embodiments above, wherein a second therapeutic agent is provided, for example, administered, to the subject.

62. The method of numbered embodiment above, wherein the second therapeutic agent comprises an antibiotic, for example, Ampicillin, Methicillin, or Vancomycin.

63. The method of numbered embodiment above, wherein the antibiotic comprises an antibiotic from Table 3 or 4.

64. The method of any of numbered embodiments above, wherein the second therapeutic agent is provided systemically, for example, by intra vascular, for example, intravenous administration.

65. The method of any of numbered embodiments above, wherein treatment with the second therapeutic agent is initiated prior to initiation of irradiation, at the same time as initiation of irradiation, after initiation of irradiation, during the course of irradiation, or after the course of irradiation.

66. The method of any of numbered embodiments 1-65, wherein irradiation is initiated prior to initiation of the provision of the second therapeutic agent, at the same time as initiation of provision of the second therapeutic agent, after initiation of provision of the second therapeutic agent, during the course of provision of the second therapeutic agent, or after the provision of the second therapeutic agent.

67. The method of any of numbered embodiments above, wherein the second therapeutic agent comprises an agent from Table 3, 4 or 0.5.

67a. The method of any of numbered embodiments above, comprising the application of negative pressure to the wound bed.

67b. The method of numbered embodiment 67a, wherein the negative pressure is constant throughout the use of the device or throughout a portion of the time the device is contacted with the subject.

67c. The method of any of numbered embodiments 67a-67b, wherein different pressures, for example, at different times of the day, at different stages of treatment or healing, or with different wavelengths of light being applied.

67d. The method of any of numbered embodiments 67a-67c, wherein a first level of negative pressure is applied at a first point of a preselected period, for example, a 24 hour period, and a second level of negative pressure is applied at a second point of the preselected period.

67e. The method of any of numbered embodiments 67a-67c, wherein a first level of negative pressure is applied at a first stage of healing or treatment, and a second level of negative pressure is applied at a second stage of healing or treatment.

67f. The method of any of numbered embodiments 67a-67c, wherein a first level of negative pressure is applied during irradiation at a first wavelength, and a second level of negative pressure is applied during irradiation with a second wavelength.

Method of Treating a Subject having a Burn

68. A method of treating a subject having a burn, the method comprising: irradiating the subject with light having a wavelength between 380 nm and 500 nm at 0.25 to 25 milliWatts/cm$^2$, wherein the irradiation is for a time sufficient to prevent infection of the subject by a pathogen reducing the level of a pathogen (for example, in the burn or systemically), or reducing or otherwise ameliorating an unwanted manifestation of infection by a pathogen (for example, in the burn or systemically) in a subject.

69. The method of numbered embodiment 68, wherein the subject at risk for a pathogen infection (for example, in the burn or systemically).

70. The method of numbered embodiment above, further comprising preventing the infection of the subject (for example, in the burn or systemically), by the pathogen.

71. The method of numbered embodiment above, further comprising reducing the level of pathogen (for example, in the burn or systemically).

72. The method of numbered embodiment above, further comprising reducing or otherwise ameliorating an unwanted manifestation of infection by a pathogen (for example, in the burn or systemically).

73. The method of numbered embodiment above, further comprising reducing toxins released by or created by a pathogen or making the pathogen more sensitive to an antimicrobial agent.

74. The method of any of numbered embodiments above, wherein the subject is less than 1, 2, 5, 10, 18, 30, 50, 60 75 or 100 years of age.

75. The method of any of numbered embodiments above, wherein the subject is between 30 days and 100 years, or 1 and 5, 3 and 18, 18 and 50, 50 and 60, or 60 and 80 years of age.

76. The method of any of numbered embodiments above, wherein the subject more than 30 days of age.

77. The method of any of numbered embodiments above, wherein the subject has a burn wound beyond 1$^{st}$ degree burn and greater than 10% total body surface area (TBSA).

78. The method of any of numbered embodiments above, wherein the burn comprises a first-, second- or third-degree burn.

79. The method of any of numbered embodiments above, wherein the burn covers more than 1%, 5%, 10%, 25% or 50% of the subject's body.

80. The method of any of numbered embodiments above, wherein the burn covers from: 1% to 100%; from 2% to 90%; 5% to 80%; or 10% to 50% of the subject's body.

81. The method of any of numbered embodiments above, wherein the burn comprises the subject's arm, leg, torso, face, back, genitals, or extremities (fingers, toes).

82. The method of any of numbered embodiments above, wherein the burn is a thermal burn.

83. The method of any of numbered embodiments above, wherein the burn is a fire/flame burn, a scald, a burn from contact with a hot object, an electrical burn, or chemical burn.

84. The method of any of numbered embodiments above, wherein irradiation is initiated within 0, 24, 72, or 168 hours of infliction of the burn.

85. The method of any of numbered embodiments above, wherein irradiation is initiated more than 0, 4, 72, or 168 hours after infliction of the burn.

87. The method of any of numbered embodiments above, wherein the light has a wavelength between: 380 nm and 500 nm; 390 nm and 430 nm; and 395 nm and 415 nm.

88. The method of any of numbered embodiments above, wherein the light has a wavelength 405+/−10.

88. The method of any of numbered embodiments above, wherein the light has a wavelength 405+/−20.

89. The method of any of numbered embodiments above, wherein the light has a wavelength 405 nm.

90. The method of any of numbered embodiments above, wherein the light is provided at between 0.25 and 25 milliWatts/cm$^2$.

91. The method of any of numbered embodiments above, wherein the light is provided at 6+/−3 milliWatts/cm$^2$.

92. The method of any of numbered embodiments above, wherein the light is provided at 5.5 mW/cm$^2$.

93. The method of any of numbered embodiments above, wherein the light is provided for a time sufficient to prevent the infection of a subject by a pathogen.

94. The method of any of numbered embodiments above, wherein the light is provided for a time sufficient reduce the level of a pathogen in a subject.

95. The method of any of numbered embodiments above, wherein the light is provided for a time sufficient kill or neutralize a pathogen in a subject.

96. The method of any of numbered embodiments above, wherein the light is provided for at least 6, 24, 72, or 168 hours.

97. The method of any of numbered embodiments above, wherein the light is provided for 6 to 168; 12 to 120; or 24 to 72 hours.

98. The method of any of numbered embodiments 68-97, wherein the light is provided at a total fluence sufficient 90 J/cm$^2$ a pathogen in a subject.

99. The method of any of numbered embodiments 68-97, wherein the light is provided at a total fluence of at least 60, 240, 6,480, or 15,120 J/cm$^2$.

100. The method of any of numbered embodiments 68-97, wherein the light is provided at a total fluence of 60 to 15,120; 120 to 880; or 240 to 6,480 J/cm$^2$.

101. The method of any of numbered embodiments 68-97, wherein the light is provided at a total fluence of 60, 240, 6,480, or 15,210 J/cm$^2$.

102. The method of any of numbered embodiments above, wherein the light provided is sufficient to kill bacteria but does not result in damage to healthy tissue.

103. The method of any of numbered embodiments above, wherein the level of pathogen is reduced such that there is a 3 log reduction in the number of colony forming units (cfu) of pathogens per milliliter (ml) (i.e. cfu/ml).

104. The method of any of numbered embodiments above, wherein the level of the pathogen in the irradiated tissue is reduced.

105. The method of any of numbered embodiments above, wherein the systemic or circulatory level of the pathogen is reduced.

106. The method of any of numbered embodiments 68-105, wherein 0.1 to 2000; 0.25 to 1000; 0.5 to 100; and 1.0 to 50, cm$^2$ of the surface of the burn is irradiated.

107. The method of any of numbered embodiments 68-105, whereinl to 100; 2 to 90; 5 to 80; and 10 to 50, % of the surface of the burn is irradiated.

109. The method of any of numbered embodiments 68-107, wherein the irradiation is administered in a health care facility, for example, a hospital, clinic, or physician's office.

110. The method of any of numbered embodiments 68-107, wherein the irradiation is administered at a place other than a health care facility, for example, a hospital, clinic, or physician's office, for example, the irradiation is administered after discharge or exit from a health care facility, for example, a hospital, clinic, or physician's office.

111. The method of any of numbered embodiments 68-107, wherein the irradiation is initiated in a health care facility, for example, a hospital, clinic, or physician's office.

112. The method of any of numbered embodiments 68-107, wherein the irradiation is initiated at a place other than a health care facility, for example, a hospital, clinic, or physician's office, for example, the irradiation is administered after discharge or exit from a health care facility, for example, a hospital, clinic, or physician's office.

113. The method of any of numbered embodiments 68-107, wherein the irradiation is initiated in a health care facility, for example, a hospital, clinic, or physician's office and is continued at a place other than a health care facility, for example, a hospital, clinic, or physician's office.

114. The method of any of numbered embodiments above, wherein the irradiation is provided as a single treatment, for example, without a period where the irradiation ceases.

115. The method of any of numbered embodiments 68-113, wherein the irradiation is provided as a plurality of treatments, for example, the irradiation is initiated and continues for a time, is halted, and is initiated a second time.

116. The method of any of numbered embodiments 68-107, wherein the irradiation is initiated in a health care facility, for example, a hospital, clinic, or physician's office and is continued for at least 6 hours, 1 day, 7 days, or 30 days in the health care facility.

117. The method of any of numbered embodiments, wherein the irradiation is continued or reinitiated at a place other than the health care facility, and, for example, is continued for at least 6 hours, 1 day, 7 days, or 30 days at the place other than the healthcare facility.

118. The method of any of numbered embodiments above, wherein the pathogen comprises a bacterium, fungus, protozoan, or spore or cyst stage of pathogen.

119. The method of any of numbered embodiments above, wherein the pathogen comprises a bacterium from Table 3, a fungus, or a protozoan from Table 2.

120. The method of any of numbered embodiments above, wherein the pathogen comprises a drug resistant pathogen.

121. The method of any of numbered embodiments above, wherein the pathogen comprises a bacterium and is resistant to a drug from Table 3 or 4.

122. The method of any of numbered embodiments above, wherein the pathogen comprises *Acinetobacter baumannii*, for example, carbapenem-resistant *Acinetobacter baumannii*.

123. The method of any of numbered embodiments above, wherein the pathogen comprises *Pseudomonas aeruginosa*, for example, carbapenem-resistant *Pseudomonas aeruginosa*.

124. The method of any of numbered embodiments above, wherein the pathogen comprises Enterobacteriaceae, for example, carbapenem-resistant or ESBL-producing Enterobacteriaceae.

125. The method of any of numbered embodiments above, wherein the method reduces the virulence of the pathogen, reduces the amount of toxin release by a pathogen, increases the sensitivity of the pathogen to an antimicrobial agent, or renders the pathogen unable to replicate.

126. The method of any of numbered embodiments above, wherein the subject comprises a second pathogen.

127. The method of any of numbered embodiments above, wherein the subject has not been treated with an exogenous compound, for example, a dye or photosensitizer.

127b. The method of any of numbered embodiments 1-126, wherein the subject has been treated with an exogenous compound, for example, a dye or photosensitizer.

128. The method of any of numbered embodiments above, wherein, at a time during irradiation, for example, at initiation, or for the entire course of irradiation, the irradiated tissue does not comprise an exogenous compound which absorbs light at 380 nm to 500 nm, for example, an exogenous compound, for example, a dye or photosensitizer, for example, Photofrin or ALA.

129. The method of any of numbered embodiments above, wherein a second therapeutic agent is provided, for example, administered, to the subject.

130. The method of numbered embodiment above, wherein the second therapeutic agent comprises an antibiotic, Ampicillin, Methicillin, or Vancomycin.

140. The method of numbered embodiment above, wherein the antibiotic comprises an antibiotic from Table 3 or 4.

145. The method of any of numbered embodiments above, wherein the second therapeutic agent is provided systemically, for example, by intra vascular, for example, intravenous administration.

146. The method of any of numbered embodiments 68-145, wherein treatment with the second therapeutic agent is initiated prior to initiation of irradiation, at the same time as initiation of irradiation, after initiation of irradiation, during the course of irradiation, or after the course of irradiation.

147. The method of any of numbered embodiments 68-145, wherein irradiation is initiated prior to initiation of the provision of the second therapeutic agent, at the same time as initiation of provision of the second therapeutic agent, after initiation of provision of the second therapeutic agent, during the course of provision of the second therapeutic agent, or after the provision of the second therapeutic agent.

148. The method of any of numbered embodiments above, wherein the second therapeutic agent comprises an agent from Table 3, 4, or 0.5.

148a. The method of any of numbered embodiments above, further comprising administering to the subject and anesthetic, for example, a general or local anesthetic.

148b. The method of any of numbered embodiments above, where the site irradiated is in contact with an aqueous liquid, for example, saline or water.

148c. The method of any of numbered embodiments above, further comprising providing the site irradiated with an aqueous liquid, for example, saline or water.

148d. The method of any of numbered embodiments 68-148c, comprising the application of negative pressure to the wound bed.

148e. The method of numbered embodiment 148d, wherein the negative pressure is constant throughout the use of the device or throughout a portion of the time the device is contacted with the subject.

148f. The method of any of numbered embodiments 148d-148e, wherein different pressures, for example, at different times of the day, at different stages of treatment or healing, or with different wavelengths of light being applied.

148g. The method of any of numbered embodiments 148d-148e, wherein a first level of negative pressure is applied at a first point of a preselected period, for example, a 24 hour period, and a second level of negative pressure is applied at a second point of the preselected period.

148h. The method of any of numbered embodiments 148d-148e, wherein a first level of negative pressure is applied at a first stage of healing or treatment, and a second level of negative pressure is applied at a second stage of healing or treatment.

148i. The method of any of numbered embodiments 148d-148e, wherein a first level of negative pressure is applied during irradiation at a first wavelength, and a second level of negative pressure is applied during irradiation with a second wavelength.

150. A device for providing light to the surface of a subject, the device comprising:
  a) an array of a plurality of light emitting modules,
    each module of the plurality being flexibly connected to another module of the plurality, and
    each module of the plurality being capable of emitting light,
  wherein the array is configured to conform to the surface of the subject.

151. The device of numbered embodiment 150, further comprising:
  b) light or energy source.

152. The device of numbered embodiment above, further comprising:
  c) a connector for transmitting current or light from b to a.

153. The device of any of numbered embodiments above, wherein two or more modules of the plurality are configured so as to be able to emit light simultaneously.

153a. The device of any of numbered embodiments above, wherein the device is configured to allow changing the intensity of light across the wound bed so that some areas receive more light than other areas, for example, responsive to the degree of wound healing or closure.

153b. The device of any of numbered embodiments above, wherein two or more modules of the plurality are configured so as be separately controllable, for example, as to intensity.

154. The device of any of numbered embodiments above, wherein one or more modules of the plurality is configured so as to be able to simultaneously emit light at more than one wavelength.

154a. The device of any of numbered embodiments above, wherein the array of modules is flexible, stretchable, or can be molded to a surface.

155b. The device of any of numbered embodiments above, wherein the array of modules can be bent to conform to surface or body part of the subject and when bent to a conforming shape retains the conforming shape.

155c. The device of any of numbered embodiments above, wherein the array of modules can be bent to conform to a surface or body party of the subject in a plurality of dimensions, for example, in two dimensions.

155. The device of any of numbered embodiments 150-155c, wherein each module of the plurality is configured to provide light having a wavelength between 250 nm and 500 nm, and a wavelength between 280 nm and 315 nm.

156. The device of any of numbered embodiments 150-155c, wherein each module of the plurality is configured to provide light at 0.25 to 25 milliWatts/cm$^2$, for example, at the surface of the subject.

157. The device of any of numbered embodiments 150-155c, wherein each module of the plurality is configured to provide light having a wavelength between: 380 nm and 500 nm; 390 nm and 430 nm; and 395 nm and 415 nm.

157. The device of any of numbered embodiments 150-155c, wherein each module of the plurality is configured to provide light having a wavelength between: 625-690 nm, for example, for wound healing.

158. The device of any of numbered embodiments 150-155c, configured to provide light having a wavelength of 405 nm+/−10 nm.

158. The device of any of numbered embodiments 150-155c, configured to provide light having a wavelength of 405 nm+/−20 nm.

159. The device of any of numbered embodiments 150-155c, configured to provide light having a wavelength 405 nm.

160. The device of any of numbered embodiments 150-155c, wherein each module of the plurality is configured to provide light between 0.25 and 25 milliWatts/cm$^2$.

161. The device of any of numbered embodiments 150-155c, wherein each module of the plurality is configured to provide light at 6+/−3 mW/cm$^2$.

162. The device of any of numbered embodiments 150-155c, wherein each module of the plurality is configured to provide light at 6 mW/cm$^2$.

163. The device of any of numbered embodiments above, further comprising at least 2, 4, 6, 10, 20, 30, 40 or 50 modules.

164. The device of any of numbered embodiments 150-162, further comprising no more than 2, 4, 6, 10, 20, 30, 40, 50, 75, 100, 150, 200, or 400 modules.

165. The device of any of numbered embodiments 150-162, further comprising 2 to 400; 3 to 200; 4 to 100; 5 to 50; 10 to 40; or 20 to 30, modules.

166. The device of any of numbered embodiments 150-162, wherein modules of the plurality of modules are present at a density of at least 62,000 (5.0 mm hexagon diagonal area=0.00001624 m$^2$ and gives a density of 61,729), 6,800 (15.0 mm hexagon diagonal area=0.00014614 m$^2$ and gives a density of 6,843), 3,000 (22.5 mm hexagon diagonal area=0.00032882 m$^2$ and gives a density of 3,042), 600 (50.0 mm hexagon diagonal area=0.0016238 m$^2$ and gives a density of 616) modules/meter$^2$.

167. The device of any of numbered embodiments 150-162, wherein modules of the plurality of modules are present at a density of no more than 500, 3,000, 6,800, 62,000 or modules/meter$^2$.

168. The device of any of numbered embodiments 150-162, wherein modules of the plurality of modules are present at a density of 600 to 62,000; 1200 to 15,000; 1700 to 6,800; 2,400 to 3,800 (20 mm); 2,900 (23 mm) to 3,200; modules/meter$^2$.

168a. The device of any of numbered embodiments 150-162, wherein a module has a longest apex to apex distance, or a longest dimension of at least 5, 10, 20, 30, or 50 millimeters.

168b. The device of any of numbered embodiments 150-162, wherein a module has a longest apex to apex distance, or a longest dimension of no more than 5, 10, 20, 30, or 50 millimeters.

168c. The device of any of numbered embodiments 150-162, wherein a module has a longest apex to apex distance, or a longest dimension of 2.5-100; 5-50; 10-40; 15-30; or 20-30; millimeters.

168d. The device of any of numbered embodiments 150-162, wherein a module, for example, a module with a hexagonal perimeter, has a longest apex to apex distance, or a longest dimension of 20-25 millimeters.

168e. The device of any of numbered embodiments 150-162, wherein a module, for example, a module with a hexagonal perimeter, has a longest apex to apex distance, or a longest dimension of 10-50 millimeters.

168f. The device of any of numbered embodiments 150-162, wherein a module, for example, a module with a hexagonal perimeter, has a longest apex to apex distance, or a longest dimension of 22.5 millimeters.

168g. The device of any of numbered embodiments 150-162, wherein the module, for example, a hexagonal module, has a side of 2.50 mm to 25.00 mm, for example, 11.25 mm.

169. The device of any of numbered embodiments above, wherein each module of the plurality of modules comprises a light emitting device.

170. The device of numbered embodiment 169, wherein the light emitting device comprises a light emitting diode, an optical fiber, laser diodes, organic light emitting diodes (OLEDs) or quantum dots.

171. The device of any of numbered embodiments above, wherein the light emitting device is configured to emit a single wavelength.

172. The device of any of numbered embodiments 150-171, wherein a module comprises a first light emitting device which emits light at a first wavelength and a second light emitting device that emits light at a second wavelength.

173. The device of any of numbered embodiments above, wherein each module of the plurality comprises a polygonal perimeter.

174. The device of any of numbered embodiments above, wherein each module of the plurality comprises a hexagonal perimeter.

175. The device of any of numbered embodiments above, wherein a module comprises a layer configured to receive light, for example, from an edge, which is internally reflective, and comprises one or a plurality of ports for emission of light.

176. The device of any of numbered embodiments above, further comprising a diffusing member, which results in a substantially uniform level of irradiation, for example, as measured by mW/cm$^2$.

177. The device of any of numbered embodiments above, wherein the module is configured such that, and the level of light delivered is such that, sufficient heat to cause thermal injury, to inhibit kearatinocyte growth, to inhibit fibroblast growth, or to inhibit wound healing, is not transferred to the subject.

178. The device of any of numbered embodiments above, wherein the plurality of modules is provided as an array.

179. The device of any of numbered embodiments 150-178, wherein the array comprises at least 2, 4, 6, 10, 20, 30, 40 or 50 modules.

180. The device of any of numbered embodiments 150-178, wherein the array comprises no more than 2, 4, 6, 10, 20, 30, 40, 50, 75, 100, 150, 200, or 400 modules.

181. The device of any of numbered embodiments 150-178, wherein the array comprises 2 to 400; 3 to 200; 4 to 100; 5 to 50; 10 to 40; or 20 to 30, modules.

182. The device of any of numbered embodiments 150-178, wherein modules are present in the array at a density of at least 250, 3,000, 6,800, 100,000 modules/meter$^2$.

183. The device of any of numbered embodiments 150-178, wherein modules of the plurality of modules are present at a density of no more than 500, 3,000, 6,800, 62,000 or modules/meter$^2$.

184. The device of any of numbered embodiments 150-178, wherein modules of the plurality of modules are present at a density of 600 to 62,000; 1200 to 15,000; 1700 to 6,800; 2,400 to 3,800 (20 mm); 2,900 (23 mm) to 3,200; modules/meter$^2$.

185. The device of any of numbered embodiments above, wherein a major perimeter side of a first module, for example, a hexagonal module, and a major perimeter side of a second module, for example, a hexagonal module, are spaced apart, for example, spaced apart so as to optimize 1) flexibility and 2) maximize uniformity of the light filed.

185a. The device of any of numbered embodiments above, wherein the device, for example, the module array of the device, is configured such that the surface of the subject under a plurality of modules, or under the module array, receives a uniform level of irradiation, for example, the level of irradiation does not differ by more than 1%, 5%, 10%, 20%, 25%, or 30%.

185b. The device of any of numbered embodiments above, wherein the device, for example, the module array of the device, is configured such that it has a bend radius of 5 mm.

185c. The device of any of numbered embodiments above, wherein the device, the module array of the device, is configured such that the array can be applied to a site on the surface of the subject with the faces of the modules that against the subject lie flat against the subject.

185d. The device of numbered embodiment above, wherein the site comprises an arm, a leg, the neck, the torso, or the head, and the array covers at least 25%, 50%, 75%, or 100% of the circumference of the subject.

186. The device of any of numbered embodiments above, wherein the spacing between a major perimeter side of a first module and a major perimeter side of a second module is: less than 2%, 5%, 10% or 15% of the longest apex to apex dimension of a module.

187. The device of any of numbered embodiments above, wherein the spacing between a major perimeter side of a first module and a major perimeter side of a second module is: less than 2% to 15%; 3% to 12%; or 4% to 8% of the longest apex to apex dimension of a module.

188. The device of any of numbered embodiments 150-186, wherein the spacing between a major perimeter side of a first module and a major perimeter side of a second module is:
less than 0.75 mm, 1.5 mm, 3.0 mm, or 7.5 mm.

189. The device of any of numbered embodiments 150-186, wherein the spacing between a major perimeter side of a first module and a major perimeter side of a second module is:
less than 0.75 mm to 7.5 mm; 1.0 mm to 3.0 mm; or 1.5 mm to 2.0 mm.

190. The device of any of numbered embodiments 150-186, wherein the spacing between a major perimeter side of a first module and a major perimeter side of a second module is:
0.75 mm, 1.5 mm, 3.0 mm, or 7.5 mm.

191. The device of any of numbered embodiments 150-186, wherein the spacing between a major perimeter side of a first module and a major perimeter side of a second module is:
1.6+/−10% millimeters.

192. The device of any of numbered embodiments 150-186, wherein the spacing between a major perimeter side of a first module and a major perimeter side of a second module is:
1.6 mm.

193. The device of numbered embodiment above, wherein a module has a proximal face that faces the surface of the subject and a distal face that faces way from the surface of the subject.

193a. The device of any of numbered embodiments above, wherein the array comprises:
a backing member, for example, flexible material, for example, a layer of foam, which covers or contacts a plurality of modules of the array; and
b) optionally, an adhesive member disposed between the backing member and a module.

193c. The device of numbered embodiment above, wherein the backing member is adjacent the distal face of a module.

193d. The device of any of numbered embodiments above, wherein the array comprises a diffusion member, for example, a translucent member which allows the passage of light from a plurality of modules but results in a more uniform field of irradiation than would be seen in its absence.

193e. The device of numbered embodiment above, wherein the diffusion member is adjacent the proximal face of a module.

193f. The device of any of numbered embodiments above, wherein the array comprises a reflective member or layer configured so as to reflect or transmit light in a way to homogenize the light uniformity or to generate specific Bi-directional Reflection Distribution functions (BDRF) that can limit the light profile to specific angular and radiometric light output.

194. The device of any of numbered embodiments above, wherein modules are present in the array having an X axis and a Y axis and the array is at least 1, 3, 10, or 100 modules in length along the X axis and at least 1, 3, 10, or 100 modules in length along the Y axis.

194a. The device of numbered embodiment 194, wherein X is 3, or more, and Y is 12 or more.

195. The device of any of numbered embodiments 1-194a, wherein modules are present in the array having an X axis and a Y axis and the array is no more than 5 mm, 10 mm, 25 mm, or 50 mm modules in length along the X axis and no more than 5 mm, 10 mm, 25 mm, or 100 mm modules in length along the Y axis.

196. The device of any of numbered embodiments 1-194a, wherein modules are present in the array having an X axis and a Y axis and the array is 5 mm to 50 mm; 10 mm to 40 mm; 15 mm to 30 mm; or 20 mm to 25 mm, modules in length along the X axis and is 5 mm to 50 mm; 10 mm to 40 mm; 15 mm to 30 mm; or 20 mm to 25 mm, modules in length along the Y axis.

197. The device of any of numbered embodiments 1-194a, wherein modules are present in the array having an X axis and a Y axis and the array is at least 0.5, 1.0, 2.5, or 5.0 centimeters in length along the X axis and at least 0.5, 1.0, 2.5, or 5.0 centimeters in length along the Y axis.

198. The device of any of numbered embodiments 1-194a, wherein modules are present in the array having an X axis and a Y axis and the array is no more than 0.5, 1.0, 2.5, or 5.0 centimeters in length along the X axis and no more than 0.5, 1.0, 2.5, or 5.0 centimeters in length along the Y axis.

199. The device of any of numbered embodiments 1-194a, wherein modules are present in the array having an X axis and a Y axis and the array is 0.5 to 5.0; 1.0 to 4.0; 1.5 to 3.0; or 2.0 to 2.5, centimeters in length along the X axis and is 0.5 to 5.0; 1.0 to 4.0; 1.5 to 3.0; or 2.0 to 2.5, centimeters in length along the Y axis.

200. The device of any of numbered embodiments above, wherein the array is configured to cover the head, neck, back, torso, an arm, a leg, genitals, a finger, or toe.

201. The device of any of numbered embodiments above, further comprising an array of modules configured for engagement with a second array of modules.

202. The device of any of numbered embodiments above, further comprising an array of modules engaged with a second array of modules.

202. The device of any of numbered embodiments above, further comprising an array of modules configures so as to be coupled with a second array of modules.

203. The device of any of numbered embodiments above, further comprising a sensor.

204. The device of any of numbered embodiments above, wherein the sensor comprises a temperature sensor, for example, a thermistor.

205. The device of any of numbered embodiments above, wherein the sensor comprises a pH sensor.

206. The device of any of numbered embodiments above, wherein the sensor comprises an $O_2$ sensor, for example, a sensor which allows evaluation of oxyhemoglobin/deoxyhemoglobin levels.

207. The device of any of numbered embodiments above, wherein the sensor comprises a pressure sensor.

208. The device of any of numbered embodiments above, wherein the sensor comprises a turbidity sensor.

209. The device of any of numbered embodiments above, wherein the sensor comprises a fluid sensor.

210. The device of any of numbered embodiments above, further comprising one, two, three, four, five or all of: a temperature sensor, a pH sensor, an $O_2$ sensor, a pressure sensor, a turbidity sensor, or a fluid sensor.

211. The device of any of numbered embodiments above, wherein a sensor is connected, for example, wirelessly connected, with a processor or computer.

212. The device of any of numbered embodiment above, responsive to a signal from the sensor, the device, or a processor or computer connected thereto, provides a signal, for example, an alert, to another device or a person, for example, the subject or a caregiver.

213. The device of any of numbered embodiment above, responsive to a signal from the sensor, the device, or a processor or computer connected thereto, alters an activity or property of the device.

214. The device of numbered embodiment above, wherein the device is responsive to a signal from the sensor, or a processor or computer connected thereto, to alter a level of irradiation.

215. The device of any of numbered embodiments above, further comprising an element for positioning the device or the array against the subject, for example, an inflatable device.

216. The device of numbered embodiment above, wherein the device is responsive to a signal from the sensor, or a processor or computer connected thereto, to alter a parameter, for example, pressure, of the element for positioning.

216a. The device of any of numbered embodiments above, wherein the irradiation is provided by a wearable device.

216b. The device of any of numbered embodiments above, wherein the irradiation is provided by a device weighing less than 15, 10, 5, or 2 kilograms.

216c. The device of any of numbered embodiments above, wherein the irradiation is provided by a device comprising a power source, for example, a wearable power source.

216d. The device of any of numbered embodiments above, wherein the irradiation is provided by a device comprising a battery.

216e. The device of any of numbered embodiments above, wherein the irradiation is provided by a device described herein, for example, in any of numbered embodiments above.

216f. The device of any of numbered embodiments above, configured to function in a wet environment, for example, when applied to a site on the subject comprising an aqueous liquid, for example, saline or water.

216g. The device of any of numbered embodiments above, wherein the device is implanted within the subject, for example, the device is a component of an implantable medical device, for example, a stent, for example, a biliary stent.

216h. The device of numbered embodiment above, wherein the device is powered by an external power source, a battery, or an implanted power source, for example, a battery, or an implanted power source that is charged, for example, inductively, for example, by a charger that is not implanted.

216i. The device of any of numbered embodiments 150-216h, wherein the device is configured for placement and use in a natural orifice, for example, the mouth, ear, nose, rectum, vagina or uterus.

216j. The device of any of numbered embodiments 150-216h, wherein the device is configured for areas with tight bend radius of curvature, for example, the face or distal extremities.

216k. The device of any of numbered embodiments 150-216h, wherein the device is configured as a glove (full or partial) for burns on the hand or one or more fingers, or a skin mask for burns on the face.

216l. The device of any of numbered embodiments above, wherein the device comprises a material that functions as a heat sink.

216m. The device of any of numbered embodiments above, wherein the device comprises a cooling device, for example, a fan.

216n. The device of any of the numbered embodiments above, configured to place the wound bed at sub-atmospheric (negative) pressure.

216o. The device of any of the numbered embodiments above, comprising a non-adherent member configured to be adjacent to the wound bed.

216p. The device of any of the numbered embodiments above, configured such that an array of a plurality of light emitting modules, is disposed between the wound bed and a gas impermeable member which allows a pressure differential between the wound bed, or the space defined by the gas impermeable membrane (the reduced pressure space), and ambient atmosphere.

216q. The device of any of the numbered embodiments 216o-216p, wherein the non-adherent member, for example, a light emitting element, for example, an array of a plurality of light emitting modules, comprises a synthetic rayon mesh material, a closed-cell foam, or a low surface coatings and materials.

216r. The device of any of the numbered embodiments 216o-216q, wherein the non-adherent member, non-adherent member is separate from or is integral with another element of the device, for example, a light emitting member or array, for example, hexagonal members.

216s. The device of any of the numbered embodiments above, wherein a light emitting element, for example, an array of a plurality of light emitting modules, has a non-adherent member, for example, a layer, disposed, for example, formed or coated on a surface that faces the wound bed.

216t. The device of any of the numbered embodiments above, comprising an array of light emitting modules having a non-adherent surface exposed to the wound bed, an absorbent element positioned to accept exudate or other liquid produced or present at the wound bed, and an element that seals the device with the subject allowing for the maintenance of negative pressure at the wound bed.

216u. The device of any of the numbered embodiments above, comprising an element, for example, a non-adherent member or element, configured to allow fluid transfer, for example, transfer away from the wound bed.

220. A device for providing light to the surface of a subject, comprising:
 (a) an array of a plurality of light emitting modules,
  wherein each module of the plurality is flexibly connected to another module of the plurality; and each module of the plurality comprises
   (i) a light emitting device,
   (ii) an internally reflective layer configured to receive light from the light emitting device,
   (iii) a port for emission of light from the internally reflective layer,
   (iv) a diffusing member, and
   (v) a polygonal perimeter,
  wherein the array,
   (i) is configured to conform to the surface of the subject, and
   (ii) comprises at least 4 modules;
 (b) a light or energy source; and
 (c) a connector for transmitting current or light from (b) to (a).

221. The device of numbered embodiment 220, wherein each module of the plurality comprises a hexagonal perimeter.

222. The device of any of numbered embodiments 220-221, wherein each module of the plurality is configured to provide light at 0.25 to 25 milliWatts/cm$^2$, for example, at the surface of the subject.

223. The device of any of numbered embodiments 220-221, wherein each module of the plurality is configured to provide light having a wavelength between: 380 nm and 500 nm; 390 nm and 430 nm; and 395 nm and 415 nm.

224. The device of any of numbered embodiments above, wherein a module has a longest apex to apex distance, or a longest dimension of 5-50; 10-40; 15-30; 20-25; or 22-23; millimeters.

225. The device of any of numbered embodiments above, wherein modules are present in the array at a density of wherein modules of the plurality of modules are present at a density of 600 to 62,000; 1200 to 15,000; 1700 to 6,800; 2,400 to 3,800 (20 mm); 2,900 (23 mm) to 3,200; modules/m$^2$.

226. The device of any of numbered embodiments above, wherein a major perimeter side of a first module, for example, a hexagonal module, and a major perimeter side of a second module, for example, a hexagonal module, are spaced apart, for example, spaced apart so as to optimize 1) flexibility and 2) maximize uniformity of the light filed.

227. The device of any of numbered embodiments above, wherein the device, for example, the module array of the device, is configured such that it has a bend radius of 5 mm.

228. The device of numbered embodiment above, wherein the site comprises an arm, a leg, the neck, the torso, or the head, and the array covers at least 25, 50, 75, or 100% of the circumference of the subject.

229. The device of any of numbered embodiments above, further comprising a sensor.

230. The device of any of numbered embodiments above, comprising one, two, three, four, five or all of: a temperature sensor, a pH sensor, an $O_2$ sensor, a pressure sensor, a turbidity sensor, or a fluid sensor.

231. The device of any of numbered embodiments above, wherein a sensor is connected, for example, wirelessly connected, with a processor or computer.

232. The device of any of numbered embodiment above, responsive to a signal from the sensor, the device, or a processor or computer connected thereto, provides a signal, for example, an alert, to another device or a person, for example, the subject or a caregiver.

233. The device of any of numbered embodiment above, responsive to a signal from the sensor, the device, or a processor or computer connected thereto, alters an activity or property of the device.

233a. The device of any of the numbered embodiments above, configured to place the wound bed at sub-atmospheric (negative) pressure.

233b. The device of any of the numbered embodiments above, comprising a non-adherent member configured to be adjacent to the wound bed.

233c. The device of any of the numbered embodiments above, configured such that the array is disposed between the wound bed and a gas impermeable member which allows a pressure differential between the wound bed, or the space defined by the gas impermeable membrane (the reduced pressure space), and ambient atmosphere.

233d. The device of any of numbered embodiments 233b-233c, wherein the non-adherent member, for example, a light emitting element, for example, an array of a plurality of light emitting modules, comprises a synthetic rayon mesh material, a closed-cell foam, or a low surface coatings and materials.

233e. The device of any of the numbered embodiments 233b-233d, wherein the non-adherent member, non-adherent member is separate from or is integral with another element of the device, for example, the array.

233f. The device of any of the numbered embodiments above, wherein array has a non-adherent member, for example, a layer, disposed, for example, formed or coated on a surface that faces the wound bed.

233g. The device of any of the numbered embodiments above, the array comprises a non-adherent surface exposed to the wound bed, an absorbent element positioned to accept exudate or other liquid produced or present at the wound bed, and an element that seals the device with the subject allowing for the maintenance of negative pressure at the wound bed.

233h. The device of any of the numbered embodiments above, comprising an element, for example, a non-adherent member or element, configured to allow fluid transfer, for example, transfer away from the wound bed.

234. The device of any of numbered embodiments above, wherein the device is configured such different wavelengths of light can administered at different stages of wound healing, for example, an early stage comprises delivering anti-microbial wavelengths and a later stage comprises delivering wavelengths, for example, longer wavelengths, that promote healing.

235. A device for treating a subject, the device comprising:
a wound surface contact layer;
a rigid-flex circuit layer configured in a gapped-geometric pattern for even distribution of light and flexibility to conform to body surfaces of a wound; and
a backing layer which, with the wound surface contact layer, is configured to enclose or substantially enclose the rigid-flex circuit layer therein.

236. The device of numbered embodiment 235, wherein the rigid-flex circuit layer is a gapped-hexagon pattern.

237. The device of numbered embodiment 236, wherein the device is 5 cm×30 cm, and is configured in an offset pattern.

238. The device of numbered embodiment 236, wherein the rigid-flex circuit layer includes a plurality of hexagon-shaped light guides.

239. The device of numbered embodiment 238, wherein each light guide includes an LED provided along a side of the light guide.

240. The device of numbered embodiment 239, wherein the LED of each light guide includes an epoxy layer to protect the LED.

241. The device of numbered embodiment 238, wherein each light guide includes an internal reflective surface feature.

242. The device of numbered embodiment 241, wherein each light guide further includes an optional diffuser.

243. The device of numbered embodiment 238, wherein a bottom surface of the device is flat and a top surface of the device includes a pattern of micro-dots that are layered to evenly (and uniformly) illuminate an entire light guide surface.

244. The device of 243, wherein the pattern accounts not only for the side emitting LEDs that illuminate the hexagon-shaped light guides but accounts for other light diffusion surfaces that provide uniformity including a diffuser.

245. The device of 238, wherein the reflective PET layer (which could be combined with other diffuser, prismatic, or polarizing materials) is used as a means to create an effect of total internal reflection (TIR), which allows the light emitted by a side emitting LED attached to the side of the hexagon light guide to internally reflect light from one side of the hexagon light guide to the other side.

246. The device of numbered embodiment 235, wherein the backing layer includes a plurality of layers, including an opaque foam layer, an adhesive layer, and a plurality of PCB layers.

247. The device of numbered embodiment 246, wherein the backing layer is secured to the rigid-flex circuit layer by a plurality of adhesive locations.

248. The device of numbered embodiment 235, wherein the wound surface contact layer is fabricated from white foam.

249. The device of numbered embodiment 235, further comprising a power pack.

250. The device of numbered embodiment 249, wherein the power pack includes a rechargeable battery, a PCB control module, a power/data cable, and optionally a separate power recharge station for depleted batteries.

251. The device of numbered embodiment 250, wherein the rechargeable battery can be inserted and removed from a structure/housing of the power pack.

252. The device of numbered embodiment 251, wherein, when fully charged, the rechargeable battery can last up to 8-24 hours, and, upon charge depletion, a new fully charged battery can be inserted into the structure/housing of the power pack.

253. The device of numbered embodiment 250, wherein the power pack further is configured to receive power from a wall outlet.

254. The device of numbered embodiment 250, wherein the power pack further is configured to provide warning indicators using LEDs, sound, and/or displays.

255. The device of numbered embodiment 250, wherein the power pack further is configured to receive data from the wound dressing, which is processed and analyzed in the power pack.

256. The device of numbered embodiment 250, wherein the power pack further is configured to send data to a wireless server/network to record data and take in instructions or regiment information to individualize treatment.

257. The device of numbered embodiment 235, further comprising a light patch designed and built out of fiber optics.

258. The device of numbered embodiment 257, wherein the fiber optics are in a bundle at one end thereof to receive light from an LED source and then the light undergoes TIR through the fiber up to an opposite end thereof.

259. The device of numbered embodiment 235, further comprising a single body light guide including a single device (plate) that receives light from multiple and overlapping light sources, for example, LEDs.

260. The device of numbered embodiment 259, wherein the single body light guide is 0.5 mm and can receive light from side emitting LEDs in an array attached to a flexible PCB.

261. The device of numbered embodiment 235, further comprising an LED array associated with the rigid-flex circuit layer.

262. The device of numbered embodiment 261, wherein the LED array is configured to enable flexibility in both the vertical and horizontal directions.

263. The device of numbered embodiment 262, wherein the LED array includes a plurality of hexagon-shaped light guides, each having a size is between 15 mm to 25 mm, with a preferable size between 20 mm and 22.5 mm.

264. The device of numbered embodiment 263, wherein there is a gap between each hexagon-shaped light guide, the gap providing a pivot point and flexibility between the hexagon-shaped light guides.

265. The device of numbered embodiment 264, wherein the gap is between 0.75 mm and 2.50 mm for hexagon-shaped light guides ranging from 15 mm to 25 mm, respectively.

266. The device of numbered embodiment 264, wherein the gap is approximately 1.6 mm for hexagon-shaped light guides each approximately 22.5 mm.

266a. The device of any of the numbered embodiments above, configured to place the wound bed at sub-atmospheric (negative) pressure.

266b. The device of any of the numbered embodiments above, comprising a non-adherent member configured to be adjacent to the wound bed.

266c. The device of any of the numbered embodiments above, configured such that the array is disposed between the wound bed and a gas impermeable member which allows a pressure differential between the wound bed, or the space defined by the gas impermeable membrane (the reduced pressure space), and ambient atmosphere.

266d. The device of any of numbered embodiments 266b-266c, wherein the non-adherent member, for example the rigid-flex circuit layer, comprises a synthetic rayon mesh material, a closed-cell foam, or a low surface coatings and materials.

266e. The device of any of the numbered embodiments above, comprising an element, for example, a non-adherent member or element, configured to allow fluid transfer, for example, transfer away from the wound bed.

267. A device for providing light to the surface of a subject, comprising:
(a) an array of a plurality of light emitting modules, wherein
  (i) the plurality comprises four light emitting modules;
  (ii) each module of the plurality is flexibly connected to another module of the plurality;
  (iii) one, two, three of four of the modules of the plurality comprise(s):
    (A) a polygonal perimeter having 4, 5, or 6 major sides;
    (B) a light source;
    (C) a longest apex-to-apex dimension for a module of 5-50 millimeters; and (optionally)
(b) a non-adherent member configured to be adjacent to the subject.

268. The device of embodiment 267, wherein the light source comprises a light emitting diode.

269. The device of embodiment 268, wherein the light source comprises a plurality of light emitting diodes.

270. The device of any of embodiments 267 to 268, wherein the light source comprises a side emitting light emitting diode.

271. The device of any of embodiments 267 to 270, further comprising an energy source or energy conduit functionally coupled to the array of a plurality of light emitting modules.

272. The device of any of embodiments 267 to 271, wherein the polygonal perimeter is a hexagonal perimeter.

273. The device of any of embodiments 267 to 272, wherein the longest apex-to-apex of dimension of a module is 20+/−5 millimeters.

274. The device of any of embodiments 267 to 273, wherein the average longest apex-to-apex of dimension of the plurality of modules is 20+/−5 millimeters.

275. The device of any of embodiments 267 to 274, wherein the array is configured to allow conformation to a surface of the body of the subject.

276. The device of embodiment 267, wherein the array is configured to allow conformation to a surface of the body of the subject.

277. The device of any of embodiments 267 to 276, wherein each module of the plurality of light emitting modules comprises:
(i) an internally reflective member configured to receive light from the light emitting diode,
(ii) a port for emission of light from the internally reflective member, and
(iii) a diffusing member.

278. The device of any of embodiments 267 to 277 wherein the device, or a module of the plurality, emits light at a first wavelength of 675+/−15 nm and at a second wavelength of 830+/−20 nm.

279. The device of embodiment 277, wherein the combination of light at the first and the second wavelength is delivered at an irradiance 1.0+/−0.5 mW/cm$^2$.

280. The device of any of embodiments 267 to 277, wherein each module of the plurality of light emitting modules is configured to emit light at a wavelength that reduces microbial levels or growth.

281. The device of any of embodiments 267 to 277, wherein each module of the plurality of light emitting modules is configured to emit light at 380-430 nm.

282. The device of any of embodiments 267 to 277, wherein each module of the plurality of light emitting modules is configured to emit light at 405+/−10 nm.

283. The device of any of embodiments 267 to 277, wherein each module of the plurality of light emitting modules is configured to emit light at 405+/−15 nm.

284. The device of any of embodiments 267 to 277, wherein each module of the plurality of light emitting modules is configured to emit light at 425+/−10 nm.

285. The device of any of embodiments 267 to 277, wherein each module of the plurality of light emitting modules is configured to emit light at 425+/−15 nm.

286. The device of any of embodiments 267 to 277, wherein each module of the plurality of light emitting modules is configured to emit light at 470+/−10 nm.

287. The device of any of embodiments 267 to 277, wherein each module of the plurality of light emitting modules is configured to emit light at 470+/−15 nm.

288. The device of any of embodiments 280 to 286, wherein light is delivered at an irradiance of 1 mW/cm$^2$ to 10 mW/cm$^2$.

289. The device of any of embodiments 280 to 286, wherein light is delivered at an irradiance of 2 mW/cm$^2$ to 4 mW/cm$^2$.

290. The device of any of embodiments 280 to 286, wherein light is delivered at an irradiance of 1 mW/cm$^2$ to 4 mW/cm$^2$.

291. The device of any of embodiments 280 to 286, wherein light is delivered at an irradiance of 2 mW/cm$^2$ to 5 mW/cm$^2$.

292. The device of any of embodiments 280 to 286, wherein light is delivered at an irradiance of 1 mW/cm$^2$ to 5 mW/cm$^2$.

293. The device of any of embodiments 280 to 286, wherein light is delivered at an irradiance of about 3+/−0.5 mW/cm$^2$.

294. The device of any of embodiments 280 to 286, wherein light is delivered at an irradiance of about 3 mW/cm$^2$.

295. The device of any of embodiments 288 to 294, wherein the irradiance is the irradiance of the single recited wavelength.

296. The device of any of embodiments 288 to 294, wherein the irradiance is the combined irradiance of all wavelengths emitted.

297. The device of any of embodiments 267 to 277, wherein each module of the plurality of light emitting modules is configured to emit light at a wavelength that promotes wound healing.

298. The device of any of embodiments 267 to 277, wherein each module of the plurality of light emitting modules is configured to emit light at 650-700 nm.

299. The device of any of embodiments 267 to 277, wherein each module of the plurality of light emitting modules is configured to emit light at 675+/−10 nm.

300. The device of any of embodiments 267 to 277, wherein each module of the plurality of light emitting modules is configured to emit light at 675+/−15 nm.

301. The device of any of embodiments 267 to 277, wherein each module of the plurality of light emitting modules is configured to emit light at 675+/−20 nm.

302. The device of any of embodiments 267 to 277, wherein each module of the plurality of light emitting modules is configured to emit light at 625+/−15 nm.

303. The device of any of embodiments 267 to 277, wherein each module of the plurality of light emitting modules is configured to emit light at 690+/−15 nm.

304. The device of any of embodiments 297 to 303, wherein light is delivered at an irradiance of 0.3 mW/cm$^2$ to 2 mW/cm$^2$.

305. The device of any of embodiments 297 to 303, wherein light is delivered at an irradiance of 0.75+/−0.25 mW/cm$^2$.

306. The device of any of embodiments 297 to 303, wherein light is delivered at an irradiance of 1.0+/−0.5 mW/cm$^2$.

307. The device of any of embodiments 297 to 303, wherein light is delivered at an irradiance of about 0.75 mW/cm$^2$.

308. The device of any of embodiments 304 to 307, wherein the irradiance is the irradiance of the single recited wavelength.

309. The device of any of embodiments 304 to 307, wherein the irradiance is the combined irradiance of all wavelengths emitted.

310. The device of any of embodiments 267 to 277, wherein each module of the plurality of light emitting modules is configured to emit light at 830+/−20 nm.

311. The device of any of embodiments 267 to 277, wherein each module of the plurality of light emitting modules is configured to emit light at 810+/−20 nm.

312. The device of any of embodiments 267 to 277, wherein each module of the plurality of light emitting modules is configured to emit light at 850+/−20 nm.

313. The device of any of embodiments 310 to 312, wherein light is delivered at an irradiance of 0.3 mW/cm$^2$ to 2 mW/cm$^2$.

314. The device of any of embodiments 310 to 312, wherein light is delivered at an irradiance of 0.75+/−0.25 mW/cm$^2$.

315. The device of any of embodiments 310 to 312, wherein light is delivered at an irradiance of about 0.75 mW/cm$^2$.

316. The device of any of embodiments 313 to 315, wherein the irradiance is the irradiance of the single recited wavelength.

317. The device of any of embodiments 313 to 315, wherein the irradiance is the combined irradiance of all wavelengths emitted.

318. The device of any of embodiments 267 to 317, wherein the device, or a module of the plurality of modules, is configured to emit light of a plurality of wavelengths.

319. The device of embodiment 318, wherein the device, or a module of the plurality of modules, is configured to emit light at a wavelength from two or all of (i) any of embodiments 280 to 287; (ii) any of embodiments 297 to 303; and (iii) any of embodiments 310 to 312.

320. The device of embodiment 319, wherein the device, or a module of the plurality of modules, is configured to emit light at a wavelength from (i) and (ii).

321. The device of embodiment 319, wherein the device, or a module of the plurality of modules, is configured to emit light at a wavelength from (i) and (iii).

322. The device of embodiment 319, wherein the device, or a module of the plurality of modules, is configured to emit light at a wavelength from (ii) and (iii).

323. A device for providing light to the surface of a subject, comprising:
(a) an array of a plurality of light emitting modules, wherein
  (i) the plurality comprises four light emitting modules;
  (ii) each module of the plurality is flexibly connected to another module of the plurality;
  (iii) the modules of the plurality each comprises:
  (A) a polygonal perimeter having 6 major sides;
  (B) a light emitting diode;
  (C) an internally reflective member configured to receive light from the light emitting diode,
  (D) a port for emission of light from the internally reflective member, and
  (E) a diffusing member.
  (F) a longest apex-to-apex dimension for a module of 20+/−5 millimeters; and
(b) a non-adherent member configured to be adjacent to the subject.

324. A method for providing light to a subject comprising: providing light to the surface of a subject with a device, comprising:
(a) an array of a plurality of light emitting modules, wherein
  (i) the plurality comprises four light emitting modules;
  (ii) each module of the plurality is flexibly connected to another module of the plurality;
  (iii) one, two, three of four of the modules of the plurality comprise(s):
  (A) a polygonal perimeter having 4, 5, or 6 major sides;
  (B) a light source;
  (C) a longest apex-to-apex dimension for a module of 5-50 millimeters; and (optionally)
(b) a non-adherent member configured to be adjacent to the subject, thereby providing light to the subject.

325. The method of embodiment 324, wherein the device comprises the device of any of embodiments 267-322.

326. The method of embodiment 324, wherein the device comprises the device of embodiment 323.

327. The method of any of embodiments 324 to 326, wherein the subject has a wound and light is delivered to the wound.

328. The method of any of embodiments 324 to 327, wherein the subject has an acute wound such as a trauma, surgical, or burn wound and light is delivered to the acute wound.

329. The method of any of embodiments 324 to 327, wherein the subject has a chronic wound such as from decubitus, pressure, diabetic, venous stasis, vascular or neurotrophic ulcers and light is delivered to the chronic would.

330. The method of any of embodiments 324 to 329, wherein the wound comprises a microbial infection and the light delivered is sufficient to reduce the level of microbial infection.

331. The method of any of embodiments 324 to 330, wherein the light delivered is sufficient to promote healing of the wound.

332. The device of any of embodiments 324-331 wherein the device, or a module of the plurality, emits light at a first wavelength of 675+/−15 nm and at a second wavelength of 830+/−20 nm.

333. The device of embodiment 332, wherein the combination of light at the first and the second wavelength is delivered at an irradiance 1.0+/−0.5 mW/cm$^2$.

334. The method of any of embodiments 323 to 331, wherein is the light is of a wavelength that reduces microbial levels or growth.

335. The method of any of embodiments 323 to 331, wherein is the light is of a wavelength of 380-430 nm.

336. The method of any of embodiments 323 to 331, wherein is the light is of a wavelength of 405+/−10 nm.

337. The method of any of embodiments 323 to 331, wherein is the light is of a wavelength of 405+/−10 nm and at an irradiance of 2 mW/cm$^2$ to 4 mW/cm$^2$.

338. The method of any of embodiments 323 to 331, wherein is the light is of a wavelength of 405+/−10 nm and at an irradiance of 1 mW/cm$^2$ to 3 mW/cm$^2$.

339. The method of any of embodiments 323 to 331, wherein is the light is of a wavelength of 405+/−10 nm and at an irradiance of 2 mW/cm$^2$ to 4 mW/cm$^2$.

340. The method of any of embodiments 323 to 331, wherein is the light is of a wavelength of 405+/−10 nm and at an irradiance of 1 mW/cm$^2$ to 5 mW/cm$^2$.

341. The method of any of embodiments 323 to 331, wherein is the light is of a wavelength of 405+/−15 nm and at an irradiance of 2 mW/cm$^2$ to 4 mW/cm$^2$.

342. The method of any of embodiments 323 to 331, wherein is the light is of a wavelength of 405+/−15 nm and at an irradiance of 1 mW/cm$^2$ to 3 mW/cm$^2$.

343. The method of any of embodiments 323 to 331, wherein is the light is of a wavelength of 405+/−15 nm and at an irradiance of 2 mW/cm$^2$ to 4 mW/cm$^2$.

344. The method of any of embodiments 323 to 331, wherein is the light is of a wavelength of 405+/−15 nm and at an irradiance of 1 mW/cm$^2$ to 5 mW/cm$^2$.

345. The method of any of embodiments 323 to 331, wherein is the light is of a wavelength of 425+/−10 nm.

346. The method of any of embodiments 323 to 331, wherein is the light is of a wavelength of 470+/−10 nm.

347. The method of any of embodiments 334 to 346, wherein light is delivered at an irradiance of 1 mW/cm$^2$ to 10 mW/cm$^2$.

348. The method of any of embodiments 334 to 346, wherein light is delivered at an irradiance of 2 mW/cm$^2$ to 4 mW/cm$^2$.

349. The method of any of embodiments 334 to 346, wherein light is delivered at an irradiance of about 3+/−0.5 mW/cm$^2$.

350. The method of any of embodiments 334 to 346, wherein light is delivered at an irradiance of about 3 mW/cm$^2$.

351. The method of any of embodiments 347 to 350, wherein the irradiance is the irradiance of the single recited wavelength.

352. The method of any of embodiments 347 to 350, wherein the irradiance is the combined irradiance of all wavelengths emitted.

353. The method of any of embodiments 323 to 331, wherein each module of the plurality of light emitting modules is configured to emit light at a wavelength that promotes wound healing.

354. The method of any of embodiments 323 to 331, wherein the light is of a wavelength of 650-700 nm.

355. The method of any of embodiments 323 to 331, wherein the light is of a wavelength of 675+/−10 nm.

356. The method of any of embodiments 323 to 331, wherein the light is of a wavelength of 675+/−10 nm and at an irradiance of 0.75+/−0.25 mW/cm$^2$.

357. The method of any of embodiments 323 to 331, wherein the light is of a wavelength of 675+/−15 nm and at an irradiance of 0.75+/−0.25 mW/cm$^2$.

358. The method of any of embodiments 323 to 331, wherein the light is of a wavelength of 675+/−10 nm and at an irradiance of 1.0+/−0.5 mW/cm$^2$.

359. The method of any of embodiments 323 to 331, wherein the light is of a wavelength of 675+/−15 nm and at an irradiance 1.0+/−0.5 mW/cm$^2$.

360. The method of any of embodiments 323 to 331, wherein the light is of a wavelength of 830+/−20 nm and at an irradiance of 0.75+/−0.25 mW/cm$^2$.

361. The method of any of embodiments 323 to 331, wherein the light is of a wavelength of 830+/−20 nm and at an irradiance of 1.0+/−0.5 mW/cm$^2$.

362. The method of any of embodiments 323 to 331, comprising irradiating with light of 830+/−20 nm and light of a wavelength of 675+/−15 nm and at an irradiance 1.0+/−0.5 mW/cm$^2$.

363. The method of any of embodiments 323 to 331, wherein the light is of a wavelength of 625+/−15 nm.

364. The method of any of embodiments 323 to 331, wherein the light is of a wavelength of 690+/−15 nm.

365. The method of any of embodiments 353 to 364, wherein light is delivered at an irradiance of 0.3 mW/cm$^2$ to 2 mW/cm$^2$.

366. The method of any of embodiments 353 to 364, wherein light is delivered at an irradiance of 0.75+/−0.25 mW/cm$^2$.

367. The method of any of embodiments 353 to 364, wherein light is delivered at an irradiance of about 0.75 mW/cm$^2$.

368. The method of any of embodiments 360 to 367, wherein the irradiance is the irradiance of the single recited wavelength.

369. The method of any of embodiments 360 to 367, wherein the irradiance is the combined irradiance of all wavelengths emitted.

370. The method of any of embodiments 323 to 331, the light is of a wavelength of 830+/−20 nm.

371. The method of any of embodiments 323 to 331, the light is of a wavelength of 810+/−20 nm.

372. The method of any of embodiments 323 to 331, the light is of a wavelength of 850+/−20 nm.

373. The method of any of embodiments 370 to 372, wherein light is delivered at an irradiance of 0.3 mW/cm$^2$ to 2 mW/cm$^2$.

374. The method of any of embodiments 370 to 372, wherein light is delivered at an irradiance of 0.75+/−0.25 mW/cm$^2$.

375. The method of any of embodiments 370 to 372, wherein light is delivered at an irradiance of about 0.75 mW/cm$^2$.

376. The method of any of embodiments 373 to 375, wherein the irradiance is the irradiance of the single recited wavelength.

377. The method of any of embodiments 373 to 375, wherein the irradiance is the combined irradiance of all wavelengths emitted.

378. The device of any of embodiments 324 to 377, wherein the device, or a module of the plurality of modules, is configured to emit light of a plurality of wavelengths.

379. The device of embodiment 378, wherein the device, or a module of the plurality of modules, is configured to emit light at a wavelength from two or all of (i) any of embodiments 334-347; (ii) any of embodiments 353 to 364; and (iii) any of embodiments 370 to 372.

380. The device of embodiment 379, wherein the device, or a module of the plurality of modules, is configured to emit light at a wavelength from (i) and (ii).

381. The device of embodiment 379, wherein the device, or a module of the plurality of modules, is configured to emit light at a wavelength from (i) and (iii).

382. The device of embodiment 379, wherein the device, or a module of the plurality of modules, is configured to emit light at a wavelength from (ii) and (iii).

Other Embodiments are within the following claims:

What is claimed is:

1. A device for providing light to the surface of a subject, comprising:
    (a) an array of a plurality of light emitting modules, wherein
        (i) the plurality comprises four light emitting modules;
        (ii) each module of the plurality is flexibly connected to another module of the plurality;
        (iii) two of the modules of the plurality comprise:
            (A) a polygonal perimeter having 4, 5, or 6 major sides;
            (B) a light source including at least one side-emitting light source;
            (C) a longest apex-to-apex dimension for a module of 5-50 millimeters; and
    (b) a non-adherent member configured to be adjacent to the subject.

2. The device of claim 1, wherein the light source comprises a light emitting diode.

3. The device of claim 2, wherein the polygonal perimeter is a hexagonal perimeter.

4. The device of claim 3, wherein the longest apex-to-apex of dimension of a module is 20+/−5 millimeters.

5. The device of claim 4, wherein each module of the plurality of light emitting modules is configured to emit light at a wavelength that reduces microbial levels or growth.

6. The device of claim 5, wherein each module of the plurality of light emitting modules is configured to emit light at 405+/−15 nm.

7. The device of claim 6, wherein light is delivered at an irradiance of 1 mW/cm$^2$ to 5 mW/cm$^2$.

8. The device of claim 4, wherein each module of the plurality of light emitting modules is configured to emit light at a wavelength that promotes wound healing.

9. The device of claim 8, wherein each module of the plurality of light emitting modules is configured to emit light at 675+/−15 nm.

10. The device of claim 9, wherein light is delivered at an irradiance of 1.0+/−0.5 mW/cm$^2$.

11. The device of claim 1, wherein the array is configured to allow conformation to a surface of the body of the subject.

12. A device for providing light to the surface of a subject, comprising:
    (a) an array of a plurality of light emitting modules, wherein
        (i) the plurality comprises four light emitting modules;
        (ii) each module of the plurality is flexibly connected to another module of the plurality;
        (iii) the modules of the plurality each comprise:
            (A) a polygonal perimeter having 6 major sides;
            (B) at least one side-emitting light emitting diode;
            (C) an internally reflective member configured to receive light from the light emitting diode,
            (D) a port for emission of light from the internally reflective member,
            (E) a diffusing member, and
            (F) a longest apex-to-apex dimension for a module of 20+/−5 millimeters; and
    (b) a non-adherent member configured to be adjacent to the subject.

13. A method for providing light to a subject comprising: providing light to the surface of a subject with a device, comprising:
    (a) an array of a plurality of light emitting modules, wherein
        (i) the plurality comprises four light emitting modules;
        (ii) each module of the plurality is flexibly connected to another module of the plurality;
        (iii) two of the modules of the plurality comprise:
            (A) a polygonal perimeter having 4, 5, or 6 major sides;
            (B) a light source including at least one side-emitting light source;
            (C) a longest apex-to-apex dimension for a module of 5-50 millimeters; and
    (b) a non-adherent member configured to be adjacent to the subject, thereby providing light to the subject.

14. The method of claim 13, wherein the subject has a wound and light is delivered to the wound.

15. The method of claim 14, wherein the subject has an acute wound such as a trauma, surgical, or burn wound and light is delivered to the acute wound.

16. The method of claim 15, wherein the subject has a chronic wound such as from decubitus, pressure, diabetic, venous stasis, vascular or neurotrophic ulcers and light is delivered to the chronic wound.

17. The method of claim 16, wherein is the light is of a wavelength that reduces microbial levels or growth.

18. The method of claim 16, wherein is the light is of a wavelength of 405+/−15 nm and at an irradiance of 1 mW/cm$^2$ to 5 mW/cm$^2$.

19. The method of claim 16, wherein each module of the plurality of light emitting modules is configured to emit light at a wavelength that promotes wound healing.

20. The method of claim 16, the light is of a wavelength of 675+/−15 nm and at an irradiance 1.0+/−0.5 mW/cm$^2$.

* * * * *